US007851600B2

(12) United States Patent
Olson et al.

(10) Patent No.: US 7,851,600 B2
(45) Date of Patent: *Dec. 14, 2010

(54) ANTI-CCR5 ANTIBODY

(75) Inventors: William C. Olson, Ossining, NY (US);
Paul J. Maddon, Scarsdale, NY (US);
Naoya Tsurushita, Palo Alto, CA (US);
Paul R. Hinton, Sunnyvale, CA (US);
Maximiliano Vasquez, Palo Alto, CA (US)

(73) Assignees: Progenics Pharmaceuticals Inc., Tarrytown, NY (US); Facet Biotech Corporation, Redwood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/581,944

(22) Filed: Oct. 16, 2006

(65) Prior Publication Data

US 2008/0107595 A1    May 8, 2008

Related U.S. Application Data

(63) Continuation of application No. 10/371,483, filed on Feb. 21, 2003, now Pat. No. 7,122,185.

(60) Provisional application No. 60/358,886, filed on Feb. 22, 2002.

(51) Int. Cl.
*C07K 16/28* (2006.01)

(52) U.S. Cl. .............................. 530/388.22; 424/143.1

(58) Field of Classification Search .................. None
See application file for complete search history.

(56) References Cited

U.S. PATENT DOCUMENTS

| | | | |
|---|---|---|---|
| 4,886,743 A | 12/1989 | Hood | |
| 5,021,409 A | 6/1991 | Murrer | |
| 5,071,964 A | 12/1991 | Dustin | |
| 5,091,513 A | 2/1992 | Huston | |
| 5,126,433 A | 6/1992 | Maddon | |
| 5,215,913 A | 6/1993 | Posner | |
| 5,225,539 A | 7/1993 | Winter | |
| 5,440,021 A | 8/1995 | Chuntharapai | |
| 5,449,608 A | 9/1995 | Young | |
| 5,504,003 A | 4/1996 | Li | |
| 5,603,933 A | 2/1997 | Dwyer | |
| 5,668,149 A | 9/1997 | Oroszlan | |
| 5,817,767 A | 10/1998 | Allaway | |
| 5,854,400 A | 12/1998 | Chang | |
| 5,939,320 A | 8/1999 | Littman | |
| 5,994,515 A | 11/1999 | Hoxie et al. | |
| 6,025,154 A | 2/2000 | Li et al. | |
| 6,100,087 A | 8/2000 | Rossi et al. | |
| 6,107,019 A | 8/2000 | Allaway et al. | |
| 6,258,527 B1 | 7/2001 | Littman | |
| 6,258,782 B1 | 7/2001 | Barney et al. | |
| 6,261,763 B1 | 7/2001 | Allaway et al. | |
| 6,265,184 B1 | 7/2001 | Gray et al. | |
| 6,268,477 B1 | 7/2001 | Gray et al. | |
| 6,344,545 B1 | 2/2002 | Allaway et al. | |
| 6,448,375 B1 | 9/2002 | Samson et al. | |
| 6,511,826 B2 | 1/2003 | Li et al. | |
| 6,528,625 B1 | 3/2003 | Wu et al. | |
| 6,548,636 B2 | 4/2003 | Dragic et al. | |
| 6,692,745 B2 | 2/2004 | Olson | |
| 6,692,938 B2 | 2/2004 | Samson et al. | |
| 6,743,594 B1 | 6/2004 | Li et al. | |
| 6,759,519 B2 | 7/2004 | Li et al. | |
| 6,797,811 B1 | 9/2004 | Gray et al. | |
| 6,800,447 B2 | 10/2004 | Samson et al. | |
| 6,800,729 B2 | 10/2004 | Li et al. | |
| 6,908,734 B2 | 6/2005 | Dragic et al. | |
| 6,930,174 B2 | 8/2005 | Samson et al. | |
| 6,972,126 B2 | 12/2005 | Allaway et al. | |
| 7,060,273 B2 | 6/2006 | Olson et al. | |
| 7,118,859 B2 | 10/2006 | Litwin et al. | |
| 7,122,185 B2 | 10/2006 | Olson et al. | |
| 7,129,055 B2 | 10/2006 | Littman et al. | |
| 7,138,119 B2 | 11/2006 | Olson et al. | |
| 7,151,087 B2 | 12/2006 | Combadiere et al. | |
| 7,223,844 B2 | 5/2007 | Dimitrov et al. | |

(Continued)

FOREIGN PATENT DOCUMENTS

CN    2216990    12/1997

(Continued)

OTHER PUBLICATIONS

U.S. Appl. No. 09/663,219, filed Sep. 15, 2000, Olson et al.
U.S. Appl. No. 10/081,128, filed Feb. 22, 2002, Olson et al.
U.S. Appl. No. 09/212,793, filed Dec. 16, 1998, Olson et al.
U.S. Appl. No. 08/169,311, filed Dec. 17, 1993, Allaway et al.
U.S. Appl. No. 08/475,515, filed Jun. 7, 1995, Allaway et al.
U.S. Appl. No. 08/587,458, filed Jan. 17, 1996, Litwin.
U.S. Appl. No. 08/627,684, filed Apr. 2, 1996, Allaway et al.
U.S. Appl. No. 08/663,616, filed Jun. 14, 1996, Allaway et al.
U.S. Appl. No. 08/663,171, filed Jun. 14, 1996, Allaway et al.
U.S. Appl. No. 08/665,090, filed Jun. 14, 1996, Allaway et al.
U.S. Appl. No. 08/673,682, filed Jun. 25, 1996, Allaway et al.
U.S. Appl. No. 08/874,570, filed Jun. 13, 1997, Allaway et al.
U.S. Appl. No. 08/874,618, filed Jun. 13, 1997, Allaway et al.
U.S. Appl. No. 09/118,415, filed Jul. 17, 1998, Litwin et al.

(Continued)

*Primary Examiner*—John D Ulm
(74) *Attorney, Agent, or Firm*—John P. White; Cooper & Dunham LLP

(57) ABSTRACT

The invention is directed an anti-CCR5 antibody which comprises (i) two light chains, each light chain comprising the expression product of a plasmid designated pVK:HuPRO140-VK (ATCC Deposit Designation PTA-4097), and (ii) two heavy chains, each heavy chain comprising an expression product of either a plasmid designated pVg1:HuPRO140 HG2-VH (ATCC Deposit Designation PTA-4098) or a plasmid designated pVg1:HuPRO140 (mutB+D+I)-VH (ATCC Deposit Designation PTA-4099) or a fragment thereof which binds to CCR5 on the surface of a human cell.

27 Claims, 23 Drawing Sheets

U.S. PATENT DOCUMENTS

| | | |
|---|---|---|
| 7,345,153 B2 | 3/2008 | Litwin et al. |
| 7,501,123 B2 | 3/2009 | Roschke et al. |
| 7,666,419 B2 | 2/2010 | Olson et al. |
| 2001/0000241 A1 | 4/2001 | Li et al. |
| 2002/0045161 A1 | 4/2002 | Allaway et al. |
| 2002/0048786 A1 | 4/2002 | Rosen et al. |
| 2002/0061834 A1 | 5/2002 | Rosen et al. |
| 2002/0106374 A1 | 8/2002 | Olson et al. |
| 2002/0146415 A1 | 10/2002 | Olson et al. |
| 2002/0150888 A1 | 10/2002 | Gray et al. |
| 2002/0155429 A1 | 10/2002 | Allaway et al. |
| 2002/0177603 A1 | 11/2002 | Johnson et al. |
| 2003/0003440 A1 | 1/2003 | Lopalco et al. |
| 2003/0023044 A1 | 1/2003 | Li et al. |
| 2003/0092632 A1 | 5/2003 | Dragic et al. |
| 2003/0100058 A1 | 5/2003 | Roschker et al. |
| 2003/0166024 A1 | 9/2003 | Rosen et al. |
| 2003/0166870 A1 | 9/2003 | Wu et al. |
| 2003/0195348 A1 | 10/2003 | Combadiere et al. |
| 2004/0062767 A1 | 4/2004 | Olson et al. |
| 2004/0086528 A1 | 5/2004 | Allaway et al. |
| 2004/0110127 A1 | 6/2004 | Samson et al. |
| 2004/0151719 A1 | 8/2004 | Li et al. |
| 2004/0161739 A1 | 8/2004 | Samson et al. |
| 2004/0228869 A1 | 11/2004 | Olson et al. |
| 2004/0230037 A1 | 11/2004 | Gray et al. |
| 2005/0118677 A1 | 6/2005 | Combadiere et al. |
| 2005/0131042 A1 | 6/2005 | Flentge |
| 2005/0136061 A1 | 6/2005 | Dillon et al. |
| 2005/0154193 A1 | 7/2005 | Roschke et al. |
| 2005/0260565 A1 | 11/2005 | Gray |
| 2006/0029932 A1 | 2/2006 | Allaway et al. |
| 2006/0140977 A1 | 6/2006 | Allaway et al. |
| 2006/0154857 A1 | 7/2006 | Redfield et al. |
| 2006/0194244 A1 | 8/2006 | Allaway et al. |
| 2006/0233798 A1 | 10/2006 | Olson et al. |
| 2007/0026441 A1 | 2/2007 | Olson et al. |
| 2007/0231327 A1 | 10/2007 | Olson et al. |
| 2007/0248624 A1 | 10/2007 | Tahri et al. |
| 2007/0274986 A1 | 11/2007 | Olson et al. |
| 2009/0074766 A1 | 3/2009 | Ketas et al. |

FOREIGN PATENT DOCUMENTS

| | | |
|---|---|---|
| EP | 0815137 | 12/1996 |
| EP | 1145721 A2 | 10/2001 |
| EP | 1146055 A2 | 10/2001 |
| EP | 1146122 A2 | 10/2001 |
| EP | 1148126 A2 | 10/2001 |
| EP | 1149582 A2 | 10/2001 |
| EP | 96870021.1 | 10/2001 |
| EP | 96870102.9 | 10/2001 |
| EP | 1148127 A2 | 4/2002 |
| EP | 1199360 A2 | 4/2002 |
| EP | 0883687 B1 | 11/2004 |
| EP | 1482042 A1 | 12/2004 |
| WO | WO 92/01451 | 2/1992 |
| WO | WO 94/19017 | 9/1994 |
| WO | WO 94/22477 | 10/1994 |
| WO | WO 95/16789 | 6/1995 |
| WO | WO 96/41020 | 9/1996 |
| WO | WO 9639437 | 12/1996 |
| WO | WO 97/22698 | 6/1997 |
| WO | WO 97/26009 | 7/1997 |
| WO | WO 97/28258 | 8/1997 |
| WO | WO 97/32019 | 9/1997 |
| WO | WO 97/37005 | 10/1997 |
| WO | WO 97/44055 | 11/1997 |
| WO | WO 97/44462 | 11/1997 |
| WO | WO 97/45543 | 12/1997 |
| WO | WO 97/47318 A | 12/1997 |
| WO | WO 97/47319 | 12/1997 |
| WO | WO 97/49424 | 12/1997 |
| WO | WO 98/18826 | 5/1998 |
| WO | WO 98/56421 | 12/1998 |
| WO | WO 00/35409 | 6/2000 |
| WO | WO 01/55439 | 8/2001 |
| WO | WO 01/58915 A2 | 8/2001 |
| WO | WO 01/58916 A2 | 8/2001 |
| WO | WO 01/64710 | 9/2001 |
| WO | WO 02/22077 | 3/2002 |
| WO | WO 02/064612 A2 | 8/2002 |
| WO | WO 02/068608 | 9/2002 |
| WO | WO 02/083172 | 10/2002 |
| WO | WO 03/072766 | 9/2003 |
| WO | WO 2007/014114 | 2/2007 |

OTHER PUBLICATIONS

U.S. Appl. No. 09/724,105, filed Nov. 28, 2000, Allaway et al.
U.S. Appl. No. 60/358,886, filed Feb. 22, 2002, Olson et al.
U.S. Appl. No. 60/014,532, filed Apr. 2, 1996, Allaway et al.
U.S. Appl. No. 60/017,157, filed May 20, 1996, Littman et al.
U.S. Appl. No. 60/266,738, filed Feb. 6, 2001, Olson et al.
U.S. Appl. No. 60/282,380, filed Apr. 6, 2001, Olson et al.
U.S. Appl. No. 60/019,715, filed Jun. 14, 1996, Olson et al.
U.S. Appl. No. 60/019,941, filed Jun. 14, 1996, Allaway et al.
U.S. Appl. No. 60/112,532, filed Dec. 16, 1998, Olson et al.
U.S. Appl. No. 60/185,667, filed Feb. 29, 2000, Dragic et al.
U.S. Appl. No. 60/205,839, filed May 19, 2000, Dragic et al.
U.S. Appl. No. 60/267,231, filed Feb. 7, 2001, Dragic et al.
U.S. Appl. No. 60/272,203, filed Feb. 28, 2001, Dragic et al.
U.S. Appl. No. 60/018,508, filed May 28, 1996, Combadiere et al.
PCT International Preliminary Examination Report issued Oct. 18, 1996 for International Application Publication No. WO 95/16789.
PCT International Preliminary Examination Report issued Sep. 5, 1997 for International Application Publication No. WO 96/41020.
PCT International Preliminary Examination Report issued Jan. 27, 2000 for International Application Publication No. WO 98/56421.
PCT International Preliminary Examination Report issued Jul. 10, 1998 for International Application Publication No. WO 97/37005.
PCT International Preliminary Examination Report issued Oct. 16, 1999 for International Application Publication No. WO 97/47319.
PCT International Preliminary Examination Report issued Dec. 24, 2003 for International Application Publication No. WO 02/083172.
PCT International Search Report issued Mar. 13, 1995 for International Application Publication No. WO 95/16789.
PCT International Search Report issued Oct. 10, 1996 for International Application Publication No. WO 96/41020.
PCT International Search Report issued Jun. 9, 1997 for International Application Publication No. WO 97/26009.
PCT International Search Report issued Jul. 5, 1997 for International Application Publication No. WO 98/56421.
PCT International Search Report issued Sep. 12, 1998 for International Application Publication No. WO 98/56421.
PCT International Search Report issued Sep. 3, 1997 for International Application Publication No. WO 97/47319.
PCT International Search Report issued Sep. 3, 1997 for International Application Publication No. WO 97/47318.
PCT International Search Report issued Apr. 23, 2002 for International Application Publication No. WO 02/22077.
PCT International Search Report issued Jul. 31, 2003 for International Application Publication No. WO 02/083172.
European Supplementary Search Report issued Sep. 5, 2002 for European Patent Application No. 95905987.4.
European Supplementary Search Report issued Feb. 24, 2000 for European Patent Application No. 96921473.3.
European Supplementary Search Report issued Mar. 6, 2002 for European Patent Application No. 97917856.3.
European Supplementary Search Report issued Apr. 27, 2006 for European Patent Application No. 01970984.9.
European Supplementary Partial Search Report issued Feb. 19, 2003 for European Patent Application No. 98931261.6.

European Supplementary Partial Search Report issued Aug. 26, 2004 for European Patent Application No. 97930120.7.
European Supplementary Partial Search Report issued Nov. 8, 2004 for European Patent Application No. 97930120.7.
European Patent Office Communication issued Nov. 11, 2004 in connection with European Patent Application No. 97930120.7.
Genbank Sequence Report, Accession Entry X91492 for *H. sapiens* Chem13, submitted Sep. 14, 1995.
Janeway and Travers (1994). Immunobiology, Current Biology Ltd., San Francisco. pp. 10:27-10:42.
Stryer (1988). Biochemistry, 3rd edition. pp. 984-988.
Dec. 17, 2003 Third Party Observations in connection with European Application No. 97904948.3.
Feb. 27, 2004 Third Party Observations in connection with European Application No. 97904948.3.
Abaza, M.S.I. and Astassi, M.Z. (1992). Effects of Amino Acid Substitutions Outside an Antigenic Site on Protein Binding to . . . J. Prot. Chem., 11(5):433-443.
Alexander, H., et al. (1992). Altering the Antigenicity of Proteins. Proc. Natl. Acad. Sci., 89:3352-3356.
Alkhatib, et al. (1996). Abstract At 3rd Conference on Retroviruses.
Alkhatib, G., et al. (1996). CC CKR5: A Rantes, MIP-1a, MIP-1β Receptor As a Fusion Cofactor for Macrophage-Tropic HIV-1. Science, 272:1955-1958.
Alkhatib, G., et al. (1997). HIV Co-Receptor Activity of CCR5 and Its Inhibition by Chemokines: Independence From G Protein Signaling . . . Virology, 234:340-348.
Allan, J. (1997) "Human Immunodeficiency . . . ", in AIDS: Biology, Diagnosis, . . . , 4th edition, De Vita, Jr., et al., eds., Lippincott-Raven Publishers, Philadelphia. pp. 15-27.
Arenzana-Selsdedos, F., et al. (1996). HIV Blocked by Chemokine Antagonist. Nature, 383:400.
Arthos, J., et al. (1989). Identification of the Residues in Human CD4 Critical for the Binding of HIV. Cell, 57:469-481.
Ashorn, P.A., et al. (1990). Human Immunodeficiency Virus Envelope Glycoprotein/CD4 Mediated Fusion of Nonprimate Cells With Human Cells. J. Virol., 64:2149-2156.
Attanasio, et al. (1991). Anti-Idiotypic Antibody Response to Monoclonal Anti-CD4 Preparations in Nonhuman Primate Species. J. Immunol., 146:507-514.
Baba, et al. (1998). Mechanism of Inhibitory Effect of Dextran Sulfate and Heparin on Replication of Human Immunodeficiency Virus in . . . Proc. Natl. Acad. Sci., 85:6132-6135.
Back, D.J. (1999). Pharmacological Issues Relating to Viral Resistance. Infection, 27(Suppl.2):S42-S44.
Balzarini, et al. (1995). Suppression of the Breakthrough of HIV-1 in Cell Culture by Thiocarboxanilide Derivatives When Used . . . Proc. Natl. Acad. Sci., 92:5470-5474.
Baulerle and Huttner (1987). Tyrosine Sulfation Is a Trans-Golgi-Specific Protein Modification. Cell. Biol., 105:2655-2663.
Benet, et al. (1990). "Pharmacokinetics: . . . ", in Goodman and Gilman's The Pharmacological Basis of Therapeutics, Gilman, et al., eds., Pergamon Press, New York. pp. 3-32.
Berger, et al. (1996). Abstract No. 002, 8 at Keystone Symposium.
Berger, et al. (1999). Chemokine Receptors As HIV-1 Coreceptors: Roles in Viral Entry, Tropism and Disease. Ann. Rev. Immunol., 17:657-700.
Blanpain, C., et al. (1999). Multiple Charged and Aromatic Residues in CCR5 Amino-Terminal Domain Are Involved in High Affinity Binding . . . J. Biol. Chem., 274:34719-34727.
Bleul, C.C., et al. (1991). The Lymphocyte Chemoattractant SDF-1 Is a Ligand for LESTR/Fusion and Blocks HIV-1 Entry. Nature, 382:829-832.
Brenner, T.J., et al. (1996). Relation Between HIV-1 Syncytium Inhibition Antibodies and Clinical Outcome in Children. Lancet, 337:1001-1005.
Broder, et al. (1993). The Block to HIV-1 Envelope Glycoprotein-Mediated Membrane Fusion in Animal Cells Expressing Human CD4 Can Be . . . Virol., 193:483-491.
Broder, et al. (1996). HIV and the 7-Transmembrane Domain Receptors. Pathobiology, 64(4):171-179.

Burkly, L., et al. (1995). Synergistic Inhibition of Human Immunodeficiency Virus Type 1 Envelope Glycoprotein-Mediated Cell . . . J. Virol., 69:4267-4273.
Burton, D.R., et al. (1994). Efficient Neutralization of Primary Isolates of HIV-1 by a Recombinant Human Monoclonal Antibody. Science, 266:1024-1027.
Busso, et al. (1991). HIV-Induced Syncytium Formation Requires the Formation of Conjugates Between Virus-Infected and Uninfected T-Calls In Vitro. AIDS, 5:1425-1432.
Camerini, D., et al. (1990). A CD4 Domain Important for HIV-Mediated Syncytium Formation Lies Outside the Virus Binding Site. Cell, 60(5):747-754.
Cammack, N. (1999). Human Immunodeficiency Virus Type 1 Entry and Chemokine Receptors: A New Therapeutic Target. Antiviral Chemistry and Chemotherapy, 10:53-62.
Capon, D.J., et al. (1989). Designing CD4 Immunoadhesions for AIDS Therapy. Nature, 337:525-531.
Chams, et al. (1992). Simple Assay to Screen for Inhibitors of Interaction Between the Human Immunodeficiency Virus Envelope . . . Antimicrob Agents Chemother., 36(2):262-272.
Chan, D.C., et al. (1998). Evidence That a Prominent Cavity in the Coiled Coil of HIV Type 1 Gp41 Is an Attractive Drug Target. Proc. Natl. Acad. Sci., 95:15613-15617.
Charo, et al. (1994). Molecular Cloning and Functional Expression of Two Monocyte Chemoattractant Protein 1 Receptors Reveals . . . Proc. Natl. Acad. Sci., 91:2752-2756.
Clapham, P.R., et al. (1989). Soluble CD4 Blocks the Infectivity of Diverse Strains of HIV and SIV for T Cells and Monocytes But Not for Brain and . . . Nature, 337:368-370.
Clapham, P.R., et al. (1991). Specific Cell Surface Requirements for the Infection of CD4-Positive Cells by Human Immunodeficiency . . . Virol., 181:703-715.
Cocchi, F. (1995). Identification of RANTES, MIP-1alpha and MIP-1beta As the Major HIV-Suppressive Factors Produced by CD8+ T-Cells. Science, 270:1811-1815.
Combadiere, et al. (1995). Cloning and Functional Expression of . . . J. Biol. Chem., 270, 16491-16494 (Note—Erratum in: J Biol Chem Dec. 15, 1995;270(50):30235)).
Combadiere, et al. (1996). Cloning and Functional Expression of CC CKR5, A Human Monocyte CC Chemokine Receptor Selective for MIP-1a, . . . J. Leukos. Biol., 60:147-152.
Cormier, E.G., et al. (2000). Specific Interaction of CCR5 Amino-Terminal Domain Peptides Containing Sulfotyrosines With HIV-1 . . . Proc. Natl. Acad. Sci., 97:5762-5767.
Crowe, S.M., et al. (1992). Human Immunodeficiency Virus-Infected Monocyte-Derived Macrophages Express Surface Gp120 and . . . Clin. Immunol Immunopathol., 65(2):143-151.
Cruse, et al. (1995). Illustrated Dictionary of Immunology, CRC Press, Inc, Boca Raton, FL., 143:QR180.4.C78.
Cushman, M., et al. (1991). Preparation and Anti-HIV Activities of Aurintricarboxylic Acid Fractions and Analogues: Direct Correlation . . . J. Med. Chem., 34:329-337.
Daar, E.S. (1990). High Concentrations of Recombinant Soluble CD4 Are Required to Neutralize Primary Human Immunodeficiency Virus . . . Proc. Natl. Acad. Sci., 87:6574-6578.
Dalgleish, A.G. (1995). HIV and CD26. Nature Medicine, 1:881-882.
De Clerq, et al. (1992). Potent and Selective Inhibition of Human Immunodeficiency Virus (HIV)-1 and HIV-2 Replication by a Class of . . . Proc. Natl. Acad. Sci., 89:5286-5290.
De Clerq, et al. (1994). Highly Potent and Selective Inhibition of Human Immunodeficiency Virus by the Bicyclam . . . Antimicrobial Agents and Chemotherapy, 38:668-674.
De Clerq, et al. (1995). Antiviral Therapy for Human Immunodeficiency Virus Infections. J. Clin. Microbiol. Rev., 8(2):200-239.
Deen, K.C., et al. (1988). A Soluble Form of CD4(T4) Protein Inhibits AIDS Virus Infection. Nature 331:82-84.
Deng, X, et al. (1999). A Synthetic Peptide Derived From Human Immunodeficiency Virus Type 1 Gp120 Down-Regulates the Expression . . . Blood, 94(4):1165-1173.

Dettin, et al. (2003). CCR5 N-Terminus Peptides Enhance X4 HIV-1 Infection by CXCR4 Up-Regulation. Biochem. Biophys. Res. Commun., 307(3):640-646.

Dikic (1996). Regulation of HIV-1 Infection by Chemokine Receptors. Acta. Med. Croatica, 50:163-168.

Dimitrov, et al. (1991). Initial Stages of HIV-1 Envelope Glycoprotein-Mediated Cell Fusion Monitored by a New Assay Based on . . . AIDS Res. Hum. Retroviruses, 7(10):799-805.

Ditzel, et al. (1998). The CCR5 Receptor Acts As an Alloantigen in CCR5Δ32 Homozygous Individuals: Identification of Chemokine and . . . Proc. Natl. Acad. Sci., 95(9):5241-5245.

Dragic, et al. (1992). Complementation of Murine Cells for Human Immunodeficiency Virus Envelope/CD4-Mediated Fusion in Human-Murine . . . J. Virol., 66(8):4794-4802.

Dragic, T.V., et al. (1993). Different Requirements for Membrane Fusion Mediated by the Envelopes of Human Immunodeficiency Virus . . . J. Virol., 67(4):2355-2359.

Dragic, T.V., et al. (1995). Proteinase-Resistant Factors in Human Erythrocyte Membranes Mediated CD-4 Dependent Fusion With Cells . . . J. Virol., 69:1013-1018.

Dragic, T.V., et al. (1998). Amino-Terminal Substitutions in the CCR5 Coreceptor Impair Gp120 Binding and Human Immunodeficiency . . . J. Virol., 72(1):279-285.

Dragic, et al. (2000). A Binding Pocket for a Small Molecule Inhibitor of HIV-1 Entry Within the Transmembrane . . . Proc. Natl. Acad. Sci., 97(10):5639-5644.

Ebadi, M. (1998). The Pharmacokinetic Basis of Therapeutics. CRC Desk Reference of Clinical Pharmacology, pp. 1-7.

Eckert, D.M., et al. (1999). Inhibiting HIV-1 Entry: Discovery of D-Peptide Inhibitors That Target the gp41 Coiled-Coil Pocket. Cell, 99:103-115.

Eugen-Olsen, J., et al. (1997). Heterozygosity for a Deletion in the CKR-5 Gene Leads to Prolonged AIDS-Free Survival and Slower CD4 . . . AIDS, 11:305-310.

Fahey, J.L., et al. (1992). Status of Immune-Based Therapies in HIV Infection and AIDS. Clin. Exp. Immunol., 88:1-5.

Farzan, M., et al. (1998). A Tyrosine-Rich Region in the N-Terminus of CCR5 Is Important for Human Immunodeficiency Virus Type 1 Entry . . . J. Virol., 72:1160-1164.

Farzan, M., et al. (1999). Tyrosine Sulfation of the Amino-Terminus of CCR5 Facilitates HIV-1 Entry. Cell, 96:667-676.

Farzan, M., et al. (2000). A tyrosine-sulfated peptide based on the N terminus of CCR5 interacts with a CD4-enhanced epitope of the HIV-1 . . . J. Biol. Chem., 275:33416-33521.

Feng, et al. (1996). Abstract No. 116,21 at Keystone Symposium.

Ferrer, M., et al. (1999). Selection of gp-41 Mediated HIV-1 Cell Entry Inhibitors From Biased Combinatorial Libraries of Non-Natural . . . Nature. Struct. Biol., 6:953-959.

Flexner, C. and Hendrix, C. (1997). "Pharmacology of . . . ", in AIDS: Biology, Diagnosis, . . . , 4th Edition, De Vita V., et al. eds., Lippincott-Raven Publishers. pp. 479-493.

Fouchier, et al, (1994). HIV-1 Macrophage Tropism is Determined At Multiple Levels of the Viral Replication Cycle. J. Clin. Invest., 94:1806-1814.

Fouts, T.R., et al. (1997). Neutralization of the Human Immunodeficiency Virus Type 1 Primary Isolate JR-FL by Human . . . J. Virol., 71:2779-2785.

Fox, J.L. (1994). No Winners Against AIDS. Bio/Technology, 12:128.

Freed, E.O., et al. (1991). Identification of Conserved Residues in the Human Immunodeficiency Virus Type 1 Principal . . . AIDS Res. Hum. Retroviruses, 7(10):807-811.

Frazer, J.K. and Capra, J.D. (1999). "Immunoglobulins: . . . ", in Fundamental Immunology, 4th Edition, W.E. Paul, ed., Lippincott-Raven Publishers, Philadelphia. pp. 111-182.

Furuta, R.A., et al. (1998). Capture of an Early Fusion-Active Conformation of HIV-1 gp41. Nature Struct. Biol., 5(4):276-279.

Gait, M.J and Karn, J. (1995). Progress in anti-HIV Structure Based Drug Design. TIBTECH, 13:430-438.

Gauduin, M.C., et al. (1996). Effective Ex Vivo Neutralization of Plasma HIV-1 by Recombinant Immunoglobulin Molecules. J. Virol., 70:2586-2592.

Gauduin, M.C., et al. (1997). Passive Immunization With a Human Monoclonal Antibody Protects hu-PBL-SCID Mice Against Challenge by . . . Nature Medicine, 3:1389-1393.

Golding, H., et al. (1992). LFA-1 Adhesion Molecules Are Not Involved in the Arly Stages of HIV-1 Env-Mediated Cell . . . AIDS Res. Hum. Retroviruses, 8:1593-1598.

Gong, J.H., et al. (1995). Antagonists of Monocyte Chemoattractant Protein 1 Identified by Modification of Functionally Critical . . . J. Exp. Med., 181:631-640.

Gong, J.H., et al. (1996). Rantes and MCP-3 Antagonists Bind Multiple Chemokine Receptors. J. Biol. Chem., 371:10521-10527.

Graham, et al. (1995). Candidate Aids Vaccines. New Engl. J. Med., 333:1331-1339.

Grene, et al. (2001). Anti-CCR5 Antibodies in Sera of HIV-Positive Individuals. Human Immunol., 62(2):143-145.

Harouse, J.M., et al. (1991). Inhibition of Entry of HIV-1 in Neural Cell Lines by Antibodies Against Galactosyl Ceramide. Science, 253(5017):320-323.

Harrington, R.D. and Geballe, A.P. (1993). Cofactor Requirement for Human Immunodeficiency Virus Type 1 Entry Into a CD4-Expressing Human Cell Line. J. Virol., 67:5939-5947.

Hattori, T., et al. (1989). Involvement of Tryptase-Related Cellular Protease (S) in Human Immunodeficiency Virus Type 1 . . . FEBS Letters, 248:48-52.

Haynes, B.F. (1996). Updates on the Issues of HIV Vaccine Development. Ann. Med., 28:39-41.

Heath, et al. (1997). Chemokine Receptor Usage by Human Eosinophils. The Importance of CCR3 Demonstrated Using an Antagonistic Monoclonal . . . J. Clin. Invest., 99:178-184.

Heidenreich, et al. (1995). Application of Antisense Technology to Therapeutics. Mol. Med. Today, 1:128-133.

Hildreth, et al. (1989). Involvement of a Leukocyte Adhesion Receptor (LFA-1) in HIV-Induced Syncytium Formation. Science, 244:1075-1078.

Hirata, Y. (1989). Characterization of IL-6 Receptor Expression by Monoclonal and Polyclonal Antibodies. J. Immun., 2900-2906.

Hirsch, et al. (1997). "Antiretroviral . . . ", in AIDS: Biology, Diagnosis, . . . , 4th Edition, De Vita, Jr., et al. eds., Lippincott-Raven Publishers, Philadelphia. pp. 495-508.

Howard, O.M.Z., et al. (1998). Small Molecule Inhibitor of HIV-1 Cell Fusion Blocks Chemokine Receptor-Mediated Fusion. J. Leuk. Biol., 64:6-13.

Hwang, S.S., et al. (1991). Identification of the Envelope V3 Loop As the Primary Determinant of Cell Tropism in HIV-1. Science, 253:71-74.

Jacobson, J.M., et al. (1993). Passive Immunotherapy in the Treatment of Advanced Human Immunodeficiency Virus Infection. J. Infect. Dis., 168:298-305.

Jacobson, J., et al. (1999). Results of a Phase I Trial of Single-Dose . . . Abstracts of the 39th Interscience Conference on Antimicrobial Agents and Chemotherapy 14.

Ji, H., et al. (1999). Inhibition of Human Immunodeficiency Virus Type 1 Infectivity by the gp41 Core: Role of a Conserved Hydrophobic . . . J. Virol., 73:8578-8586.

Jiang, S., et al. (1993). HIV-1 Inhibition by a Peptide. Nature, 365:113.

Jones, S.A., et al. (1997). Chemokine Antagonists That Discriminate Between Interleukin-8 Receptors. J. Biol. Chem., 272:16166-16199.

Karwowska, S. et al. (1991). Passive Immunization for the Treatment and Prevention of HIV Infection. Biotech. Therap., 2:31-48.

Katinger, H. (1994). Human Monoclonal Antibodies for Passive Immunotherapy of HIV-1. Antibiot. Chemother., 46:23-37.

Keller, P.M., et al. (1977). A Fluorescence Enhancement Assay of Cell Fusion. J. Cell Sci., 28:167-177.

Kilby, J.M., et al. (1998). Potent Suppression of HIV-1 Replication in Humans by T-20, A Peptide Inhibitor of gp41-Mediated Virus Entry. Nature Med., 4:1302-1307.

Klotman, et al. (1995). Transgenic Models of HIV-1. AIDS, 9(4):313-324.

Konishi, K., et al. (2000). Synthesis of Peptides Mimicking Chemokine Receptor CCR5 and Their Inhibitory Effects Against HIV-1 . . . Chem. Pharm. Bull., Tokyo, 48(2):308-309.

LaCasse, R.A., et al. (1999). Fusion-Competent Vaccines: Broad Neutralization of Primary Isolates of HIV. Science, 283:357-362.

Levy, J.A. (1996). Controlling HIV Pathogenesis: The Role of the Non-Cytotoxic Anti-HIV Response of CD8+ Cells. Immunology Today, 17:217-224.

Li, A., et al. (1997). Synergistic Neutralization of Chimeric SIV/HIV Type 1 Virus With Combinations of Human Anti-HIV Type 1 . . . AIDS Res. Hum. Retroviruses, 12:647-56.

Litwin, V.M., et al. (1996). Human Immunodeficiency Virus Type 1 Membrane Fusion Mediated by a Laboratory-Adapted Strain and A . . . J. Virol., 70(9):6437-6441.

Loetscher, M. et al. (1994). Cloning of a Human Seven Transmembrane Domain Receptor, LESTR, That is Highly Expressed in . . . J. Biol. Chem., 269:232-237.

Maddon, P.J., et al. (1986). The T4 Gene Encodes The AIDS Virus Receptor and Is Expressed in the Immune System and the Brain. Cell, 47:333-348.

Markosyan, R.M., et al. (2002). The Mechanism of Inhibition of HIV-1 Entry Env-Mediated Cell-Cell Fusion by Recombinant Cores of gp41 Ectodomain. Virology, 302:174-184.

Mateu, M.G., et al. (1992). Non-Additive Effects of Multiple Amino Acid Substitutions on Antigen-Antibody Recognition. European J. Immunol., 22(6):1385-1389.

Max, E. (1999). "Immunoglobulins: Molecular Genetics", in Fundamental Imunology, 4th edition, W.E. Paul, ed., Lippincott-Raven Publishers, Philadelphia. pp. 142-143.

Mellors, J.W. (1996). Closing in on Human Immunodeficiency Virus-1. Nature Medicine, 2(3):274-275.

Mitsuya, H., et al. (1985). "Protection . . .", in Retroviruses in Human Lymphoma Leukemia, Miwa, et al. eds., Japan Sci. Soc. Press, Tokyo/VNU Science Press, Utrecht. pp. 277-288.

Mittler, R.S., et al. (1989). Synergism Between Hiv gp120 and gp120-Specific Antibody in Blocking Human T. Cell Activation. Science, 245:1380-1382.

Mohan, P., et al. (1992). Sulfonic Acid Polymers As a New Class of Human Immunodeficiency Virus Inhibitors. Antiviral Res., 18:139-150.

Moser, B., et al. (1993). Interleukin-8 Antagonists Generated by N-Terminal Modification. J. Biol. Chem., 268:7125-7128.

Mosier, D.E. (1990). Immunodeficient Mice Xenografted With Human Lymphoid Cells: New Models for In-Vivo Studies of Human . . . J. Clin. Immuno., 10(4):185-191.

Nagasawa, et al. (1994). Molecular Cloning and Structure of a Pre-B-Cell Growth-Stimulating Factor. Proc. Natl. Acad. Sci., 91:2305-2309.

Nagashima, K.A., et al. (2001). Human Immunodeficiency Virus Type 1 Entry Inhibitors PRO 542 and T-20 Are Potently Synergistic in . . . J. Infect. Dis., 183:1121-1125.

Nakano, T., et al. (1995). Vascular smooth muscle cell-derived, Gla-containing growth-potentiating factor for Ca2+ mobilizing growth . . . J. Biol. Chem., 270(11):5702-5705.

Neote, et al. (1993). Molecular cloning, functional expression, and signaling characteristics of a C-C chemokine receptor. Cell, 72:415-425.

O'Brien, et al. (1990). HIV-1 Tropism for Mononuclear Phagocytes can be Determined by Regions of gp120 Outside of the CD4-binding domain. Nature, 348:69-73.

Oberg, B and Vrang, L. (1990). Screening for new agents. Eur. J. Clin. Microbiol. Infect. Dis., 9(7):466-471.

Oberlin, E., et al. (1996). The CXC Chemokine SDF-1 is the Ligand for LESTR/fusion and prevents infection by T-cell-line-adapted HIV-1. Nature, 382: 833-835.

Oellerich, M., (1984). Enzyme-Immunoassay: A Review. J. Clin. Chem. Clin. Biochem., 22(12):895-904.

Opperman, (2004). Chemokine Receptor CCR5: Insights Into Structure, Function, and Regulation. Cell. Signal., 16:1201-1210.

Reden, et al. (1991). Changes in Growth Properties on Passage in Tissue Culture of Viruses Derived From Infectious Molecular Clones . . . Virol., 185:661-672.

Poignard, P., et al. (1999). Neutralizing Antibodies Have Limited Effects on the Control of Established HIV-1 Infection In-Vivo. Immunity, 10:431-438.

Posner, M.R., et al. (1993). Neutralization of HIV-1 by F105, A Human Monoclonal Antibody to the CD4 Binding Site of gp120. J. Acq. Immune Defic. Synd., 6:7-14.

Power, et al. (1995). Molecular Cloning and Functional Expression of a Novel CC Chemokine Receptor cDNA From a Human Basophilic Cell Line. J. Biol. Chem., 270:1811-1815.

Proudfoot, et al. (1996). Extension of Recombinant Human RANTES By the Retention of the Initiating Methionine Produces A Potent . . . J. Biol. Chem., 271:2599-2603.

Proudfoot, et al. (1999). Chemokine Receptors: Future Therapeutic Targets for HIV. Biochem. Pharmacol., 57:451-463.

Proudfoot, et al. (2000). The Strategy of Blocking the Chemokine System to Combat Disease. Immunol. Rev., 177:246-256.

Queen, et al. (1989). A Humanized Antibody That Binds to the Interleukin 2 Receptor. Proc. Natl. Acad. Sci, 86:10029-10033.

Rabut, G.E., et al. (1991). Alanine Substitutions of Polar and Nonpolar Residues in the Amino-Terminal Domain of CCR5 Differently., J. Virol. 72:3464-3468.

Raport, C.J., et al. (1996). New Members of the Chemokine Receptor Gene Family. Journal of Leukocyte Biology, 59:18-23.

Raport, C.J., et al. (1996). AAC50598 submitted to NCBI on Apr. 12, 1996 (CC Chemokine Receptor 5 sequence).

Richman, D.D. (1996). Antiretroviral Drug-Resistance: Mechanisms, Pathogenesis, Clinical Significance. Antivir. Chemother., 4:383-395.

Rodriguez, G., et al. (1995). Mediation of Human Immunodeficiency Virus Type 1 Binding by Interaction of Cel Surface Heparin Sulfate . . . J. Virol., 69:2233-2239.

Rucker, et al. (1996). Regions in Beta-Chemokine Receptors CCR5 and CCR2b That Determine HIV-1 Cofactor Specificity. Cell, 87:437-446.

Ruffing, et al. (1998). CCR5 Has an Expanded Ligand-Binding Repertoire and is the Primary Receptor Used by MCP-2 on Activated T-Calls. Cell. Immunol., 160:160-168.

Rusche, et al. (1988). Antibodies That Inhibit Fusion of Human Immunodeficiency Virus-Infected Cells Bind a 24-Amino Acid Sequence . . . Proc. Natl. Acad. Sci., 85:3198-3202.

Sagg, M. (1997). "Clinical Spectrum . . . ", in AIDS: Biology, Diagnosis, . . . , De Vita et al., eds., Lippincott-Raven Publishers, Philadelphia. pp. 202-213.

Sandberg, J. (1995). Developmental Pharmacology and Toxicology of Anti-HIV Therapeutic Agents: Dideoxynucleosides. FASEB J., 9:1157-1163.

Sandstorm, E.G. and Kaplan, J.C. (1987). Antiviral Therapy in AIDS: Clinical Pharmacological Properties and Therapeutic Experience to Date. Drugs, 34:372-390.

Sato, et al. (1992). Anti-Co7 Reagents Inhibit HIV-1 Induced Syncytium Formation. International Conference on AIDS, 8I. PA5 PoA 2017.

Sato, et al. (1994). Identification of CD7 Glycoprotein As an Accessory Molecule in HIV-1 Mediated Syncytium Formation and Cell Free Infection. J. Immunol., 152:5142-5152.

Sato, et al. (1995). A Simple and Rapid Method for Preliminary Evaluation of In Vivo Efficacy of Anti-HIV Compounds in Mice. Antivir. Res., 27:151-163.

Scarlatti, et al. (1997). In Vivo Evolution of HIV-1 Co-Receptor Usage and Sensitivity to Chemokine-Mediated Suppression. Nature Medicine, 3(11):A258 1259-1265.

Schanberg, et al. (1995). Characterization of Human CD7 Transgenic Mice. J. of Immunol., 155:2407-2418.

Schmidtmayerova, H., et al. (1993). Characterization of HIV1-PAR, A Macrophage-Tropic Strain: Cell Tropism, Virus/Cell Entry and . . . Virology, 144(1):21-26.

Schols, D., et al. (1990). Dextran sulfate and other olyanionic anti-HIV compounds specifically interact with the viral gp120 . . . Virology, 175:556-561.

Schols, D., et al. (1991). Selective Inhibitory Activity of Polyhydroxycarboxylates Derived From Phenolic Compounds Against . . . J. Acq. Immune Defic. Synd., 4:677-685.

Sinangil, et al. (1988). Quantitative Measurement of Fusion Between Human Immunodeficiency Virus and Cultured Cells Using Membrane . . . FEB 239(1):88-92.

Sommerfelt, M.A., et al. (1995). Intercellular Adhesion Molecule 3, A Candidate Human Immunodeficiency Virus Type 1 Co-Receptor on . . . J. Gen. Virol., 76:1345-1352.

Stein, et al. (1993). Immune-Based Therapeutics: Scientific Rationale and Promising Approaches to the Treatment of the Human . . . Clin. Infect. Dis., 17:749-771.

Stewart, G.J. (1997). Increased Frequency of CCR-5Δ32 Heterozygotes Among Long-Term Non-Progressors With HIV-1 Infection. AIDS, 11:1833-1838.

Su, et al. (1996). Preparation of Specific Polyclonal Antibodies to a C-C Chemokine Receptor, CCR1, and Determination of CCR1 Expression . . . J. Leukos. Biol., 60:658-666.

Szabo, et al. (1992). Cd4 Changes Conformation Upon Ligand Binding. J. Immunol. 149(11):3596-3604.

Szabo, G. Jr., et al. (1993). Specific Disengagement of Cell-Bound Anti-LAM-1 (Anti-Selectin) Antibodies by Aurintricarboxylic Acid. Molecular Immunology, 30(18):1689-1694.

Thali, M., et al. (1992). Cooperativity of Neutralizing Antibodies Directed Against the VS and CD4 Binding Regions of the Human . . . J. Acq. Immune. Defic. Synd., 5:591-599.

Travis, B.M., et al. (1992). Functional Roles of the V3 Hypervariable Region of HIV-1 gp160 in the Processing of gp160 and . . . Virol. 186:313-317.

Tremblay, et al. (2000). Strong In Vitro Synergy Observed Between . . . Feb. 7, 2000 Conference on Retroviruses and Opportunistic Infections, abstract 500.

Tremblay, et al. (1999). Strong In Vitro Synergy Between the Fusion Inhibitor T-20 and the CXCR4 Blocker . . . Journal of Acquired Immune Deficiency Syndromes, 25(2):99-102.

Trkola, A., et al. (1999). Cross-Glade Neutralization of Primary Isolates of Human Immunodeficiency Virus Type 1 by Human Monoclonal . . . J. Virol., 73(5):4145-4155.

Trkola, A., et al. (1998). Neutralization Sensitivity of Human Immunodeficiency Virus Type 1 Primary Isolates to Antibodies and . . . J. Virol., 72:1876-1885.

Tulip, W.R., et al. (1992). Crystal Structures of Two Mutant Neraminidase-Antibody Complexes With Amino Acid Substitutions in the Interface. J. Mol. Biol., 227:149-159.

Valentin, et al. (1990). The Leukocyte Adhesion Glycoprotein CD18 Participates in HIV Induced Syncyia Formation in Monocytoid and T Cells. J. of Immunology, 144:934-937.

Valenzuela, A., et al. (1997). Neutralizing Antibodies Against the V3 Loop of Human Immunodeficiency Virus Type 1 Block the . . . J. Virol., 71(11):8289-8298.

Vanini, S., et al. (1992). Discrete Regions of HIV-1 Gp41 Defined by Syncytia-Inhibiting Affinity-Purified Human Antibodies. AIDS, 7:176-174.

Verrier, F.C., et al. (1997). Antibodies to Several Conformation-Dependent Epitopes of gp120/gp41 Inhibit CCR-5-Dependent . . . Proc. Natl. Acad. Sci., 94:9326-9331.

Vila-Coro, et al. (2000). HIV-1 Infection Through the CCR5 Receptor Is Blocked by Receptor Dimerization. Proc. Natl. Acad. Sci., 97(7):3388-3393.

Vita, C., et al. (1999). Rational Engineering of a Mini-Protein That Reproduces the Core of the CD4 Site Interacting With HIV-1 . . . Proc. Natl. Acad. Sci., 96:13091-13096.

Wang, et al. (1994). Deletion of T Lymphocytes in Human CD4 Transgenic Mice Induced by HIV-gp120 and gp120-Specific Antibodies From AIDS . . . Eur. J. Immunol., 24:1553-1557.

Wanda, P.E., and Smith, J.D., (1982). A General Method for Heterokaryon Detection Using Resonance Energy Transfer and a . . . J. Histochem. & Cytochem. 30(12):1297-1300.

Weinhold, K.J. et al. (1989). HIV 1 gp120-Mediated Immune Supression and Lymphocyte Destruction in the Absence of Viral Infection. J. Immunol., 142:3091-3097.

Wells, T.N.C., et al. (1996). Selectivity and Antagonism of Chemokine Receptors. Journal of Leukocyte Biology, 59:53-60.

Wild, C., et al. (1992). A Synthetic Peptide Inhibitor of Human Immunodeficiency Virus Replication: Correlation Between Solution . . . Proc. Natl. Acad. Sci., 89:10537-10541.

Wild, C., et al. (1993). A synthetic peptide from HIV-1 Gp41 is a Potent Inhibitor of Virus Mediated Cell-Cell Fusion. AIDS Res. Humn. Retroviruses, 9:1051-1053.

Wild, C., et al. (1994). Peptides Corresponding to a Predictive Alpha-Helical Domain of Human Immunodeficiency Virus Type 1 gp41 Are . . . Proc. Natl. Acad. Sci., 91:9770-9774.

Wild, C., et al. (1995). The Inhibitory Activity of an HIV Type 1 Peptide Correlates With Its Ability to Interact With a . . . AIDS Res. Hum. Retroviruses, 11:323-325.

Yamagami, et al. (1994). cDNA Cloning and Functional Expression of Human Monocyte Chemoattractant Protein 1 Receptor. Biochem. Biophys. Res. Commun., 212:1156-1162.

Yarchoan, et al. (1988). "Clinical . . . ", in AIDS: Etiology, Diagnosis, Treatment and Prevention, De Vita, et al., eds., Lippincott-Raven Publishers, Philadelphia. pp. 107-109.

Yarchoan, R. and Broder, S. (1992). Correlations Between the In Vitro and the In Vivo Activity of Anti-HIV Agents: Implications for . . . J. Enzyme Inhibit., 6:99-11.

Zhang, Y.J., et al. (1994). Structure / Activity Analysis of Human Monocyte Chemoattractant Protein-1 (MCP-1) by Mutagenesis. J. Biol. Chem., 269:15918-15924.

Feb. 15, 1996 Advisory Action in connection with U.S. Appl. No. 08/169,311.

Sep. 13, 1995 Final Office Action in connection with U.S. Appl. No. 08/169,311.

Nov. 23, 1994 Office Action in connection with U.S. Appl. No. 08/169,311.

Aug. 18, 1994 Office Action in connection with U.S. Appl. No. 08/169,311.

Jul. 16, 1998 Notice of Acceptance in connection with Australian Application No. 14387/95.

Nov. 27, 1996 Examiner's First Report in connection with Australian Application No. 14387/95.

Jul. 5, 2000 Notice of Acceptance in connection with Australian Application No. 62690/96.

Nov. 10, 1998 Examiner's First Report in connection with Australian Application No. 62690/96.

Sep. 14, 2006 Official Action in connection with Canadian Application No. 2,224,003.

Sep. 11, 2006 Communication Pursuant to Article 96(2) EPC in connection with European Application No. 96 921 473.3.

Mar. 8, 2006 Summons to Oral Proceedings Pursuant to Rule 71(1) EPC in connection with European Application No. 96 921 473.3.

Feb. 24, 2005 provision of the Minutes in accordance with Rule 76(4) EPC in connection with European Application No. 96 921 473.3.

Feb. 24, 2005 Decision to Refuse a European Patent Application in connection with European Application No. 96 921 473.3.

Aug. 30, 2004 Summons to Oral Proceedings Pursuant to Rule 71(1) EPC in connection with European Application No. 96 921 473.3.

Dec. 19, 2002 Communication Pursuant to Article 96(2) EPC in connection with European Application No. 96 921 473.3.

Jul. 6, 2001 Communication Pursuant to Article 96(2) EPC in connection with European Application No. 96 921 473.3.

Dec. 20, 1999 Notice of Allowance and Allowability in connection with U.S. Appl. No. 08/973,601.

Aug. 3, 1999 Advisory Action in connection with U.S. Appl. No. 08/973,601.

Mar. 25, 1999 Office Action in connection with U.S. Appl. No. 08/973,601.

Jun. 24, 1998 Office Action in connection with U.S. Appl. No. 08/973,601.

Jan. 11, 2005 Notice of Allowance and Allowability in connection with U.S. Appl. No. 09/412,284.

Dec. 2, 2003 Final Office Action in connection with U.S. Appl. No. 09/412,284.

Feb. 3, 2003 Office Action in connection with U.S. Appl. No. 09/412,284.

Apr. 8, 2002 Advisory Action in connection with U.S. Appl. No. 09/412,284.

Sep. 11, 2001 Final Office Action in connection with U.S. Appl. No. 09/412,284.

Dec. 19, 2000 Office Action in connection with U.S. Appl. No. 09/412,284.

Apr. 18, 2007 Office Action in connection with U.S. Appl. No. 11/258,963.

Dec. 26, 2006 Office Action in connection with U.S. Appl. No. 11/258,963.
Feb. 8, 2007 Office Action in connection with U.S. Appl. No. 09/904,356.
May 2, 2006 Final Office Action in connection with U.S. Appl. No. 09/904,356.
Oct. 12, 2005 Office Action in connection with U.S. Appl. No. 09/904,356.
Jul. 29, 2005 Advisory Action in connection with U.S. Appl. No. 09/904,356.
Nov. 17, 2004 Final Office Action in connection with U.S. Appl. No. 09/904,356.
Jul. 1, 2003 Office Action in connection with U.S. Appl. No. 09/904,356.
Sep. 29, 2003 Advisory Action in connection with U.S. Appl. No. 09/118,415.
Jan. 28, 2003 Final Office Action in connection with U.S. Appl. No. 09/118,415.
Apr. 9, 2002 Office Action in connection with U.S. Appl. No. 09/118,415.
Aug. 14, 2001 Advisory Action in connection with U.S. Appl. No. 09/118,415.
Nov. 24, 2000 Final Office Action in connection with U.S. Appl. No. 09/118,415.
Feb. 11, 2000 Office Action in connection with U.S. Appl. No. 09/118,415.
Aug. 3, 2006 Notice of Allowance and Allowability in connection with U.S. Appl. No. 09/891,062.
Jul. 17, 2006 Notice of Allowability in connection with U.S. Appl. No. 09/891,062.
May 18, 2006 Notice of Allowance and Allowability in connection with U.S. Appl. No. 09/891,062.
Aug. 8, 2005 Office Action in connection with U.S. Appl. No. 09/891,062.
Mar. 21, 2005 Office Action in connection with U.S. Appl. No. 09/891,062.
May 28, 2004 Advisory Action in connection with U.S. Appl. No. 09/891,062.
Sep. 24, 2003 Final Office Action in connection with U.S. Appl. No. 09/891,062.
Dec. 18, 2002 Office Action in connection with U.S. Appl. No. 09/891,062.
Apr. 30, 2007 Notice of Allowance and Allowability in connection with U.S. Appl. No. 11/544,346.
Mar. 3, 1997 Office Action in connection with U.S. Appl. No. 08/627,684.
Jun. 23, 1997 Office Action in connection with U.S. Appl. No. 08/663,616.
Mar. 13, 1997 Office Action in connection with U.S. Appl. No. 08/673,682.
Nov. 28, 2000 Notice of Acceptance in connection with Australian Application No. 26074/97.
Jul. 13, 1999 Examiner's First Report in connection with Australian Application No. 26074/97.
Oct. 23, 2006 Official Action in connection with Canadian Application No. 2,250,829.
May 27, 2005 Official Action in connection with European Application No. 2,250,829.
May 4, 2007 Summons to Attend Oral Proceedings Pursuant to Rule 71(1) EPC in connection with European Application No. 97917856.3.
Jan. 27, 2006 Communication Pursuant to Article 96(2) EPC in connection with European Application No. 97917856.3.
Oct. 21, 2005 Communication Pursuant to Article 115(2) EPC in connection with European Application No. 97917856.3.
Apr. 1, 2005 Communication Pursuant to Article 96(2) EPC in connection with European Application No. 97917856.3.
Aug. 5, 2004 Communication Pursuant to Article 96(2) EPC in connection with European Application No. 97917856.3.
Jan. 27, 2004 Communication Pursuant to Article 96(2) EPC in connection with European Application No. 97917856.3.
May 9, 2003 Communication Pursuant to Article 96(2) EPC in connection with European Application No. 97917856.3.
Mar. 6, 2002 Search Report Communication in connection with European Application No. 97917856.3.
Feb. 27, 2007 Notification of Reasons for Rejection in connection with Japanese Application No. 535610/97 (English translation).
May 19, 2006 Examiner's First Report in connection with Australian Application No. 2004233505.
Jul. 26, 2004 Notice of Acceptance in connection with Australian Application No. 35106/01.
Jul. 5, 2004 Examiner's Second Report in connection with Australian Application No. 35106/01.
Nov. 1, 2002 Examiner's First Report in connection with Australian Application No. 35106/01.
Dec. 4, 2001 Notice of Allowance and Allowability in connection with U.S. Appl. No. 08/831,823.
Jan. 16, 2001 Notice of Allowance and Allowability in connection with U.S. Appl. No. 08/831,823.
Sep. 26, 2000 Advisory Action in connection with U.S. Appl. No. 08/831,823.
Apr. 11, 2000 Final Office Action in connection with U.S. Appl. No. 08/831,823.
Jul. 21, 1999 Final Office Action in connection with U.S. Appl. No. 08/831,823.
Dec. 21, 1998 Office Action in connection with U.S. Appl. No. 08/831,823.
Aug. 17, 1998 Office Action in connection with U.S. Appl. No. 08/831,823.
Jun. 15, 2006 Final Office Action in connection with U.S. Appl. No. 09/888,938.
Sep. 7, 2005 Office Action in connection with U.S. Appl. No. 09/888,938.
Aug. 4, 2004 Office Action in connection with U.S. Appl. No. 09/888,938.
May 5, 2004 Office Action in connection with U.S. Appl. No. 09/888,938.
Jun. 22, 1999 Notice of Allowance and Allowability in connection with U.S. Appl. No. 08/876,078.
Dec. 21, 1998 Final Office Action in connection with U.S. Appl. No. 08/876,078.
Mar. 23, 1998 Office Action in connection with U.S. Appl. No. 08/876,078.
Jun. 16, 2006 Communication Pursuant to Article 96(2) EPC in connection with European Application No. 98 931 261.6.
Jun. 17, 2005 Communication Pursuant to Article 96(2) EPC in connection with European Application No. 98 931 261.6.
Oct. 17, 2006 Final Office Action in connection with U.S. Appl. No. 09/460,216.
Feb. 3, 2006 Office Action in connection with U.S. Appl. No. 09/460,216.
Jul. 29, 2005 Advisory Action in connection with U.S. Appl. No. 09/460,216.
Feb. 9, 2005 Final Office Action in connection with U.S. Appl. No. 09/460,216.
Sep. 26, 2003 Advisory Action in connection with U.S. Appl. No. 09/460,216.
Feb. 27, 2003 Final Office Action in connection with U.S. Appl. No. 09/460,216.
Oct. 2, 2001 Office Action in connection with U.S. Appl. No. 09/460,216.
Sep. 9, 2002 Notice of Acceptance in connection with Australian Application No. 81426/98.
Feb. 27, 2002 Examiner's Second Report in connection with Australian Application No. 81426/98.
Feb. 21, 2001 Examiner's First Report in connection with Australian Application No. 81426/98.
Feb. 4, 1997 Office Action in connection with U.S. Appl. No. 08/665,090.
Aug. 29, 2000 Notice of Allowance and Allowability in connection with 08/874,618.
Nov. 19, 1999 Office Action in connection with U.S. Appl. No. 08/874,618.
May 24, 1999 Final Office Action in connection with U.S. Appl. No. 08/874,618.

Sep. 2, 1998 Office Action in connection with U.S. Appl. No. 08/874,618.
Dec. 13, 2005 Final Office Action in connection with U.S. Appl. No. 09/724,105.
Mar. 23, 2005 Office Action in connection with U.S. Appl. No. 09/724,105.
Sep. 23, 2004 Office Action in connection with U.S. Appl. No. 09/724,105.
May 19, 2004 Office Action in connection with U.S. Appl. No. 09/724,105.
Dec. 19, 2006 Office Action in connection with U.S. Appl. No. 11/400,497.
Aug. 8, 2006 Office Action in connection with U.S. Appl. No. 11/400,497.
May 29, 2001 Notice of Acceptance in connection with Australian Application No. 34026/97.
Sep. 28, 1999 Examiner's First Report in connection with Australian Application No. 34026/97.
Nov. 10, 2006 Official Action in connection with Canadian Application No. 2,257,991.
May 23, 2005 Communications Pursuant to Article 96(2) EPC in connection with European Application No. 97 930 120.7.
Nov. 17, 2004 Communication of partial European search report under Rule 45 EPC in connection with European Application No. 97 930 120.7.
Sep. 9, 2004 Communication of partial European search report under Rule 46(1) EPC in connection with European Application No. 97 930 120.7.
Oct. 17, 2006 Notification of Reasons for Rejection in connection with Japanese Application No. 501895/98 (English translation).
Apr. 5, 2004 Notice of Acceptance in connection with Australian Application No. 21996/00.
Feb. 5, 2003 Examiner's First Report in connection with Australian Application No. 21996/00.
Mar. 29, 2006 Examiner's First Report in connection with Australian Application No. 20004205164.
Mar. 29, 2006 Examiner's First Report in connection with Australian Application No. 20004205165.
Mar. 1, 2006 Communication under Rule 51(4) EPC in connection with European Application No. 99 966 466.7.
Jan. 10, 2005 Communication Pursuant to Article 96(2) EPC in connection with European Application No. 99 966 466.7.
Oct. 14, 2004 Communication Pursuant to Article 96(1) and Rule 51(1) EPC in connection with European Application No. 99 966 466.7.
Jan. 18, 2007 Office communication in connection with Mexican Application No. 1006097.
Oct. 13, 2005 Office communication in connection with Mexican Application No. 1006097.
Feb. 6, 2007 Notice of Allowability in connection with U.S. Appl. No. 09/464,902.
Jan. 8, 2007 Notice of Allowance and Allowability in connection with U.S. Appl. No. 09/464,902.
Apr. 19, 2006 Office Action in connection with U.S. Appl. No. 09/464,902.
Oct. 21, 2005 Office Action in connection with U.S. Appl. No. 09/464,902.
Jun. 15, 2005 Advisory Action in connection with U.S. Appl. No. 09/464,902.
Jan. 13, 2005 Final Office Action in connection with U.S. Appl. No. 09/464,902.
Apr. 2, 2004 Office Action in connection with U.S. Appl. No. 09/464,902.
Oct. 21, 2003 Office Action in connection with U.S. Appl. No. 09/464,902.
Sep. 25, 2001 Office Action in connection with U.S. Appl. No. 09/464,902.
Aug. 7, 2006 Office Action in connection witn U.S. Appl. No. 09/594,983.
Mar. 24, 2006 Notice of Allowance and Allowability in connection with U.S. Appl. No. 09/594,983.
Jul. 11, 2005 Final Office Action in connection with U.S. Appl. No. 09/594,983.
Aug. 25, 2004 Office Action in connection with U.S. Appl. No. 09/594,983.
Sep. 23, 2003 Notice of Allowability in connection with U.S. Appl. No. 09/594,983.
Dec. 3, 2002 Final Office Action in connection with U.S. Appl. No. 09/594,983.
Mar. 13, 2002 Office Action in connection with U.S. Appl. No. 09/594,983.
Sep. 28, 2001 Office Action in connection with U.S. Appl. No. 09/594,983.
Dec. 19, 2006 Notice of Allowance and Allowability in connection with U.S. Appl. No. 10/763,545.
Jul. 26, 2006 Office Action in connection with U.S. Appl. No. 10/763,545.
Jun. 13, 2006 Office Action in connection with U.S. Appl. No. 10/763,545.
Feb. 16, 2006 Office Action in connection with U.S. Appl. No. 10/763,545.
Apr. 21, 2006 Supplementary European search report under Article 157(2)(a) in connection with European Application No. 03 713 632.2.
Sep. 7, 2005 Office Action in connection with U.S. Appl. No. 09/888,938.
May 16, 2006 Notice of Allowance and Allowability in connection with U.S. Appl. No. 10/371,483.
Oct. 24, 2006 Office Action in connection with U.S. Appl. No. 10/371,483.
Jan. 29, 2007 Examiner's First Report in connection Australian Application No. 2003217674.
Feb. 22, 2007 Communication Pursuant to Article 96(2) EPC in connection with European Application No. 03 713 632.2.
Oct. 12, 2004 Communication Pursuant to Rules 109 and 110 EPC in connection with European Application No. 03 713 632.2.
Mar. 14, 2006 Examination Report in connection with New Zealand Application No. 534947.
Feb. 21, 2003 Official Action in connection with Russian Federation Application No. 2004128252/13(030609) (English Translation).
Sep. 29, 2006 Grant of Patent in connection with Singaporean Application No. 200404610-8.
Aug. 7, 2002 Office Action in connection with U.S. Appl. No. 09/663,219.
Jan. 5, 2006 Notice of Allowance and Allowability in connection with U.S. Appl. No. 09/912,824.
Jan. 26, 2005 Final Office Action in connection with U.S. Appl. No. 09/912,824.
Apr. 20, 2004 Office Action in connection with U.S. Appl. No. 09/912,824.
Jul. 2, 2003 Office Action in connection with U.S. Appl. No. 09/912,824.
Jul. 3, 2006 Notice of Acceptance in connection with Australian Application No. 2001290925.
Jun. 28, 2005 Examiner's First Report in connection with Australian Application No. 2001290925.
May 24, 2006 Supplementary European search report under Article 157(2) (a) EPC in connection with European Application No. 01970984.9.
Feb. 28, 2005 Formalities Examination in connection with European Application No. 01970984.9.
May 2, 2003 Communication Pursuant to Rules 109 and 110 EPC in connection with European Application No. 01970984.9.
Oct. 25, 2005 Notice of Allowance and Allowability in connection with U.S. Appl. No. 09/828,615.
Sep. 13, 2005 Office Action in connection with U.S. Appl. No. 09/828,615.
Mar. 2, 2005 Office Action in connection with U.S. Appl. No. 09/828,615.
Sep. 17, 2004 Final Office Action in connection with U.S. Appl. No. 09/828,615.
Feb. 23, 2004 Office Action in connection with U.S. Appl. No. 09/828,615.
Sep. 9, 2003 Advisory Action in connection with U.S. Appl. No. 09/828,615.

Feb. 21, 2003 Final Office Action in connection with U.S. Appl. No. 09/828,615.

Jun. 25, 2002 Office Action in connection with U.S. Appl. No. 09/828,615.

Jun. 9, 2005 Notice of Allowance and Allowability in connection with U.S. Appl. No. 10/116,797.

Apr. 25, 2005 Final Office Action in connection with U.S. Appl. No. 10/116,797.

Oct. 6, 2004 Office Action in connection with U.S. Appl. No. 10/116,797.

Feb. 9, 2004 Office action in connection with U.S. Appl. No. 10/116,797.

Allaway, G.P. et al., (1993) "Synergistic Inhibition of HIV-1 Envelope-Mediated Cell Fusion by CD4-Based Molecules in Combination With Antibodies to gp120 or gp41", *AIDS Res Hum Retroviruses* 9:581-587.

Allaway, G.P. et al., (1995) "Expression and Characterization of CD4-IgG$_2$, A Novel Heterotetramer That Neutralizes Primary HIV Type 1 Isolates", *AIDS Res Hum Retrovirus* 11:533-539.

Amara, A. et al., (1997) "HIV Coreceptor Downregulation As Antiviral Principle: SDF-1α-Dependent Internalization of the Chemokine Receptor CXCR4 Contributes to Inhibition of HIV Replication", *J. Exp. Med.* 186:139-146.

Berger, E.A., (1997) "HIV Entry and Tropism: The Chemokine Receptor Connection", *AIDS* 11(Suppl A):S3-S16.

Bieniasz, P.D. et al., (1997) "HIV-1 Induced Cell Fusion Is Mediated by Multiple Regions Within Both the Viral Envelope and the CCR5 Co-Receptor", *EMBO* 16:2599-2609.

Brelot, A. et al., (1997) "Role of the First and Third Extracellular Domains of CXCR4 in Human Immunodeficiency Virus Coreceptor Activity", *J. Virol.* 71:4744-4751.

Chan, D.C. et al., (1998) "HIV Entry and Its Inhibition", *Cell* 93:681-684.

Chen, Z. et al., (1997) "Genetically Divergent Strains of Simian Immunodeficiency Virus Use CCR5 As a Coreceptor for Entry", *J. Virol.* 71(4):2705-2714.

Choe, H. et al., (1996) "The Beta-Chemokine Receptors CCR3 and CCR5 Facilitate Infection by Primary HIV-1 Isolates", *Cell* 85:1135-1148.

Co., M.S. et al., (1991) "Humanized Antibodies for Antiviral Therapy" *Proc. Natl. Acad. Sci.* 88:2869-2873.

Connor, R.I. et al., (1997) "Change in Co-Receptor Use Correlates With Disease Progression in HIV-1 Infected Individuals", *J. Exp. Med.* 185:621-628.

Crump, M.P. et al., (1997) "Solution Structure and Basis for Functional Activity of Stromal-Cell Derived Factor-1: Disassociation of CXCR4 Activation From Binding and Inhibition of HIV-1", *EMBO* 16:6996-7007.

Dalgleish, A.G. et al., (1984) "The CD4 (T4) Antigen Is an Essential Component of the Receptor for the AIDS Retrovirus", *Nature* 312:763-766.

De Rossi, A. et al., (1995) "Synthetic Peptides From the Principle Neutralizing Domain of Human Immunodeficiency Virus Type 1 (HIV-1) Enhance HIV-1 Infection Through a CD4-Dependent Mechanism", *Virology* 184:187-196.

Dean, M. et al., (1996) "Genetic Restriction of HIV-1 Infection and Progression to AIDS by a Deletion Allele of the CKR5 Structural Gene", *Science* 273:1856-1862.

Deng, H. et al., (1996) "Identification of a Major Co-Receptor for Primary Isolates of HIV-1", *Nature* 381:661-666.

Donzella, G.A. et al., (1998) "AMD3100, A Small Molecule Inhibitor of HIV-1 Entry Via the CXCR4 Co-Receptor", *Nat. Med.* 4:72-77.

Doranz, B.J. et al. (1996) "A Dual-Tropic Primary HIV-1 Isolate That Uses Fusin and Beta-Chemokine Receptors CKR-5, CKR-3 and CKR-2b As Fusion Cofactors", *Cell* 85:1149-1158.

Doranz, B.J. et al., (1997) "Two Distinct CCR5 Domains Can Mediate Co-Receptor Usage by Human Immunodeficiency Virus Type 1", *J. Virol.* 71:6305-6314.

Doranz, B.J. et al., (1997) "A Small Molecule Inhibitor Directed Against the Chemokine Receptor CXCR4 Prevents Its Use As an HIV-1 Co-Receptor", *J. Exp. Med.* 186:1395-1400.

Dragic, T.V. et al., (1996) "HIV-1 Entry Into CD4+Cells Is Mediated by the Chemokine Receptor CC-CKR-5", *Nature* 381:667-673.

Feng, Y. et al., (1996) "HIV-1 Entry Cofactor: Functional Cdna Cloning of a Seven-Transmembrane, G Protein-Coupled Receptor", *Science* 272:872-877.

Fradd, F. and Mary, M.E. (1989) "AIDS Vaccines: An Investor's Guide by Shearman Lehaman Hutton", p. 10 (Fig. 2).

Ghorpade, A. et al, (1998) "Role of the β-Chemokine Receptors CCR3 and CCR5 in Human Immunodeficiency Virus Type 1 Infection of Monocytes and Microglia", *J. Virol.* 72:3351-3361.

He, J. et al., (1997) "CCR3 and CCR5 Are Co-Receptors for HIV-1 Infection of Microglia", *Nature* 385:645-649.

Hill, C.M. et al., (1998) "The Amino Terminus of Human CCR5 Is Required for Its Function As a Receptor for Diverse Human and Simian Immunodeficiency Virus Envelope Glycoproteins", *Virology* 248:357-371.

Konigs, C. et al., (2000) "Monoclonal Antibody Screening of Phage-Displayed Random Peptide Library Reveals Mimotopes of Chemokine Receptor CCR5: Implications for the Tertiary Structure of the Receptor and for an N-Terminal Binding Site for HIV-1 Gp120", *Eur. J. Immunol.* 30(4):1162-1171.

Koup, R.A. et al., (1996) "Defining Antibody Protection Against HIV-1 Transmission in Hu-PBL-SCID Mice", *Immunology.* 8:263-268.

Kwong, P.D. et al., (1998) "Structure of an HIV gp120 Envelope Glycoprotein in Complex With the CD4 Receptor and Neutralizing Human Antibody", *Nature* 393:648-659.

Laal, S. et al., (1994) "Synergistic Neutralization of Human Immunodeficiency Virus Type 1 by Combinations of Human Monoclonal Antibodies", *J. Virol* 68:4001-4008.

Lee, B. et al., (1999) "Epitope Mapping of CCR5 Reveals Multiple Conformational States and Distinct But Overlapping Structures Involved in Chemokine Coreceptor Function", *J. Biol. Chem.* 274(14):9617-9626.

Lehner, T. et al., (2001) "Immunogenicity of the Extracellular Domains of C-C Chemokine Receptor 5 and the In Vitro Effects on Simian Immunodeficiency or HIV Infectivity", *J. Immunol.* 166(12):7446-7455.

Li, A.H. et al., (1998) "Synergistic Neutralization of Simian-Human Immunodeficiency Virus SHIV-Vpu+ by Triple and Quadruple Combination of Human Monoclonal Antibodies and High-Titer Antihuman Immunodeficiency Virus Type 1 Immunoglobulins", *J. Virol.* 72:3235-3240.

Mack, M. et al., (1998) "Aminooxypentane-RANTES Induces CCR5 Internalization But Inhibits Recycling: A Novel Inhibitory Mechanisms of HIV Infectivity", *J. Exp. Med.* 187:1215-1224.

Mackay, C.R., (1996) "Chemokine Receptors and T Cell Chemotaxis", *J. Exp. Med* 184:799-802.

McKnight, A.D. et al., (1997) "Inhibition of Human Immunodeficiency Virus Fusion by a Monoclonal Antibody to a Coreceptor (CXCR4) is Both Cell Type and Virus Strain Dependent", *J. Virol.* 71:1692-1696.

Olson, W.C. et al., (1999) "Differential Inhibition of Human Immunodeficiency Virus Type 1 Fusion, gp 120 Binding and CC-Chemokine Activity of Monoclonal Antibodies to CCR5", *J. Virol.* 73:4145-4155.

Parren, P.W. et al., (2001) "Antibody Protects Macaques Against Vaginal Challenge With a Pathogenic R5 Simian/Human Immunodeficiency Virus At Serum Levels Giving Complete Neutralization In Vitro" *J. Virol.* 75:8340-8347.

Partidos, C. et al., (1992) "The Effect of Orientation of Epitopes on the Immunogenicity of Chimeric Synthetic Peptides Representing Measles Virus Protein Sequences", *Molecular Immunology* 29(5):651-658.

Raport, C.J. et al., (1996) "Molecular Cloning and Functional Characterization of a Novel Human CC Chemokine Receptor (CCR5) for RANTES, MIP-1β, and MIP-1α", *J.Biol. Chem.* 271(29):1761-17166.

Rudikoff, S. et al., (1982) "Single Amino Acid Substitution Altering Antigen-Binding Specificity", *Proc. Natl. Acad. Sci.* 79:1979-1983.

Samson, M. et al., (1996) "Molecular Cloning and Functional Expression of a New Human CC-Chemokine Receptor Gene", *Biochem.* 35:3362-3367.

Schols, D. et al., (1999) "CD26-Processed RANTES(3-68), But Not Intact RANTES, Has Potent Anti-HIV-1 Activity", *Antiviral Res.* 30:175-187.

Simmons, G. et al., (1997) "Potent Inhibition of HIV-1 Infectivity in Macrophages and Lymphocytes by a Novel CCR5 Antagonist", *Science* 276:276-279.

Steinberger, P. et al., (2000) "Generation and Characterization of a Recombinant Human CCR5-Specific Antibody", *J. Biol. Chem.* 275(46):36073-36078.

Strizki, J.M. et al., (1997) "A Monoclonal Antibody (12G5) Directed Against CXCR4 Inhibits Infection With the Dual-Tropic Human Immunodeficiency Virus Type 1 Isolates HIV-1 89.6 But Not the T-Tropic Isolate HIV-1 Hxb", *J. Virol.* 71:5678-5683.

Tilley, S. A. (1992) "Synergistic Neutralization of HIV-1 by Human Monoclonal Antibodies Against the V3 Loop and the CD4-Binding Site gp120", *AIDS Research and Human Retroviruses* 80:4:461-467.

Tilley, S. A. et al., (1991) "Potent Neutralization of HIV-1 by Human and Chimpanzee Monoclonal Antibodies Directed Against Three Distinct Epitope Clusters of gp120", *Sixieme Colloque Des Cent Gardes* 211-216.

Trkola, A. et al., (2001) "Potent, Broad-Spectrum Inhibition of Human Immunodeficiency Virus Type 1 by the CCR5 Monoclonal Antibody PRO 140", *J. Virol.* 75:579-588.

Trkola, A. et al., (1996) "CD-4 Dependent, Antibody Sensitive Interactions Between HIV-1 and Its Co-Receptor CCR-5", *Nature* 384:184-187.

Vijh-Warrier, S. (1996) "Synergistic Neutralization of Human Immunodeficiency Virus Type 1 by a Chimpanzee Monoclonal Antibody Against the V2 Domain of gp120 in Combination With Monoclonal Antibodies Against the V3 Loop and the CD4-Binding Site", *J. Virol.* 70:4466-4473.

Wu, L. et al., (1997) "CCR5 Levels and Expression Pattern Correlate With Infectability by Macrophagetropic HIV-1 In Vitro", *J. Exp. Med.* 185(9):1681-1691.

Wu, L. et al., (1997) "Interaction of Chemokine Receptor CCR5 With Its Ligands: Multiple Domains for HIV-1 gp120 Binding and a Single Domain for Chemokine Binding", *J. Exper. Med.* 186(8):1373-1381.

Wu, L. et al., (1996) "CD4-Induced Interaction of Primary HIV-1 Gp120 Glycoproteins With the Chemokine Receptor CCR-5", *Nature* 384:179-183.

Ylisastigui, L. et al., (1998) "Synthetic Full Length and Truncated RANTES Inhibit HIV-1 Infection or Primary Macrophages", *AIDS* 12:977-984.

Office Action issued Nov. 10, 2008 in connection with U.S. Appl. No. 11/400,497.

Office Action issued Dec. 12, 2008 in connection with U.S. Appl. No. 11/491,330.

Final Office Action issued Dec. 31, 2008 in connection with U.S. Appl. No. 11/581,945.

Final Office Action issued Jan. 9, 2009 in connection with U.S. Appl. No. 11/451,707.

Final Office Action issued Jan. 27, 2009 in connection with U.S. Appl. No. 11/520,556.

Final Office Action issued Jan. 27, 2009 in connection with U.S. Appl. No. 11/259,540.

Simmons, G. et al. (1996) "Primary, syncytium-inducing human immunodeficiency virus type 1 isolates are dual-tropic and most can use either Lestr or CCR5 as coreceptors for virus entry," *J. Virol.* 70(12):8355-8360.

Valentin, A. et al. (1994) "Dual tropism for macrophages and lymphocytes is a common feature of primary human immunodeficiency virus type 1 and 2 isolates," *J. Virol.* 68(10):6684-6689.

Max, E. "Immunoglobulins: Molecular Genetics" in Fundamental Imunology, 6th edition. W.E. Paul, ed., Lippincott-Raven Publishers, Philadelphia, 2008 pp. 192-236.

Nelson et al. "Efficacy and Safety of Maraviroc plus Optimized Background Therapy in Viremic, ART-experienced Patients Infected with CCR5-tropic HIV-1 in Europe, Australia, and North America: 24-Week results," 14th Annual Conference on Retroviruses and Opportunistic Infections. Feb. 28, 2007. Abstract #104aLB. Downloaded Aug. 3, 2008 <http://www.retroconference.org/2007/Abstracts/30636.htm>.

Schroeder et al. (2008) "Immunoglobulins: Structure and Function," Fundamental Immunology, 6th Edition, Chapter 4, pp. 125-151.

Combadiere, C. et al. (1995) Additions and Corrections to "Cloning and functional expression of a human eosinophil CC chemokine receptor," J. Biol. Chem. 270(28) 16491-16494.

Jun. 18, 2008 Communication including Partial European Search Report in connection with European Patent Application No. 07 01 4859.8.

Sep. 19, 2008 Final Office Action issued in connection with U.S. Appl. No. 09/460,216.

Jul. 9, 2008 Office Action issued in connection with U.S. Appl. No. 11/258,963.

Jan. 9, 2008 Final Office Action issued in connection with U.S. Appl. No. 11/258,963.

May 29, 2008 Office Action issued in connection with U.S. Appl. No. 11/259,540.

Nov. 19, 2007 Final Office Action issued in connection with U.S. Appl. No. 09/904,356.

Apr. 9, 2008 Office Action issued in connection with U.S. Appl. No. 11/451,707.

Nov. 2, 2007 Office Action issued in connection with U.S. Appl. No. 11/805,573.

Sep. 21, 2007 Notice of Allowability issued in connection with U.S. Appl. No. 11/544,346, now U.S. Appl. No. 7,345,153.

Mar. 11, 2008 Office Action issued in connection with U.S Appl. No. 09/888,938.

May 31, 2007 Office Action issued in connection with U.S. Appl. No. 09/888,938.

Oct. 4, 2007 Office Action issued in connection with U.S. Appl. No. 11/175,815.

Nov. 16, 2007 Office Action issued in connection with U.S. Appl. No. 09/460,216.

Sep. 12, 2007 Final Office Action issued in connection with U.S. Appl. No. 11/400,497.

Apr. 3, 2008 Office Action issued in connection with U.S. Appl. No. 11/520,556.

Jan. 9, 2008 Office Action issued in connection with U.S. Appl. No. 11/259,540.

May 22, 2008 Office Action issued in connection with U.S. Appl. No. 11/491,330.

Aug. 5, 2008 Final Office Action issued in connection with U.S. Appl. No. 11/175,815.

Aug. 19, 2008 Office Action issued in connection with U.S. Appl. No. 11/804,746.

Aug. 21, 2008 Office Action issued in connection with U.S. Appl. No. 09/904,356.

Sep. 11, 2008 Office Action issued in connection with U.S. Appl. No. 11/805,573.

Apr. 9, 2008 Office Action issued in connection with U.S. Appl. No. 11/316,078.

May 14, 2008 Office Action issued in connection with U.S. Appl. No. 11/400,497.

Notification of Transmittal of the International Search Report and the Written Opinion of the International Searching Authority, or the Declaration issued Jul. 25, 2008 in connection with PCT International Application No. PCT/US06/28565.

Notification of Transmittal of the International Search Report and the Written Opinion of the International Searching Authority, or the Declaration issued Aug. 15, 2008 in connection with PCT International Application No. PCT/US08/05564.

May 15, 2008 Office Action issued in connection with U.S. Appl. No. 11/581,945.

Sep. 16, 2008 Communication including a May 29, 2008 Extended European Search report in connection with European Patent Application No. 07014859.8.

Aug. 7, 2009 Advisory Action issued in connection with U.S. Appl. No. 11/581,945.

Notification of Transmittal of the International Search Report and the Written Opinion of the International Searching Authority, or the Declaration issued Aug. 31, 2009, including an International Search Report and Written Opinion, in connection with PCT International Application No. PCT/US09/02654.

Feb. 4, 2009 Final Office Action issued in connection with U.S. Appl. No. 11/316,078.

Mar. 25, 2009 Office Action issued in connection with U.S. Appl. No. 11/175,815.

Extended European Search Report, including a European Search Report and a European Search Opinion, issued Apr. 17, 2009 in connection with European Patent Application No. 08168669.3.

May 1, 2009 Final Office Action issued in connection with U.S. Appl. No. 11/258,963.

Notification of Transmittal of the International Search Report and the Written Opinion of the International Searching Authority, or the Declaration issued May 8, 2009 in connection with PCT International Publication No. PCT/US08/08752.

Prado, J. et al. (2002) "Amprenavir-resistant HIV-1 exhibits lopinavir cross-resistance and reduced replication capacity," AIDS, vol. 16, pp. 1009-1017.

May 13, 2009 Office Action issued in connection with U.S. Appl. No. 09/904,356.

Jun. 23, 2009 Final Office Action issued in connection with U.S. Appl. No. 11/805,573.

Jun. 26, 2009 Final Office Action issued in connection with U.S. Appl. No. 11/581,944.

Jun. 23, 2009 Final Office Action issued in connection with U.S. Appl. No. 09/460,216.

Jun. 26, 2009 Office Action issued in connection with U.S. Appl. No. 11/520,556.

Jul. 14, 2009 Final Office Action issued in connection with U.S. Appl. No. 11/804,746.

Lu et al. (2006) "Rapid emergence of enfuvirtide resistance in HIV-1 infected patients:results of a clonal analysis," J Acquir Defic. Syndr., vol. 43(1), pp. 60-64 (abstract).

Sep. 24, 2009 Office Action issued in connection with U.S. Appl. No. 11/807,349.

Jan. 29, 2010 Office Action issued in connection with U.S. Appl. No. 11/807,349.

Sep. 21, 2009 Final Office Action issued in connection with U.S. Appl. No. 09/888,938.

Oct. 2, 2009 Office Action issued in connection with U.S. Appl. No. 11/894,677.

Bajetto A. et al. (2001) "Chemokines and Their Receptors in the Central Nervous System," Frontiers in Neuroendocrinology, 22, 147-184.

Oct. 5, 2009 Office Action issued in connection with U.S. Appl. No. 11/491,330.

Oct. 6, 2009 Office Action issued in connection with U.S. Appl. No. 11/451,707.

Moore, J.P. (1999) "HIV-1 neutralizing antibodies: How full is the bottle?" Nat. Med. 5(2):142-144.

Montefiori, D.C. (2005) "Neutralizing antibodies take a swipe at HIV in vivo," Nat. Med. 11(6):593-594.

Trkola, A. et al. (2005) "Delay of HIV-1 rebound after cessation of antiretroviral therapy through passives transfer of human neutralizing antibodies," Nat. Med. 11(6):615-622.

Bansal, G.P. (2007) A summary of the workshop on passive immunization using monoclonal antibodies for HIV/AIDS, held at the National Institute of Allergy and Infectious Diseases, Bethesda, Mar. 2006, Biol. 35:367-371.

Oct. 27, 2009 Office Action issued in connection with U.S. Appl. No. 11/316,078.

Keller, M.A. and Stiehm, E.R. (2000) "Passive immunity in prevention and treatment of infectious diseases," Clin. Microbiol Rev., 13(4):602-14.

Notification Concerning Transmittal of International Preliminary Report on Patentability, including an International Preliminary Report on Patentability dated Nov. 3, 2009 and a Written Opinion dated Aug. 15, 2008 in connection with PCT International Application No. PCT/US08/05564.

Dec. 10, 2009 Office Action issued in connection with U.S. Appl. No. 09/904,356.

Dec. 29, 2009 Office Action issued in connection with U.S. Appl. No. 11/894,762.

Tagat, J.R. et al. (2004) "Piperazine-Based CCR5 Antagonists as HIV-1 Inhibitors. IV. Discovery of 1-[(4,6-Dimethyl-5-pyrimidinyl)carbonyl]-4-[4-{2-methoxy-1(R)-4-(trifluoromethyl)phenyl}ethyl-3(S)-methyl-1-piperazinyl]-4-methylpiperidine (Sch-417690/Sch-D), a Potent, Highly Selective, and Orally Bioavailable CCR5 Antagonist," J. Med. Chem. 47:2405-2408.

Extended European Search Report, including a European Search Report and a European Search Opinion, issued Dec. 22, 2009 in connection with European Patent Application No. 08173136.6.

Office Action issued Jan. 26, 2010 in connection with U.S. Appl. No. 11/894,568.

Final Office Action issued Jan. 21, 2010 in connection with U.S. Appl. No. 11/175,815.

Office Action issued Jan. 29, 2010 in connection with U.S. Appl. No. 11/807,349.

FIGURE 1

| mAb | Mean Fluorescence Intensity | | % Gated | |
|---|---|---|---|---|
| | L1.2-CCR5 | PBMC | L1.2-CCR5 | PBMC |
| mouse IgG1 | 10 | 4 | 1 | 1 |
| 2D7 | 75 | 29 | 92 | 36 |
| PA8 | 48 | 9 | 73 | 3 |
| PA9 | 79 | 5 | 96 | 3 |
| PA10 | 80 | 8 | 96 | 5 |
| PA11 | 107 | 8 | 96 | 10 |
| PA12 | 115 | 8 | 96 | 8 |
| PA14 | 81 | 14 | 96 | 22 |

FIGURE 2

| INHIBITOR COMBINATION | CONCENTRATION RATIO | ASSAY | COMBINATION INDEX | |
|---|---|---|---|---|
| | | | 90% Inhibition | 50% Inhibition |
| PA12:2D7 | 10:1 | Entry | 0.043 | 0.291 |
| | 2:1 | Fusion | 0.017 | 0.019 |
| | 10:1 | Fusion | 0.087 | 0.067 |
| | 50:1 | Fusion | 0.158 | 0.046 |
| PA12:PA14 | 10:1 | Entry | 0.437 | 0.535 |
| | 10:1 | Fusion | 0.22 | 0.263 |
| PA14:2D7 | 1:1 | Entry | 2.85 | 1.85 |
| | 1:1 | Fusion | 1.34 | 1.74 |
| PA12:PA11 | 1:1 | Entry | 0.707 | 0.641 |
| PA12:RANTES | 1000:1 | Fusion | 0.331 | 0.156 |
| PA14:RANTES | 100:1 | Fusion | 1.6 | 1.37 |
| 2D7:RANTES | 100:1 | Fusion | 0.972 | 0.962 |
| PA12:CD4-IgG2 | 10:1 | Fusion | 0.3 | 0.31 |
| PA14:CD4-IgG2 | 1:1 | Fusion | 0.957 | 0.566 |
| 2D7:CD4-IgG2 | 1:1 | Fusion | 1.127 | 0.302 |

FIGURE 3

| | Epitopes | IC$_{50}$ values (µg/ml) | | | |
|---|---|---|---|---|---|
| | | cell-cell fusion inhibition | viral entry inhibition | gp120-binding inhibition | calcium flux inhibition |
| PA8 | Nt | - | - | - | - |
| PA9 | Nt/ECL2 | - | - | 0.24 | - |
| PA10 | Nt/ECL2 | - | - | 0.13 | - |
| PA11 | Nt | 25.5 | - | 0.33 | - |
| PA12 | Nt | 10.0 | - | 0.24 | - |
| PA14 | Nt/ECL2 | 1.7 | .024 | 1.58 | 4.5 |
| 2D7 | ECL2 | 1.6 | .026 | 1.38 | 6.4 |

Figure 8

```
                    30                                          60
TCTAGACCACCATGAAGTTGCCTGTTAGGCTGTTGGTGCTGATGTTCTGGATTCCTGCTT
          M  K  L  P  V  R  L  L  V  L  M  F  W  I  P  A
                    90                                         120
CCAGCAGTGATATTGTGATGACCCAATCTCCACTCTCCCTGCCTGTCACTCCTGGAGAGC
 S  S  S  D  I  V  M  T  Q  S  P  L  S  L  P  V  T  P  G  E
                   150                                         180
CAGCCTCCATCTCTTGCAGATCTAGTCAGCGCCTTCTGAGCAGTTATGGACATACCTATT
 P  A  S  I  S  C  R  S  S  Q  R  L  L  S  S  Y  G  H  T  Y
                   210                                         240
TACATTGGTACCTACAGAAGCCAGGCCAGTCTCCACAGCTCCTGATCTACGAAGTTTCCA
 L  H  W  Y  L  Q  K  P  G  Q  S  P  Q  L  L  I  Y  E  V  S
                   270                                         300
ACCGATTTTCTGGGGTCCCAGACAGGTTCAGTGGCAGTGGGTCAGGGACAGATTTCACAC
 N  R  F  S  G  V  P  D  R  F  S  G  S  G  S  G  T  D  F  T
                   330                                         360
TTAAGATCAGTAGAGTGGAGGCTGAGGATGTGGGAGTTTATTACTGCTCTCAAAGTACAC
 L  K  I  S  R  V  E  A  E  D  V  G  V  Y  Y  C  S  Q  S  T
                   390                                         420
ATGTTCCTCTCACGTTCGGACAGGGGACCAAGGTGGAAATAAAACGTAAGTAGTCTTCTC
 H  V  P  L  T  F  G  Q  G  T  K  V  E  I  K
     429
AACTCTAGA
```

Figure 9

```
                         30                                              59
ACGCGTCCACCATGGAATGGAGCGGAGTCTTTATCTTTCTCCTGTCAGTAACTGCAGGT
             M  E  W  S  G  V  F  I  F  L  L  S  V  T  A  G 89                                        118
GTCCACTCCGAGGTGCAGCTGGTGGAGTCTGGTGGAGGCTTGGTAAAGCCTGGAGGTTC
 V  H  S  E  V  Q  L  V  E  S  G  G  G  L  V  K  P  G  G  S 148                                              177
CCTTAGACTCTCCTGTGCAGCCTCTGGTTACACTTTCAGTAACTATTGGATCGGATGGG
 L  R  L  S  C  A  A  S  G  Y  T  F  S  N  Y  W  I  G  W 207                                           236
TCCGCCAGGCTCCAGGCAAAGGGCTGGAGTGGATTGGCGATATCTACCCTGGAGGGAAC
 V  R  Q  A  P  G  K  G  L  E  W  I  G  D  I  Y  P  G  G  N 266                                           295
TACATCAGGAACAATGAGAAGTTCAAGGACAAGACCACCCTGTCAGCAGATACTTCCAA
 Y  I  R  N  N  E  K  F  K  D  K  T  T  L  S  A  D  T  S  K 325                                                354
GAACACAGCCTATCTGCAAATGAACAGCCTGAAAACCGAGGACACAGCCGTGTATTACT
 N  T  A  Y  L  Q  M  N  S  L  K  T  E  D  T  A  V  Y  Y 384                                           413
GTGGAAGCAGCTTCGGTAGTAACTACGTGTTCGCCTGGTTTACTTACTGGGGCCAAGGG
 C  G  S  S  F  G  S  N  Y  V  F  A  W  F  T  Y  W  G  Q  G 443         457
ACTCTGGTCACAGTCTCCTCAGGTGAGTCCTTAAAACCTCTAGA
 T  L  V  T  V  S  S
```

Figure 10

```
                    30                                          60
TCTAGACCACCATGGAATGGAGCGGGGTCTTTATCTTTCTCCTGTCAGTAACTGCAGGTG
           M  E  W  S  G  V  F  I  F  L  L  S  V  T  A  G 90                                    120
TCCACTCCCAGGTCCAACTGGTGCAGTCTGGACCTGATGTGAAAAAGCCTGGGACTTCAA
 V  H  S  Q  V  Q  L  V  Q  S  G  P  D  V  K  K  P  G  T  S 150                                    180
TGAAGATGTCCTGCAAGACGTCTGGATACACCTTCAGTAACTATTGGATCGGATGGGTTA
 M  K  M  S  C  K  T  S  G  Y  T  F  S  N  Y  W  I  G  W  V 210                                    240
GGCAGGCGCCTGGACAAGGCCTTGAGTGGATTGGAGATATTTACCCTGGAGGGAACTATA
 R  Q  A  P  G  Q  G  L  E  W  I  G  D  I  Y  P  G  G  N  Y 270                                    300
TCAGGAACAATGAGAAGTTCAAGGACAAGACCACACTGACGGCAGACACATCGACCAGCA
 I  R  N  N  E  K  F  K  D  K  T  T  L  T  A  D  T  S  T  S 330                                    360
CGGCCTACATGCAACTTGGCAGCCTGAGATCTGAAGACACTGCCGTCTATTACTGTGGAA
 T  A  Y  M  Q  L  G  S  L  R  S  E  D  T  A  V  Y  Y  C  G 390                                    420
GCAGCTTCGGTAGTAACTACGTGTTCGCCTGGTTTACTTACTGGGGCCAAGGGACTCTGG
 S  S  F  G  S  N  Y  V  F  A  W  F  T  Y  W  G  Q  G  T  L 450      457
TCACAGTCTCCTCAGGTGAGTCCTTAAAACCTCTAGA
 V  T  V  S  S
```

Figure 13

No Depletion of Lymphocytes

| | Percent of circulating lymphocytes* | | |
|---|---|---|---|
| | CD4+ cells | CD8+ cells | human cells |
| PRO 140 treated animals | 8.9 | 8.3 | 34 |
| untreated animals | 0.7 | 4.8 | 19 |

*Cohort mean values measured at Day 30 (9 days post-treatment)

Figure 14

Humanized PRO 140 Potently Blocks CCR5-mediated HIV-1 Cell-Cell Fusion

| PRO 140 antibody | number of assays | Median Inhibitory Conc., µg/mL | |
|---|---|---|---|
| | | IC50 | IC90 |
| murine | 6 | 0.99 | 5.90 |
| humanized PRO 140 #1 | 6 | 2.55 | 14.01 |
| *humanized PRO 140 #2* | 6 | *2.24* | *8.55* |

Figure 15

Humanized PRO 140 Mediates Potent, Subtype-Independent Inhibition of HIV-1

| | number of replicate assays per virus | median $IC_{90}$, µg/mL virus (genetic subtype) | | | | |
|---|---|---|---|---|---|---|
| | | JR-FL (B) | Case C 1/85 (B) | DJ258 (A) | DU151 (C) | overall |
| murine PRO 140 | ≥9 | 2.1 | 3.7 | 9.7 | 1.6 | 2.9 |
| humanized PRO 140 #1 | ≥9 | 2.9 | 7.4 | 15 | 14 | 11 |
| humanized PRO 140 #2 | 8 | 2.4 | 3.9 | 3.2 | 4.7 | 3.6 |

ANTI-CCR5 ANTIBODY

This application is a continuation of application U.S. Ser. No. 10/371,483, filed Feb. 21, 2003, now U.S. Pat. No. 7,122,185, which is a continuation-in-part of and claims benefit of U.S. Provisional Application No. 60/358,886, filed Feb. 22, 2002, the contents of which are hereby incorporated by reference into this application.

Throughout this application, various publications are referenced by Arabic numerals. Full citations for these publications may be found at the end of the specification immediately preceding the claims. The disclosure of these publications is hereby incorporated by reference into this application to describe more fully the art to which this invention pertains.

BACKGROUND OF THE INVENTION

Human immunodeficiency virus type 1 (HIV-1) induces viral-to-cell membrane fusion to gain entry into target cells (8, 15, 66). The first high-affinity interaction between the virion and the cell surface is the binding of the viral surface glycoprotein gp120 to the CD4 antigen (13, 30, 41, 42). This in turn induces conformational changes in gp120, which enable it to interact with one of several chemokine receptors (4, 5, 21, 36). The CC-chemokine receptor CCR5 is the major co-receptor for macrophage-tropic (R5) strains, and plays a crucial role in the sexual transmission of HIV-1 (4, 5, 21, 36). T cell line-tropic (X4) viruses use CXCR4 to enter target cells, and usually, but not always, emerge late in disease progression or as a consequence of virus propagation in tissue culture (4, 5, 21, 36). Some primary HIV-1 isolates are dual-tropic (R5X4) since they can use both co-receptors, though not always with the same efficiency (11, 57). Mutagenesis studies coupled with the resolution of the gp120 core crystal structure demonstrated that the co-receptor-binding site on gp120 comprises several conserved residues (32, 53, 65).

It has been demonstrated that tyrosines and negatively charged residues in the amino-terminal domain (Nt) of CCR5 are essential for gp120 binding to the co-receptor, and for HIV-1 fusion and entry (6, 18, 20, 22, 28, 31, 52, 54). Residues in the extracellular loops (ECL) 1-3 of CCR5 were dispensable for co-receptor function, yet the CCR5 inter-domain configuration had to be maintained for optimal viral fusion and entry (24). This led to the conclusion either that gp120 forms interactions with a diffuse surface on the ECLs, or that the Nt is maintained in a functional conformation by bonds with residues in the ECLs. Studies with chimeric co-receptors and anti-CCR5 monoclonal antibodies have also shown the importance of the extracellular loops for viral entry (5, 54, 64).

Molecules that specifically bind to CCR5 and CXCR4 and block interactions with their ligands are a powerful tool to further probe the structure/function relationships of the co-receptors. Characterizing such compounds could also assist in designing effective therapeutic agents that target co-receptor-mediated steps of viral entry. Inhibitors of CCR5 or CXCR4 co-receptor function identified to date are diverse in nature and include small molecules, peptides, chemokines and their derivatives, and monoclonal antibodies (mAbs). The mechanisms of action of the small molecules that block entry by interfering with CXCR4 co-receptor function are not well understood (17, 49, 55, 68). One such inhibitor, the anionic small molecule AMD3100, depends on residues in ECL2 and the fourth trans-membrane (TM) domain of CXCR4 to inhibit viral entry, but it is not clear whether it does so by disrupting gp120 binding to CXCR4 or post-binding steps leading to membrane fusion (16, 34, 55). To date, no small molecules have been reported that specifically block CCR5-mediated HIV-1 entry. Inhibition of HIV-1 entry by chemokines is mediated by at least two distinct mechanisms: blockage of the gp120/co-receptor interaction and internalization of the chemokine/receptor complex (3, 26, 59, 63). The variant AOP-RANTES also inhibits recycling of CCR5 to the cell surface (40, 56). Variants such as RANTES 9-68 and Met-RANTES only prevent the gp120/CCR5 interaction and do not down-regulate CCR5 (67). SDF-1 variants presumably act through a similar mechanism to block viral entry mediated by CXCR4 (12, 27, 39). Only one anti-CXCR4 mAb, 12G5, has been characterized for its anti-viral properties. The efficiency of 12G5 inhibition of viral entry has been reported to be both cell- and isolate-dependent (43, 58). This mAb binds to the ECL2 of CXCR4, but the mechanism by which it inhibits entry is unknown (7). Few of the anti-CCR5 mAbs characterized to date efficiently prevent HIV-1 entry (28, 64). Interestingly, mAbs whose epitopes lie in the Nt domain of CCR5, which contains the gp120-binding site, inhibit viral fusion and entry less efficiently than mAb 2D7, whose epitope lies in ECL2. 2D7 also antagonizes CC-chemokine activity (64).

A panel of six murine mAbs, designated PA8, PA9, PA10, PA11, PA12 and PA14 have been isolated and characterized. All six mAbs specifically bound to CCR5$^+$ cells but with different efficiencies that were cell type-dependent. Epitope mapping studies identified the residues that are important for mAb binding and also revealed information about the folding and interactions of the CCR5 extracellular domains. All mAbs inhibited HIV-1 fusion and entry, but there was no correlation between the ability of a mAb to inhibit fusion and entry and its ability to inhibit binding of gp120/sCD4 to CCR5$^+$ cells.

SUMMARY OF THE INVENTION

This invention provides an anti-CCR5 antibody which comprises (i) two light chains, each light chain comprising the expression product of a plasmid designated pVK:Hu-PRO140-VK (ATCC Deposit Designation PTA-4097), and (ii) two heavy chains, each heavy chain comprising the expression product of either a plasmid designated pVg1:Hu-PRO140 HG2-VH (ATCC Deposit Designation PTA-4098) or a plasmid designated pVg1:HuPRO140 (mut B+D+I)-VH (ATCC Deposit Designation PTA-4099), or a fragment of such antibody, which binds to CCR5 on the surface of a human cell.

This invention also provides an anti-CCR5 antibody comprising two light chains, each chain comprising consecutive amino acids, the amino acid sequence of which is set forth in SEQ ID NO:6, and two heavy chains, each heavy chain comprising consecutive amino acids, the amino acid sequence of which is set forth in SEQ ID NO:9.

This invention also provides an anti-CCR5 antibody comprising two light chains, each chain comprising consecutive amino acids, the amino acid sequence of which is set forth in SEQ ID NO:6, and two heavy chains, each heavy chain comprising consecutive amino acids, the amino acid sequence of which is set forth in SEQ ID NO:12.

This invention also provides an isolated nucleic acid encoding a polypeptide comprising consecutive amino acids, the amino acid sequence of which is set forth in SEQ ID NO:6. In the subject embodiment, the nucleic acid comprises the sequence set forth in SEQ ID NO:5.

This invention also provides an isolated nucleic acid encoding a polypeptide comprising consecutive amino acids, the amino acid sequence of which is set forth in SEQ ID NO:9. In the subject embodiment, the nucleic acid comprises the sequence set forth in SEQ ID NO:8.

This invention also provides an isolated nucleic acid encoding a polypeptide comprising consecutive amino acids, the amino acid sequence of which is set forth in SEQ ID NO:12. In the subject embodiment, the nucleic acid comprises the sequence set forth in SEQ ID NO:11.

This invention also provides a composition comprising at least one anti-CCR5 antibody, or a fragment thereof, as described above, together with a carrier.

This invention also provides a composition comprising the anti-CCR5 antibody, or a fragment thereof, having attached thereto a material such as a radioisotope, a toxin, polyethylene glycol, a cytotoxic agent and/or a detectable label.

This invention also provides a method of inhibiting infection of a CD4+ cell which comprises contacting the CD4+ cell with an antibody which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099), or a fragment of such antibody which binds to CCR5 on the surface of a CD4+ cell, in an amount and under conditions such that fusion of HIV-1 or an HIV-1-infected cell to the CD4+ cell is inhibited, thereby inhibiting HIV-1 infection of the CD4+ cell.

This invention also provides a method of treating a subject afflicted with HIV-1 which comprises administering to the subject an effective HIV-1 treating dosage of an anti-CCR5 antibody comprising (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099), or a fragment of such antibody, which binds to CCR5 on the surface of a human cell, under conditions effective to treat the HIV-1-infected subject.

This invention also provides a method of preventing a subject from contracting an HIV-1 infection which comprises administering to the subject an effective HIV-1 infection-preventing dosage amount of an anti-CCR5 antibody comprising (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099), or a fragment of such antibody, which binds to CCR5 on the surface of a human cell, under conditions effective to prevent the HIV-1, infection in the subject.

This invention also provides an anti-CCR5 antibody conjugate comprising an anti-CCR5 antibody which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099), or a fragment of such antibody which binds to CCR5 on the surface of a human cell, conjugated to at least one polymer.

This invention also provides a method of inhibiting infection of a CCR5+ cell by HIV-1 comprising administering to a subject at risk of HIV-1 infection the above-described conjugate in an amount and under conditions effective to inhibit infection of CCR5+ cells of the subject by HIV-1.

This invention also provides a method of treating an HIV-1 infection in a subject comprising administering the above-described conjugate to an HIV-1-infected subject in an amount and under conditions effective to treat the subject's HIV-1 infection.

This invention also provides a transformed host cell comprising at least two vectors, at least one vector comprising a nucleic acid sequence encoding heavy chains of an anti-CCR5 antibody, and at least one vector comprising a nucleic acid sequence encoding light chains of the anti-CCR5 antibody, wherein the anti-CCR5 antibody comprises two heavy chains having the amino acid sequence set forth in SEQ ID NO:9, and two light chains having the amino acid sequence set forth in SEQ ID NO:6.

This invention also provides a transformed host cell comprising at least two vectors, at least one vector comprising a nucleic acid sequence encoding heavy chains of an anti-CCR5 antibody, and at least one vector comprising a nucleic acid sequence encoding light chains of the anti-CCR5 antibody, wherein the anti-CCR5 antibody comprises two heavy chains having the amino acid sequence set forth in SEQ ID NO:12 and two light chains having the amino acid sequence set forth in SEQ ID NO:6.

This invention also provides a vector comprising a nucleic acid sequence encoding a heavy chain of an anti-CCR5 antibody, wherein the heavy chain comprises the amino acid sequence set forth in SEQ ID NO:9.

This invention also provides a vector comprising a nucleic acid sequence encoding a heavy chain of an anti-CCR5 antibody, wherein the heavy chain comprises the amino acid sequence set forth in SEQ ID NO:12.

This invention also provides a process for producing an anti-CCR5 antibody which comprises culturing a host cell containing therein (i) a plasmid designated pVK:HuPRO140-VK (ATCC Deposit Designation PTA-4097), and (ii) either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099) under conditions permitting the production of an antibody comprising two light chains encoded by the plasmid designated pVK:HuPRO140-VK (ATCC Deposit Designation PTA-4097) and two heavy chains encoded either by the plasmid designated pVg1:HuPRO140 HG2-VH (ATCC Deposit Designation PTA-4098) or by the plasmid designated pVg1:HuPRO140 (mut B+D+I)-VH (ATCC Deposit Designation PTA-4099), so as to thereby produce an anti-CCR5 antibody.

This invention also provides a process for producing an anti-CCR5 antibody which comprises a) transforming a host cell with (i) a plasmid designated pVK:HuPRO140-VK (ATCC Deposit Designation PTA-4097) and (ii) either a plasmid designated pVg1:HuPRO140 HG2-VH (ATCC Deposit Designation PTA-4098) or a plasmid designated pVg1:HuPRO140 (mut B+D+I)-VH (ATCC Deposit Designation PTA-4099), and b) culturing the transformed host cell under conditions permitting production of an antibody comprising two light chains encoded by the plasmid designated pVK:HuPRO140-VK (ATCC Deposit Designation PTA-4097) and two heavy chains encoded either by the plasmid designated pVg1:HuPRO140 HG2-VH (ATCC Deposit Designation PTA-4098) or by the plasmid designated pVg1HuPRO140 (mut B+D+I)-VH (ATCC Deposit Designation PTA-4099), so as to thereby produce an anti-CCR5 antibody.

This invention also provides a kit for use in a process of producing an anti-CCR5 antibody. The kit comprises a) a vector comprising a nucleic acid sequence encoding a light chain of an anti-CCR5 antibody, wherein the light chain comprises the amino acid sequence set forth in SEQ ID NO:6, and b) a vector comprising a nucleic acid sequence encoding a heavy chain of an anti-CCR5 antibody, wherein the heavy chain comprises the amino acid sequence set forth in SEQ ID NO:9, or a vector comprising a nucleic acid sequence encoding a heavy chain of an anti-CCR5 antibody, wherein the heavy chain comprises the amino acid sequence set forth in SEQ ID NO:12.

BRIEF DESCRIPTION OF THE FIGURES

FIG. 1:

Binding of Anti-CCR5 Monoclonal Antibodies to CCR5$^+$ Cells:

Flow cytometry was used to detect CCR5 protein expression on the surface of L1.2-CCR5$^+$ cells and freshly isolated, PHA/IL-2-stimulated PBMC. Cells were incubated with saturating concentrations of each mAb, which were detected with a PE-labeled anti-mouse IgG reporter antibody. Results from a representative experiment are shown. Results for each mAb are expressed both in mean fluorescence intensities (m.f.i.) and in % gated cells. Since PA8-PA12 and PA14 are all of the IgG1 subclass, their m.f.i. are directly comparable. 2D7 is an IgG2a.

Figure 7:
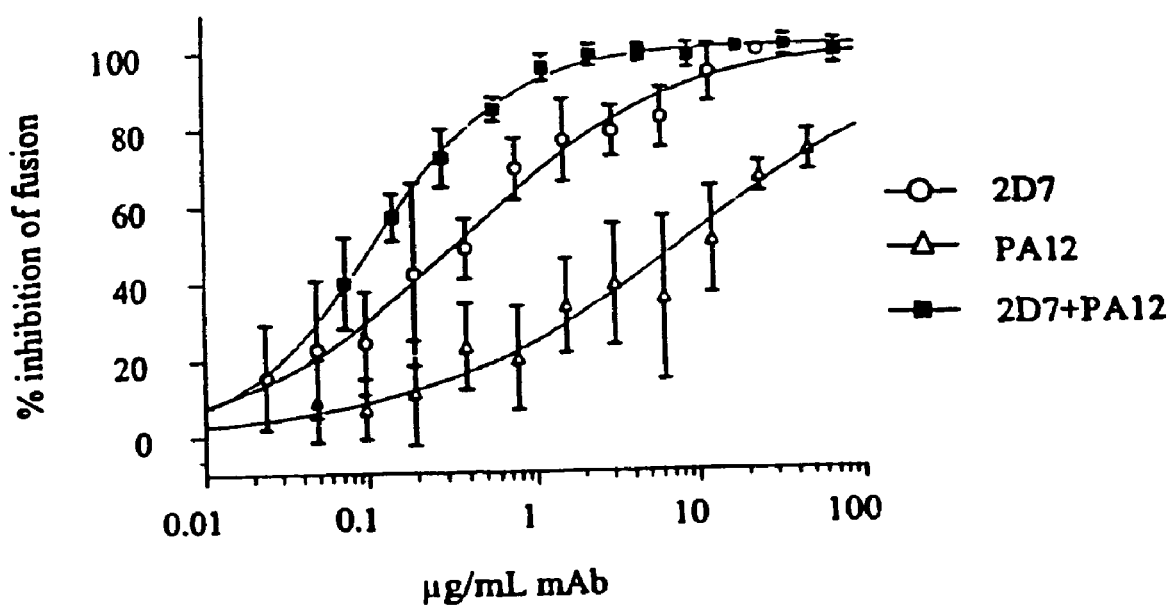
Figure 11:
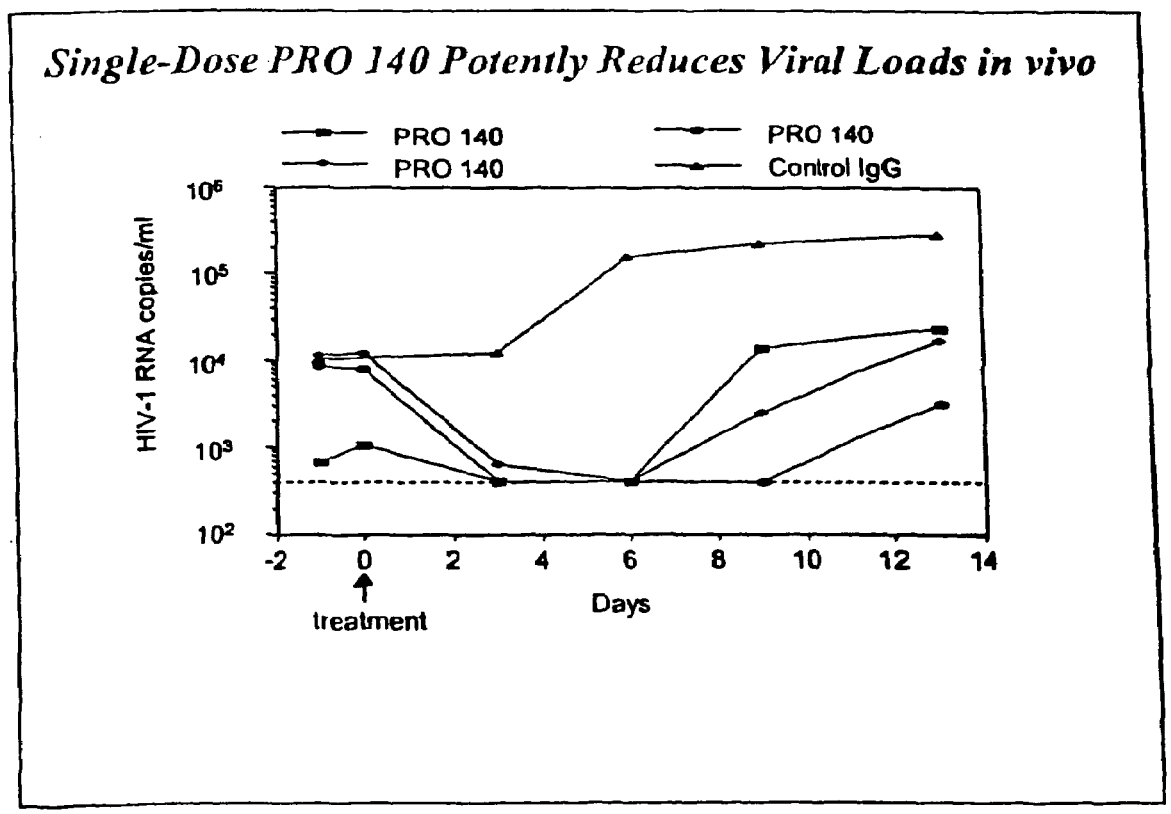
Figure 12:
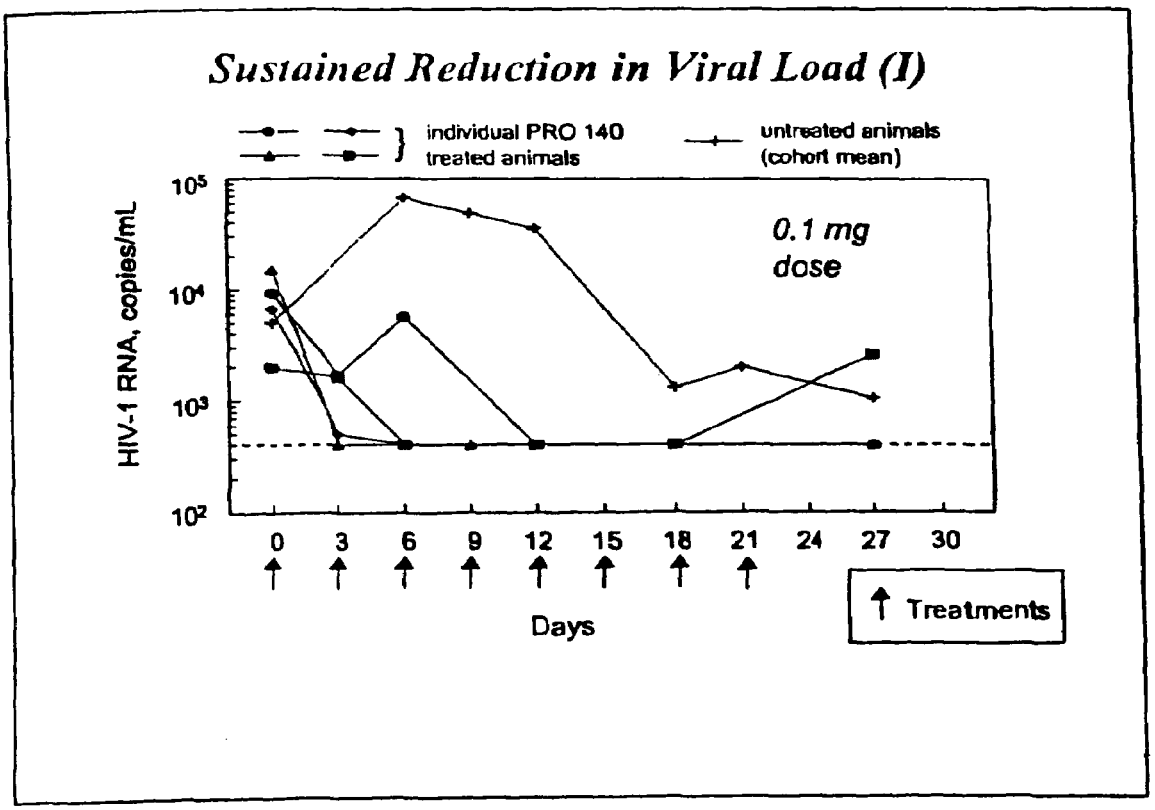

FIG. 2:

CI Values for Different Combinations of mAbs and Viral Inhibitors:

Experiments like those described in the legend of FIG. 7 were performed for different combinations of viral entry inhibitors. Anti-CCR5 mAbs were tested in combination with each other, CC-chemokines, and CD4-IgG2, which inhibits HIV-1 attachment to target cells. The PA11 and PA12 concentration range was 0-250 µg/ml; the 2D7 and PA14 concentration range was 0-25 µg/ml; the RANTES concentration range was 0-250 ng/ml; the CD4-IgG2 concentration range was 0-25 µg/ml. The concentrations of single-agents or their mixtures required to produce 50% and 90% inhibition of fusion or entry were quantitatively compared in a term known as the Combination Index (CI).

FIG. 3:

$IC_{50}$ Values for Inhibition of Cell-Cell Fusion, Viral Entry and gp120/sCD4 Binding by Anti-CCR5 mAbs:

For comparative purposes we have summarized the $IC_{50}$ values obtained in the different assays that the anti-CCR5 mAbs were tested in. $IC_{50}$ values were only calculated for mAbs that could inhibit >90% of fusion, entry or binding.

FIG. 4:

Epitope Mapping of Anti-CCR5 mAbs:

A two color staining protocol was used to assess binding of mAbs to mutant CCR5 proteins, tagged at the C-terminus with the HA peptide. HeLa cells expressing CCR5 point mutants were incubated with saturating concentrations of each mAb followed by detection with a PE-labeled anti-mouse IgG. Cell surface co-receptor expression was measured by double-staining of the cells with a FITC labeled anti-HA mAb. The four grids correspond to the four extracellular domains of CCR5. The first row of every grid indicates the amino acid sequence of the corresponding CCR5 extracellular domain (SEQ ID NOS: 1-4). Binding of anti-CCR5 mAbs to the alanine mutant of each residue is expressed as a percentage of binding to wild-type CCR5, as described in Materials and Methods.

FIG. 5:

Inhibition of Calcium Mobilization into CCR5$^+$ Cells by Anti-CCR5 mAbs:

L1.2-CCR5$^+$ cells were loaded with Indo-1AM and stimulated sequentially with an anti-CCR5 mAb or PBS, followed with RANTES (a). Fluorescence changes were measured with a spectrofluorometer and the tracings are from a representative experiment. Calcium flux inhibition by PA14 and 2D7 was tested for a wide range of mAb concentrations (b). Results are plotted as % inhibition of calcium influx=[1−(relative fluorescence in the presence of mAb÷relative fluorescence in the absence of mAb)]×100%, and are means of values from three independent experiments.

FIG. 6:

Inhibition of CCR5 Co-Receptor Function by Anti-CCR5 mAbs:

Inhibition of cell-cell fusion by anti-CCR5 mAbs was tested in the RET assay (a). 0-250 µg/ml of PA8-PA12, or 0-25 µg/ml of PA14 or 2D7, were added to a mix of HeLa-Env$_{JR-FL}$$^+$ and PM1 cells, labeled with F18 and R18 respectively. Fluorescence RET was measured after 4 h of incubation. Results are mean values from three independent experiments and are expressed as % inhibition of fusion= [1−(% RET in the presence of mAb÷% RET in the absence of mAb)]×100%. Inhibition of HIV-1 entry by anti-CCR5 mAbs was tested in a single round of replication luciferase based entry assay (b). U87-CD4$^+$CCR5$^+$ cells were infected with NLluc$^+$env$^−$ reporter virus carrying the JR-FL envelope in the presence of 0-250 µg/ml of PA8-PA12, or 0-25 µg/ml PA14 or 2D7. Luciferase activity (relative light units, r.l.u.) was measured in cell lysates 72 h post-infection. Results are from a representative experiment and are expressed as % inhibition of entry=[1−(r.l.u. in the presence of mAb÷r.l.u. in the absence of mAb)]×100%. Binding of biotinylated [b] gp120, sCD4 and b-gp120-CD4 complexes to L1.2-CCR5$^+$ cells (c). Strong binding is observed when gp120 derived from the R5 virus HIV-1$_{JR-FL}$ is complexed with an equimolar amount of sCD4. No binding is observed in the absence of sCD4 or for gp120 derived from the X4 virus HIV-1$_{LAI}$. Background binding to CCR5-L1.2 cells has been subtracted from all curves. Inhibition of gp120/sCD4 binding to L1.2-CCR5$^+$ cells was tested in the presence of varying concentrations of each antibody (d). Cells were pre-incubated in 96-well plates with an anti-CCR5 mAb followed by an incubation with a saturating concentration of biotinylated gp120/sCD4. Finally, binding of PE-labeled streptavidin to cells was measured using a fluorescence plate reader. Results are from a representative experiment and are expressed as % inhibition of gp120/sCD4 binding=[1−(m.f.i. in the presence of mAb÷m.f.i. in the absence of mAb)]×100%.

FIG. 7:

Synergistic Inhibition of Cell-Cell Fusion by PA12 and 2D7:

Dose-response curves were obtained for the mAbs used individually and in combination. 0-50 µg/ml of PA12, 0-25 µg/ml 2D7, or a combination of the two in a 2:1 ratio, were added to a mix of HeLa-Env$_{JR-FL}$$^+$ and PM1 cells, labeled with R18 and F18 respectively. Fluorescence RET was measured after 4 hours of incubation. Results are expressed as % inhibition of fusion and are the means of values from three independent experiments. Data were analyzed using the median effect principle, which can be written $$f=1/[1+(K/c)^m] \qquad (1)$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1. In the present case, K is equal to the $IC_{50}$ value. K and m were determined by curve-fitting the dose-response curves and Equation (1) was rearranged to allow calculation of c for a given f. The best-fit parameters for K and c are 8.8 µg/ml and 0.54 for PA12, 0.36 µg/ml and 0.68 for 2D7, and 0.11 µg/ml and 1.1 for their combination. These curves are plotted and indicate a reasonable goodness-of-fit between experiment and theory.

FIG. 8:

This figure shows the amino acid sequence of the light chain variable region of a humanized version of mouse anti-CCR5 antibody PA14 (SEQ ID NO: 6) and the nucleic acid sequence encoding the same (SEQ ID NO: 5), in accordance with the invention. SEQ ID NO: 7 identifies the region of SEQ ID NO: 5 which codes for the amino acid sequence set forth in SEQ ID NO:6. This light chain variable region is present in the antibodies designated herein as PRO 140 #1 and #2. The complementarity-determining regions ("CDRs") are underlined.

FIG. 9:

This figure shows the amino acid sequence of a first heavy chain variable region of a humanized version of mouse anti-CCR5 antibody PA14 (SEQ ID NO:9), and the nucleic acid sequence encoding the same (SEQ ID NO:8), in accordance with the invention. SEQ ID NO:10 identifies the region of SEQ ID NO:8 that codes for the amino acid sequence set forth in SEQ ID NO:9. This heavy chain variable region is present in the antibody designated herein as PRO 140 #2. The CDRs are underlined.

FIG. 10:

This figure shows the amino acid sequence of a second heavy chain variable region of a humanized version of mouse humanized anti-CCR5 antibody PA14 (SEQ ID NO:12) and the nucleic acid sequence encoding the same (SEQ ID NO:11) in accordance with the invention. SEQ ID NO:13 identifies the region of SEQ ID NO:11 that codes for the amino acid sequence set forth in SEQ ID NO:12. This heavy chain variable region is present in the antibody designated herein as PRO 140 #1. The CDRs are underlined.

FIG. 11:

Single-Dose of Humanized CCR5 Antibody Potently Reduces Viral Loads In Vivo:

SCID mice were reconstituted with normal human PBMC and infected with HIV-1$_{JR-CSF}$. When a viral steady state was reached, the animals were treated with a single 1 milligram i.p. dose of humanized CCR5 antibody (PRO 140) or isotype control antibody and monitored for plasma HIV RNA (Roche Amplicor Assay).

FIG. 12:

Sustained Reduction in Viral Load:

SCID mice were reconstituted with normal human PBMC and infected with HIV-1$_{JR-CSF}$. When a viral steady state was reached, the animals were treated i.p. with 0.1 mg doses of humanized CCR5 antibody (PRO140) every three days and monitored for plasma HIV RNA (Roche Amplicor Assay).

FIG. 13:

Demonstrates that there was no depletion of lymphocytes with the use of the CCR5 antibody (PRO 140) prepared in accordance with the invention.

FIG. 14:

Humanized CCR5 Antibody (PRO140) Potently Blocks CCR5-Mediated HIV-1 Cell-Cell Fusion.

Murine CCR5 antibody was humanized using the method of complementarity-determining region (CDR) grafting and framework substitutions. Humanized CCR5 antibodies (PRO 140 #1 and PRO 140 #2) were expressed in Sp2/0 cells, purified by protein A chromatography and tested for the ability to block replication of HIV-1$_{JR-FL}$ env-mediated membrane fusion as described (Litwin, et al., J, Virol., 70:6437, 1996).

FIG. 15:

Humanized CCR5 Antibody (PRO 140) Mediates Potent, Subtype-Independent Inhibition of HIV-1.

CCR5 Antibodies (Pro 140 #1 and #2) according to the invention were tested for the ability to block replication of wild-type HIV-1 in peripheral blood mononuclear cells (PB-MCs) as described (Trkola et al., J. Virol., 72:396, 1998). The extent of viral replication was measured by assaying the p24 antigen content of 7-day PBMC culture supernatants.

FIG. 16:

This figure provides a map of plasmid pVK-HuPRO140 encoding the light plasmid chain variable region shown in FIG. 8 as well as the human Kappa constant regions as described in Co et al., J. Immunol., 148:1149, 1992.

FIG. 17:

This figure provides a map of plasmid pVg4-HuPRO140 HG2 encoding the heavy chain variable region shown in FIG. 9 as well as the human heavy chain constant regions, CH1, hinge, CH2, and CH3, of human IgG4 as described in Co et al, Supra.

FIG. 18:

This figure provides a map of plasmid pVg4-HuPRO140 (mut B+D+I) encoding the heavy chain variable region shown in FIG. 10 as well as the human heavy chain constant regions, CH1, hinge, CH2, and CH3, of human IgG4 as described in Co et al, Supra.

FIG. 19

Hu PRO140 Blocks HIV-1 But Not RANTES Signaling

PRO140 antibodies according to the invention were tested for the ability to block RANTES-induced calcium mobilization in L1.2-CCR5 cells (Olson, et al., J. Virol., 72:396, 1998). This figure shows that a humanized CCR5 antibody (huPRO140) blocks HIV-1 but not RANTES signaling.

DETAILED DESCRIPTION OF THE INVENTION

Figure 16:
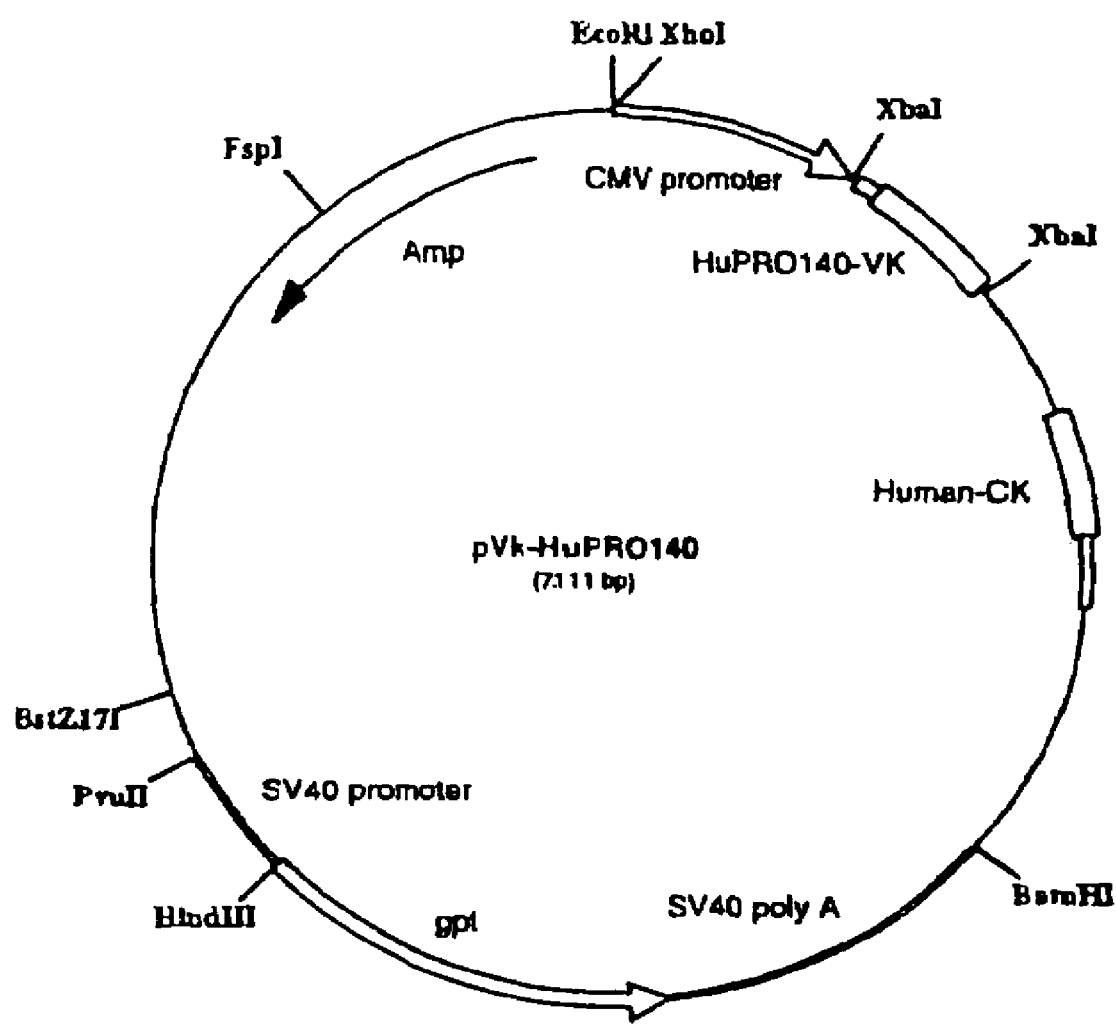
Figure 17:
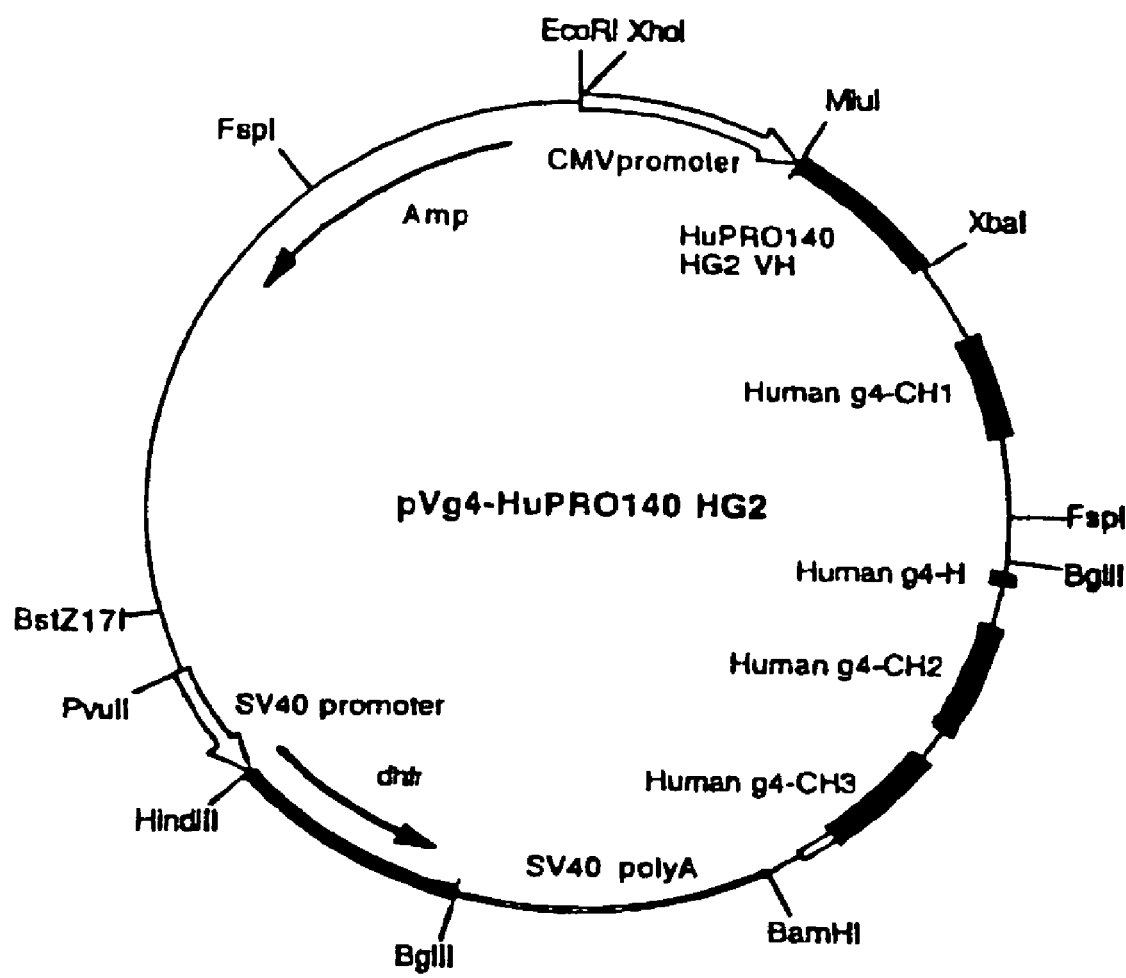
Figure 18:
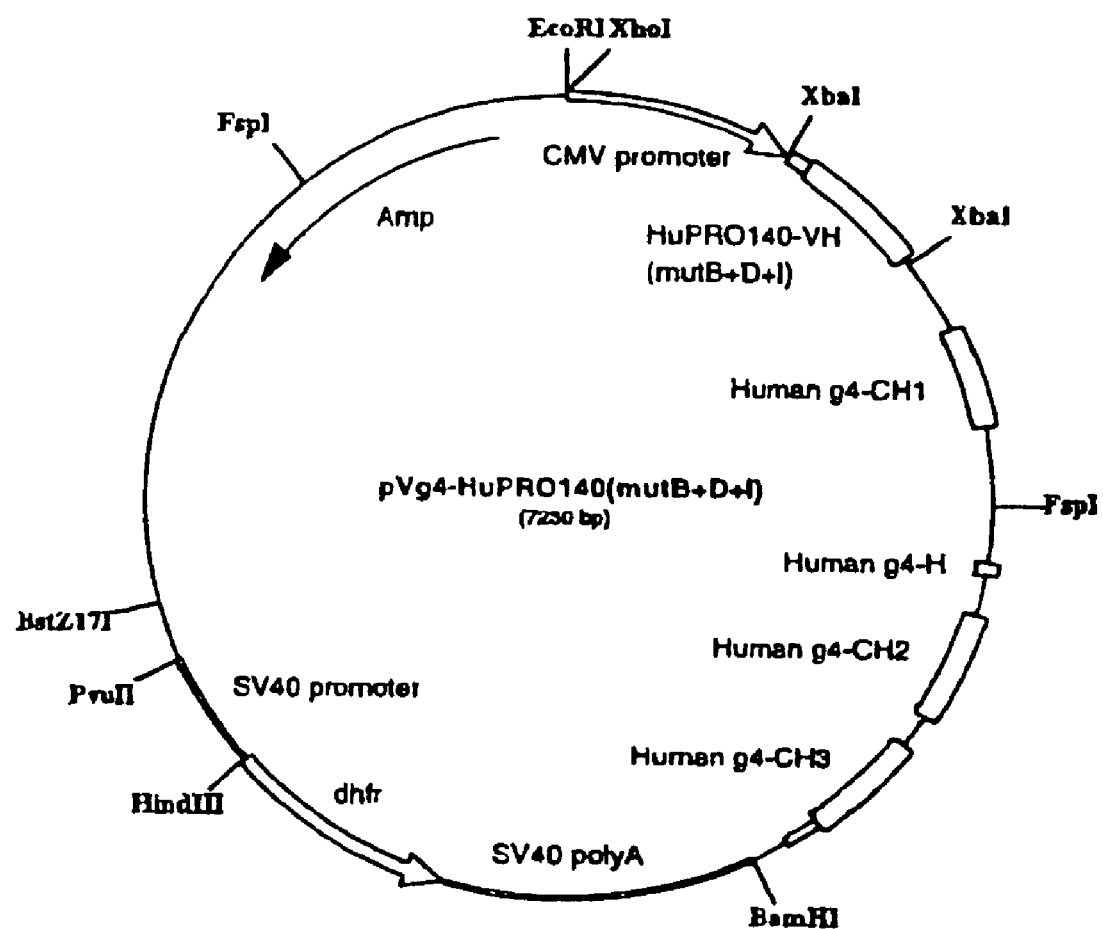

The plasmids designated as HuPRO140-VK, HuPRO140 (mut+B+D+I)-VH, and HuPRO140 HG2-VH, which are referred to in FIGS. 16, 18, and 17 as pVK-HuPRO140, pVg4-HuPRO140 (mut B+D+I) and pVg4-HuPRO140 HG2, respectively, were deposited with the American Type Culture Collection, Manassas, Va., U.S.A. 20108 on Feb. 22, 2002, under ATCC Accession Nos. PTA 4097, PTA 4099 and PTA 4098 respectively. These deposits were made pursuant to the provisions of the Budapest Treaty on the international Recognition of the Deposit of Microorganisms for the Purpose of Patent Procedure (Budapest Treaty).

This invention provides a composition for inhibiting HIV-1 infection comprising at least two compounds in synergistically effective amounts for inhibiting HIV-1 infection, wherein at least one of the compounds prevents with the productive interaction between HIV-1 and an HIV-1 fusion co-receptor.

As used herein, "composition" means a mixture. The compositions include but are not limited to those suitable for oral, rectal, intravaginal, topical, nasal, opthalmic, or parenteral administration to a subject. As used herein, "parenteral" includes but is not limited to subcutaneous, intravenous, intramuscular, or intrasternal injections or infusion techniques.

As used herein, "HIV-1" means the human immunodeficiency virus type-1. HIV-1 includes but is not limited to extracellular virus particles and the forms of HIV-1 found in HIV-1 infected cells.

As used herein, "HIV-1 infection" means the introduction of HIV-1 genetic information into a target cell, such as by fusion of the target cell membrane with HIV-1 or an HIV-1 envelope glycoprotein$^+$ cell. The target cell may be a bodily cell of a subject. In the preferred embodiment, the target cell is a bodily cell from a human subject.

As used herein, "inhibiting HIV-1 infection" means the reduction of the amount of HIV-1 genetic information introduced into a target cell population as compared to the amount that would be introduced without said composition.

As used herein, "compound" means a molecular entity, including but not limited to peptides, polypeptides, and other organic or inorganic molecules and combinations thereof.

As used herein, "synergistically effective" means that the combined effect of the compounds when used in combination is greater than their additive effects when used individually.

As used herein, "productive interaction" means that the interaction of HIV-1 and the HIV-1 co-receptor would lead to the fusion of said HIV-1 or HIV-1 envelope glycoprotein$^+$ cell and the membrane bearing the co-receptor.

As used herein, "prevents the productive interaction" means that the amount of interaction is reduced as compared to the amount that would occur without the compound. The interactions may be prevented by masking or altering interactive regions on the co-receptor or HIV-1 or by altering the expression, aggregation, conformation, or association state of the co-receptor.

As used herein, "HIV-1 fusion co-receptor" means a cellular receptor that mediates fusion between the target cell expressing the receptor and HIV-1 or an HIV-1 envelope glycoprotein$^+$ cell. HIV-1 fusion co-receptors include but are not limited to CCR5, CXCR4 and other chemokine receptors.

This invention also provides a composition which inhibits fusion of HIV-1 or an HIV-1 envelope glycoprotein$^+$ cell to a target cell, comprising at least two compounds in synergistically effective amounts for inhibiting fusion of HIV-1 or an HIV-1 envelope glycoprotein$^+$ cell to a target cell, wherein at least one of the compounds prevents the productive interaction between HIV-1 and an HIV-1 fusion co-receptor.

As used herein, "fusion" means the joining or union of the lipid bilayer membranes found on mammalian cells or viruses such as HIV-1. This process is distinguished from the attachment of HIV-1 to a target cell. Attachment is mediated by the binding of the HIV-1 exterior glycoprotein to the human CD4 receptor, which is not a fusion co-receptor.

As used herein, "inhibits" means that the amount is reduced as compared with the amount that would occur without the composition.

As used herein, "target cell" means a cell capable of being infected by or fusing with HIV-1 or HIV-1 infected cells.

As used herein, "chemokine" means a cytokine that can stimulate leukocyte movement. They may be characterized as either cys-cys or cys-X-cys depending on whether the two amino terminal cysteine residues are immediately adjacent or separated by one amino acid. It includes but is not limited to RANTES, MIP-1α, MIP-1β, SDF-1 or another chemokine which blocks HIV-1 infection.

In one embodiment of the above compositions, the co-receptor is a chemokine receptor. In the preferred embodiment of the above compositions, the chemokine receptor is CCR5 or CXCR4. Several other chemokine and related receptors are known to function as HIV co-receptors including but not limited to CCR2, CCR3, CCR8, STRL33, GPR-15, CX3CR1 and APJ (69).

As used herein, "chemokine receptor" means a member of a homologous family of seven-transmembrane spanning cell surface proteins that bind chemokines.

As used herein, "CCR5" is a chemokine receptor which binds members of the C-C group of chemokines and whose amino acid sequence comprises that provided in Genbank Accession Number 1705896 and related polymorphic variants.

As used herein, "CXCR4" is a chemokine receptor which binds members of the C-X-C group of chemokines and whose amino acid sequence comprises that provided in Genbank Accession Number 400654 and related polymorphic variants.

In one embodiment of the above compositions, at least one of the compounds is a nonpeptidyl molecule. In one embodiment, the nonpeptidyl molecule is the bicyclam compound AMD3100. (16).

As used herein, "nonpeptidyl molecule" means a molecule that does not consist in its entirety of a linear sequence of amino acids linked by peptide bonds. A nonpeptidyl molecule may, however, contain one or more peptide bonds.

In one embodiment of the above compositions, at least one of the compounds is an antibody. In one embodiment, the antibody is a monoclonal antibody. In another embodiment, the antibody is a anti-chemokine receptor antibody. In one embodiment, the antibody is an anti-CXCR4 antibody. In a further embodiment, the anti CXCR4 antibody is 12G5. (43). In a preferred embodiment, the antibody is an anti-CCR5 antibody. The anti-CCR5 antibody includes but is not limited to PA8, PA9, PA10, PA11, PA12, PA14 and 2D7. In this composition the compounds are in an appropriate ratio. The ratio ranges from 1:1 to 1000:1.

The monoclonal antibodies PA8, PA9, PA10, PA11, PA12 and PA14 were deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Dec. 2, 1998 under the following Accession Nos.: ATCC Accession No. HB-12605 (PA8), ATCC Accession No. HB-12606 (PA9), ATCC Accession No. HB-12607 (PA10), ATCC Accession No. HB-12608 (P11), ATCC Accession No. HB-12609 (PA12) ATCC Accession No. HB-12610 (PA14).

In another embodiment of the above compositions, two or more of the compounds are antibodies. In one embodiment of the invention, the antibodies include but are not limited to PA8, PA9, PA10, PA11, PA12, PA14 and 2D7. In this composition the antibodies are in an appropriate ratio. The ratio ranges from 1:1 to 50:1.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof.

Optionally, an antibody can be labeled with a detectable marker. Detectable markers include, for example, radioactive or fluorescent markers. The antibody may be a human or nonhuman antibody. The nonhuman antibody may be humanized by recombinant methods to reduce its immunogenicity in man. Methods for humanizing antibodies are known to those skilled in the art.

As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art.

As used herein, "anti-chemokine receptor antibody" means an antibody which recognizes and binds to an epitope on a chemokine receptor. As used herein, "anti-CCR5 antibody" means a monoclonal antibody which recognizes and binds to an epitope on the CCR5 chemokine receptor.

As used herein, "appropriate ratio" means mass or molar ratios wherein the compounds are synergistically effective.

In one embodiment of the above compositions, at least one compound is a chemokine or chemokine derivative. The chemokines include but are not limited to RANTES, MIP-1α, MIP-1β, SDF-1 or a combination thereof. In this composition, the compounds are in an appropriate ratio. The chemokine derivatives include but are not limited to Met-RANTES, AOP-RANTES, RANTES 9-68, or a combination thereof.

As used herein, "chemokine derivative" means a chemically modified chemokine. The chemical modifications include but are not limited to amino acid substitutions, additions or deletions, non-peptidyl additions or oxidations. One skilled in the art will be able to make such derivatives.

In another embodiment of the above compositions, at least one compound is an antibody and at least one compound is a chemokine or chemokine derivative. In this composition, the compounds are in an appropriate ratio. The ratio ranges from 100:1 to 1000:1.

In another embodiment of the above compositions, at least one compound binds to the gp41 subunit of the HIV-1 envelope glycoprotein. In one embodiment, at least one compound is the T-20 peptide inhibitor of HIV-1 entry (70).

In another embodiment of the above compositions, at least one of the compounds inhibits the attachment of HIV-1 to a target cell. In one embodiment, at least one compound binds CD4. In one embodiment, at least one compound is an HIV-1 envelope glycoprotein. In one embodiment, at least one compound is an anti-CD4 antibody. In one embodiment, at least one compound binds to the HIV-1 envelope glycoprotein. In one embodiment, at least one compound is an antibody to the HIV-1 envelope glycoprotein. In one embodiment, at least one compound is a CD4-based protein. In one embodiment, at least one compound is CD4-IgG2.

In another embodiment of the above compositions, at least one compound is an antibody and at least one compound binds to an HIV-1 envelope glycoprotein. In one embodiment, the compound is a CD4-based protein. In one embodiment, the compound is CD4-IgG2. In this composition, the compounds are in an appropriate ratio. The ratio ranges from 1:1 to 10:1.

As used herein, "attachment" means the process that is mediated by the binding of the HIV-1 envelope glycoprotein to the human CD4 receptor, which is not a fusion co-receptor.

As used herein, "CD4" means the mature, native, membrane-bound CD4 protein comprising a cytoplasmic domain, a hydrophobic transmembrane domain, and an extracellular domain which binds to the HIV-1 gp120 envelope glycoprotein.

As used herein, "HIV-1 envelope glycoprotein" means the HIV-1 encoded protein which comprises the gp120 surface protein, the gp41 transmembrane protein and oligomers and precursors thereof.

As used herein, "CD4-based protein" means any protein comprising at least one sequence of amino acid residues corresponding to that portion of CD4 which is required for CD4 to form a complex with the HIV-1 gp120 envelope glycoprotein.

As used herein, "CD4-IgG2" means a heterotetrameric CD4-human IgG2 fusion protein encoded by the expression vectors deposited under ATCC Accession Numbers 75193 and 75194.

In one embodiment of the above compositions at least one of the compounds comprises a polypeptide which binds to a CCR5 epitope. In one embodiment, the epitope is located in the N-terminus, one of the three extracellular loop regions or a combination thereof. In one embodiment, the epitope is located in the N-terminus. The epitope can comprise N13 and Y15 in the N-terminus. The epitope can comprise comprises Q4 in the N-terminus. In another embodiment, the epitope includes residues in the N-terminus and second extracellular loop. The epitope can comprise D2, Y3, Q4, S7, P8 and N13 in the N-terminus and Y176 and T177 in the second extracellular loop. The epitope can comprise D2, Y3, Q4, P8 and N13 in the N-terminus and Y176 and T177 in the second extracellular loop. The epitope can comprise D2 in the N-terminus and R168 and Y176 in the second extracellular loop. In one embodiment, the epitope is located in the second extra cellular loop. The epitope can comprise Q170 and K171 in the second extracellular loop. The epitope can comprise Q170 and E172 in the second extra cellular loop.

As used herein, the following standard abbreviations are used throughout the specification to indicate specific amino acids:

A=ala=alanine R=arg=arginine
N=asn=asparagine D=asp=aspartic acid
C=cys=cysteine Q=gln=glutamine
E=glu=glutamic acid G=gly=glycine
H=his=histidine I=ile=isoleucine
L=leu=leucine K=lys=lysine
M=met=methionine F=phe=phenylalanine
P=pro=proline S=ser=serine
T=thr=threonine W=trp=tryptophan
Y=tyr=tyrosine V=val=valine As used herein, "polypeptide" means two or more amino acids linked by a peptide bond.

As used herein, "epitope" means a portion of a molecule or molecules that forms a surface for binding antibodies or other compounds. The epitope may comprise contiguous or non-contiguous amino acids, carbohydrate or other nonpeptidyl moities or oligomer-specific surfaces.

As used herein, "N-terminus" means the sequence of amino acids spanning the initiating methionine and the first transmembrane region.

As used herein, "second extra cellular loop" means the sequence of amino acids that span the fourth and fifth transmembrane regions and are presented on the surface.

In one embodiment of the above compositions at least one of the compounds comprises a light chain of an antibody. In another embodiment of the above compositions at least one of the compounds comprises a heavy chain of an antibody. In another embodiment of the above compositions at least one of the compounds comprises the Fab portion of an antibody. In another embodiment of the above compositions at least one of the compounds comprises the variable domain of an antibody. In another embodiment, the antibody is produced as a single polypeptide or "single chain" antibody which comprises the heavy and light chain variable domains genetically linked via an intervening sequence of amino acids. In another embodiment of the above compositions at least one of the compounds comprises one or more CDR portions of an antibody.

As used herein, "heavy chain" means the larger polypeptide of an antibody molecule composed of one variable domain (VH) and three or four constant domains (CH1, CH$_2$, CH3, and CH4), or fragments thereof.

As used herein, "light chain" means the smaller polypeptide of an antibody molecule composed of one variable domain (VL) and one constant domain (CL), or fragments thereof.

As used herein, "Fab" means a monovalent antigen binding fragment of an immunoglobulin that consists of one light chain and part of a heavy chain. It can be obtained by brief papain digestion or by recombinant methods.

As used herein, "F(ab')2 fragment" means a bivalent antigen binding fragment of an immunoglobulin that consists of both light chains and part of both heavy chains. It can be obtained by brief pepsin digestion or recombinant methods.

As used herein, "CDR" or "complementarity determining region" means a highly variable sequence of amino acids in the variable domain of an antibody.

This invention provides the above compositions and a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method of treating a subject afflicted with HIV-1 which comprises administering to the subject an effective dose of the above compositions.

As used herein, "subject" means any animal or artificially modified animal capable of becoming HIV-infected. Artificially modified animals include, but are not limited to, SCID mice with human immune systems. The animals include but are not limited to mice, rats, dogs, guinea pigs, ferrets, rabbits, and primates. In the preferred embodiment, the subject is a human.

As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1.

As used herein, "afflicted with HIV-1" means that the subject has at least one cell which has been infected by HIV-1.

As used herein, "administering" may be effected or performed using any of the methods known to one skilled in the art. The methods may comprise intravenous, intramuscular or subcutaneous means.

The dose of the composition of the invention will vary depending on the subject and upon the particular route of administration used. Dosages can range from 0.1 to 100,000 µg/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming HIV-1 infected. A person of ordinary skill in the art can perform simple titration experiments to determine what amount is required to treat the subject.

This invention provides a method of preventing a subject from contracting HIV-1 which comprises administering to the subject an effective dose of the above compositions.

As used herein, "contracting HIV-1" means becoming infected with HIV-1, whose genetic information replicates in and/or incorporates into the host cells.

This invention provides an anti-CCR5 monoclonal antibody. The antibody includes but is not limited to the following: PA8 (ATCC Accession No. HB-12605), PA9 (ATCC Accession No. HB-12606), PA10 (ATCC Accession No. HE-12607), PA11 (ATCC Accession No. HB-12608), PA12 (ATCC Accession No. HE-12609), and PA14 (ATCC Accession No. HB-12610).

This invention provides humanized forms of the above antibodies.

As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody, i.e., in the present invention, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 (71) comprise the production of chimeric antibodies having a variable region of one antibody and a constant region of another antibody.

U.S. Pat. No. 5,225,539 (72) describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 (73) and 5,693,761 (74) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (75) also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. The affinity and/or specificity of the binding of the humanized antibody may be increased using methods of directed evolution as described in Wu et al. (1999) J. Mol. Biol. 284:151 and U.S. Pat. Nos. 6,165,793; 6,365,408 and 6,413,774.

In an embodiment of the invention the humanized form of the antibody comprises a light chain variable amino acid sequence as set forth in SEQ ID NO:6. In another embodiment, the antibody comprises a heavy chain variable amino acid sequence as set forth in SEQ ID NO:9. In a further embodiment, the antibody may comprise the heavy chain variable amino acid sequence as set forth in SEQ ID NO:12.

In another embodiment, the humanized antibody comprises the light chain variable amino acid sequence as set forth in SEQ ID NO:6, and the heavy chain variable amino acid sequence as set forth in SEQ ID NO:9. Alternatively, the antibody may comprise the light chain variable amino acid sequence as set forth in SEQ ID NO:6 and the heavy chain variable amino acid sequence as set forth in SEQ ID NO:12.

The variable regions of the humanized antibody may be linked to at least a portion of an immunoglobulin constant region of a human immunoglobulin. In one embodiment, the humanized antibody contains both light chain and heavy chain constant regions. The heavy chain constant region usually includes CH1, hinge, CH2, CH3 and sometimes, CH4 region. In one embodiment, the constant regions of the humanized antibody are of the human IgG4 isotype.

This invention provides isolated nucleic acid molecules encoding these anti-CCR5 monoclonal antibodies or their humanized versions. The nucleic acid molecule can be RNA, DNA or cDNA. In one embodiment, the nucleic acid molecule encodes the light chain. In one embodiment, the nucleic acid molecule encodes the heavy chain. In one embodiment, the nucleic acid encodes both the heavy and light chains. In one embodiment, one or more nucleic acid molecules encode the Fab portion. In one embodiment, one or more nucleic acid molecules encode CDR portions. In one embodiment, the nucleic acid molecule encodes the variable domain. In another embodiment, the nucleic acid molecule encodes the variable domain and one or more constant domains.

Preferably, analogs of exemplified humanized anti-CCR5 antibodies differ from exemplified humanized anti-CCR5 antibodies by conservative amino acid substitutions. For purposes of classifying amino acid substitutions as conservative or non-conservative, amino acids may be grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Analogs of humanized anti-CCR5 antibodies show substantial amino acid sequence identity with humanized PRO 140 #1 or humanized PRO 140 #2, exemplified herein. Heavy and light chain variable regions of analogs are encoded by nucleic acid sequences that hybridize with the nucleic acids encoding the heavy or light chain variable regions of humanized PRO 140 #1, or humanized PRO 140 #2, or degenerate forms thereof, under stringent conditions.

Due to the degeneracy of the genetic code, a variety of nucleic acid sequences encode the humanized anti-CCR5 antibody of the present invention. In certain embodiments, the antibody is encoded by a nucleic acid molecule that is highly homologous to the foregoing nucleic acid molecules. Preferably the homologous nucleic acid molecule comprises a nucleotide sequence that is at least about 90% identical to the nucleotide sequence provided herein. More preferably, the nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes humanized CCR5 antibodies having the CCR5-binding properties and other functional properties described herein, which are encoded by nucleic acid molecules that hybridize under high stringency conditions to the foregoing nucleic acid molecules. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. One example of high stringency conditions is hybridization at 65 degrees Centigrade in hybridization buffer (3.5×SSC, 0.02% Ficoll, 0.02% polyvinyl pyrrolidone, 0.02% Bovine Serum Albumin, 2.5 mM NaH$_2$PO$_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68 degrees Centigrade.

The nucleic acid sequences are expressed in hosts after the sequences have been operably linked to (i.e., positioned to ensure the functioning of) an expression control sequence. These expression vectors are typically replicable in the host organisms, either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362 which is incorporated herein by reference).

*E. coli* is one prokaryotic host useful particularly for cloning the DNA sequences of the present invention. Other microbial hosts suitable for use include bacilli, such as *Bacillus subtilus*, and other enterobacteriaccae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be useful for expression. *Saccharomyces* is a preferred host, with suitable vectors having expression control sequences, such as promoters, including 3-phosphoglycerate kinase or other glycolytic enzymes and an origin of replication, termination sequences and the like as desired.

In addition to microorganisms, mammalian tissue cell culture may also be used to express and produce the polypeptides of the present invention (see, Winnacker, "From Genes to Clones,", VCH Publishers, New York, N.Y. (1987)). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc. and transformed B cells or hybridomas. Expression vectors for these cells can include expression control sequences, such as an origin of replication, a promoter, an enhancer (Queen, et al., Immunol. Rev., 89, 49-68 (1986) which is incorporated herein by reference), and necessary processing information sites, such as ribosome binding sites, RNA splice sites, polyadenylation sites and transcriptional terminator sequences. Preferred expression control sequences are promoters derived from immunoglobulin genes, SV40, Adenovirus, cytomegalovirus, Bovine Papilloma Virus, and the like.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts (see generally, Maniatis et al., Molecular Cloning: A Laboratory Manual, Cold Spring Harbor Press (1982) which is incorporated herein by reference).

Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like (see generally, R. Scopes, "Protein Purification", Springer-Verlag, New York (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings and the like (see generally, Immunological Methods, Vols. I and II, Lefkovits and Pernis, eds., Academic Press, New York, N.Y. (1979 and 1981)).

For diagnostic or detection purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available and are well known to those skilled in the art for detection of CCR5-expressing cells or detection of CCR5 modulation on cells capable of expressing CCR5.

The present invention also provides antibody fragment-polymer conjugates having an effective size or molecular weight that confers an increase in serum half-life, an increase in mean residence time in circulation (MRT) and/or a decrease in serum clearance rate over underivatized antibody fragments.

The antibody fragment-polymer conjugates of the invention can be made by derivatizing the desired antibody fragment with an inert polymer. It will be appreciated that any inert polymer which provides the conjugate with the desired apparent size or which has the selected actual molecular weight is suitable for use in constructing the antibody fragment-polymer conjugates of the invention.

Many inert polymers are suitable for use in pharmaceuticals. See, e.g., Davis et al., Biomedical Polymers: Polymeric Materials and Pharmaceuticals for Biomedical Use, pp. 441-451 (1980). In all embodiments of the invention, a non-protinaceous polymer is used. The nonprotinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g., polyvinylalcohol and polyvinvypyrrolidone. Particularly useful are polyalkylene ethers such as polyethylene glycol (PEG); polyoxyalklyenes such as polyoxyethylene, polyoxypropylene and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g., polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g., hyaluronic acid, polymers of sugar alcohols such as polysorbitol and polymannitol, heparin or heparon. The polymer prior to cross-linking need not be, but preferably is, water soluble but the final conjugate must be water soluble. Preferably, the conjugate exhibits a water solubility of at least about 0.01 mg/ml and more preferably at least about 0.1 mg/ml, and still more preferably at least about 1 mg/ml. In addition the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However it is within the scope of the invention to maximize reaction conditions to reduce cross-linking, or to purify the reaction products through gel filtration or ion-exchange chromatography to recover substantially homogeneous derivatives. In other embodiments the polymer contains two or more reactive groups for the purpose of linking multiple antibody fragments to the polymer backbone. Again, gel filtration or ion-exchange chromatography can be used to recover the desired derivative in substantially homogeneous form.

The molecular weight of the polymer can range up to about 500,000 D and preferably is at least about 20,000 D, or at least about 30,000 D, or at least about 40,000 D. The molecular weight chosen can depend upon the effective size of the conjugate to be achieved, the nature (e.g., structure such as linear or branched) of the polymer and the degree of derivitization, i.e., the number of polymer molecules per antibody fragment, and the polymer attachment site or sites on the antibody fragment.

The polymer can be covalently linked to the antibody fragment through a multifunctional crosslinking agent which reacts with the polymer and one or more amino acid residues of the antibody fragment to be linked. However, it is also within the scope of the invention to directly crosslink the polymer by reacting a derivatized polymer with the antibody fragment, or vice versa.

The covalent crosslinking site on the antibody fragment includes the N-terminal amino group and epsilon amino groups found on lysine residues, as well other amino, imino, carboxyl, sulfhydryl, hydroxyl or other hydrophilic groups. The polymer may be covalently bonded directly to the antibody fragment without the use of a multifunctional (ordinarily bifunctional) crosslinking agent, as described in U.S. Pat. No. 6,458,355.

The degree of substitution with such a polymer will vary depending upon the number of reactive sites on the antibody fragment, the molecular weight, hydrophilicity and other characteristics of the polymer, and the particular antibody fragment derivitization sites chosen. In general, the conjugate contains from 1 to about 10 polymer molecules, but greater numbers of polymer molecules attached to the antibody fragments of the invention are also contemplated. The desired amount of derivitization is easily achieved by using an experimental matrix in which the time, temperature and other reaction conditions are varied to change the degree of substitution, after which the level of polymer substitution of the conjugates is determined by size exclusion chromatography or other means known in the art.

Functionalized PEG polymers to modify the antibody fragments of the invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG-vinylsulfone, PEG-maleimide, PEG-orthopyridyl-disulfide, heterofunctional PEGS, PEG vinyl derivatives, PEG silanes and PEG phospholides. The reaction conditions for coupling these PEG derivatives will vary depending on the protein, the desired degree of PEGylation and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer. The conjugates of this invention are separated from the unreacted starting materials by gel filtration or ion exchange HPLC.

The anti-CCR5 antibody or fragments thereof may be used in combination with one or more additional anti-viral agents selected from the group consisting of nonnucleoside reverse transcriptase inhibitors (NNRTIs), a nucleoside reverse transcriptase inhibitor, an HIV-1 protease inhibitor, a viral entry inhibitor and combinations thereof.

The known NNRTI compounds that may be used in the composition of the present invention include but are not limited to efavirenz, UC-781, HBY 097, nevirapine (11-cyclopropyl-5,11,-dihydro-4-methyl-6H-dipyrido[3,2-b:2'3'-][1,4]diazepin-6-one), delavirdine ((Rescriptor™; Pharmacia Upjohn) (piperazine, 1-[3-[(1-methyl-ethyl)amino]-2-pyridinyl]-4-[[5-[(methylsulfonyl)amino]-1H-indol-2-yl]carbonyl]-, monomethanesulfonate), SJ-3366 (1-(3-cyclopenten-1-yl)methyl-6-(3,5-dimethylbenzoyl)-5-ethyl-2,4-pyrimidinedione), MKC-442 (6-benzyl-1-(ethoxymethyl)-5-isopropyluracil), GW420867x (S-3 ethyl-6-fluoro-4-isopropoxycarbonyl-3,4-dihydro-quinoxalin-2(1H)-one; Glaxo), HI-443 (N'-[2-(2-thiophene)ethyl]-N'-[2-(5-bromopyridyl)]-thiourea), and the like.

The nucleoside reverse transcriptase inhibitors that may be used in the composition in combination with at least one anti-CCR5 antibody or fragment thereof of the present invention include but are not limited to abacavir (Ziagen™, GlaxoSmithKline) ((1S,cis)-4-[2-amino-6-(cyclopropylamino)-9H-purin-9-yl]-2-cyclopentene-1-methanol sulfate (salt)), lamivudine (Epivir™, GlaxoSmthKline) ((2R,cis)-4-amino-1-(2-hydroxymethyl-1,3-oxathiolan-5-yl)-(1H)-pyrimidin-2-one), zidovudine (Retrovir™; GlaxoSmithKline) (3'azido-3'-deoxythymidine), stavudine (Zerit; Bristol-Myers Squibb) (2',3'-didehydro-3'deoxythymidine), zacitabine (Hivid™; Roche Laboratories) (4-amino-1-beta-D2',3'-dideoxyribofuranosyl-2-(1H)-pyrimidone), didanosine, and the like.

The HIV-1 protease inhibitors that may be used in the composition in combination with anti-CCR5 antibody or fragments thereof of the present invention include but are not limited to lopinavir (1S-[1R*,(R*),3R*,4R*]]-N-4-[[(2,6-dimethylphenoxy)acetyl]amino]-3-hydroxy-5-phenyl-1-(phenylmethyl)pentyl]tetrahydro-alpha-(1-methylethyl)-2- oxol(2H)-pyrimidineacetamide), saquinavir (N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-(3S)-carboxamide), nelfinavir mesylate ([3S-[2 (2S*,3S*),3a,4β,8aβ]]-N-(1,1-dimethylethyl)decahydro-2 [2-hydroxy-3-[(3-hydroxy-2-methylbenzoyl)amino]-4-(phenylthio)butyl]-3-isoquinolinecarboxamide monomethane sulfonate), indinavir sulfate (([1(1S,2R),5(S))]-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythropentonamide sulfate (1:1) salt), amprenavir ((3S)-tetrahydro-3-furyl N-[(1S,2R)-3-(4-amino-N-isobutylbenzenesulfonamido)-1-benzyl-2-hydroxypropyl] carbamate), ritonavir ((10-Hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid,5-thiazolylmethyl ester, [5S-(5R*,8R*,10R*,11R*)]), and the like.

HIV-1 fusion or viral entry inhibitors that may be used in combination with the anti-CCR5 antibody or fragments thereof of the present invention include PRO 542 (Progenics Pharmaceuticals, Inc., Tarrytown, N.Y.), T-20 (Trimeris, Inc., Durham, N.C.) (U.S. Pat. Nos. 5,464,933; 6,133,418; 6,020,459), T-1249 (U.S. Pat. Nos. 6,345,568; 6,258,782), and the like.

For combination therapy, the anti-CCR5 antibody or fragment thereof of the present invention may be provided to the subject prior to, subsequent to, or concurrently with one or more conventional antiviral agents.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

A. Materials and Methods

1) Reagents

MAb 2D7 was purchased from Pharmingen (San Diego, Calif.) and CC- and CXC-chemokines were obtained from R&D Systems (Minneapolis, Minn.). CD4-IgG2 (1), soluble (s) CD4 (2) and recombinant HIV-1$_{JR-FL}$ gp120, were produced by Progenics Pharmaceuticals, Inc. (59).

2) Isolation and Purification of Anti-CCR5 mAbs

L1.2-CCR5$^+$ cells (63) were incubated for 16 h in the presence of 5 mM sodium butyrate, which activates transcription from the cytomegalovirus (CMV) promoter that controls CCR5 expression, resulting in a 10-fold increase in cell surface co-receptor density. Female Balb/c mice were immunized intraperitoneally with $10^7$ L1.2-CCR5$^+$ cells at 3-week intervals, and administered an intravenous boost of $10^7$ L1.2-CCR5$^+$ cells three days prior to splenectomy. Splenocytes were fused with the Sp2/0 cell line. In a primary screen, supernatants from ten thousand hybridoma cultures were tested; one hundred and twenty of these inhibited HIV-1 envelope-mediated fusion between PM1 cells (10), which naturally express CCR5 and CD4, and HeLa-Env$_{JR-FL}$$^+$ cells in a resonance energy transfer (RET) assay, as previously described (19, 38). Hybridomas that produced the most potently inhibitory supernatants and that also stained CCR5$^+$ cells were sub-cloned by limiting dilution. Ascites fluids were prepared by Harlan Bioproducts for Science, Inc. (Indianapolis, Ind.) from Balb/c mice that were injected with hybridomas producing the anti-CCR5 mAbs PA8, PA9, PA10, PA11, PA12 and PA14. The mAbs were individually purified to >95% homogeneity by precipitation with ammonium sulfate followed by protein-A chromatography. All mAbs were resuspended in phosphate buffered saline (PBS) at a final concentration of 5 mg/ml.

3) Fluorescence Activated Cell Sorting (FACS) Analysis and Epitope Mapping of Anti-CCR5 mAbs Flow cytometry was used to detect cell-surface reactivity of mAbs PA8-PA12 and PA14 with CCR5. Sodium butyrate treated L1.2-CCR5$^+$ cells ($10^6$) were incubated with 0.25 μg of antibody, for 20 min at 4° C. in 0.1% sodium azide (NaN$_2$) in 50 μl of Dulbecco's PBS (DPBS). The CCR5 mAb 2D7 was used as a positive control, a non-specific murine IgG1 was used as a negative control. The cells were spun down, washed and incubated with phycoerythrin (PE)-labeled goat anti-mouse IgG (Caltag, Burlingame, Calif.) diluted 1:100, under the same conditions as the first antibody incubation. Finally, cells were analyzed by flow cytometry. PBMC were isolated and stimulated as previously described (60) and stained using similar methods.

A similar procedure was used for epitope mapping of the anti-CCR5 mAbs. A panel of seventy CCR5 point mutants has been described (20, 24, 52). The coding sequences of these proteins are sub-cloned into the pcDNA3.1 vector (Stratagene) from which transcription can be driven by a 5' T7-polymerase promoter. The CCR5 mutants carry a 9-residue hemaglutinin (HA) tag at the C-terminus for detection of protein in cell lysates or by flow cytometry. HeLa cells ($2\times10^6$) were incubated for 5 h with 20 μg/ml lipofectin and an equal amount of wild-type or mutant CCR5-expressing plasmid in OPTI-MEM (Life Technologies, Gaithersburg, Md.). The cells were then infected for 12 h with $2\times10^7$ p.f.u. of vTF7 (23) to boost CCR5 expression, detached with 2 mM ethylenediamine tetraacetic acid (EDTA) in PBS and washed once with binding buffer (1% BSA, 0.05% NaN$_3$ in DPBS). Cells ($1\times10^6$) were surface labeled with mAbs as described in the previous paragraph, washed once with the incubation buffer and resuspended in 1 ml of 1×FACSlyse in water (Becton Dickinson) for 30 min at room temperature, to permeabilize the cell membranes. The cells were then spun down, washed with the incubation buffer and incubated for 1 h at 37° C. with 4 μg/ml of a fluorescein isothiocyanate (FITC)-labeled mouse anti-HA mAb (BabCo, Richmond, Calif.) for intracellular labeling. Finally, cells were washed once with binding buffer and once with DPBS, resuspended in 1% formaldehyde in PBS and analyzed by flow cytometry. The extent of binding of a mAb to mutant CCR5 was determined by the equation (mutant CCR5 PE m.f.i./wt CCR5 PE m.f.i.)/(mutant CCR5 FITC m.f.i./wt CCR5 FITC m.f.i.)× 100%. This normalizes mAb binding for mutant co-receptor expression levels.

4) gp120/sCD4-Binding Assay gp120 was biotinylated using NHS-biotin (Pierce, Rockford, Ill.) according to the manufacturer's instructions, and uncoupled biotin was removed by diafiltration. Sodium butyrate-treated L1.2-CCR5$^+$ cells were incubated with varying dilutions of an equimolar mixture of sCD4 and biotinylated gp120, or 1.25 μg/ml of sCD4 and 2.5 μg/ml of biotinylated gp120 in the presence of varying concentrations of anti-CCR5 mAbs PA8-PA12, PA14, 2D7 or a non-specific murine IgG1, for 1 h at room temperature in 0.1% NaN$_2$ in DPBS. Cells were washed with the incubation buffer and incubated with streptavidin-PE (Becton Dickinson) diluted 1:50, for 1 h at room temperature. Finally, cells were washed with binding buffer and analyzed using a fluorescence plate reader (Perspective Biosystems, Framingham, Mass.).

5) Inhibition of Envelope-Mediated Cell-Cell Fusion and HIV-1 Entry by Anti-CCR5 mAbs HIV-1 envelope-mediated fusion between HeLa-$Env_{JR-FL}^+$ and PM1 cells was detected using the RET assay. Equal numbers ($2 \times 10^4$) of fluorescein octadecyl ester (F18)-labeled envelope-expressing cells and octadecyl rhodamine (R18)-labeled PM1 cells were plated in 96-well plates in 15% fetal calf serum in DPBS and incubated for 4 h at 37° C. in the presence of varying concentrations of the anti-CCR5 mAbs, PA8-PA12, PA14, 2D7 or a non-specific murine IgG1. Fluorescence RET was measured with a Cytofluor plate-reader (PerSeptive Biosystems) and % RET was determined as previously described (38).

NLluc⁺env⁻ viruses complemented in trans by envelope glycoproteins from JR-FL or Gun-1 were produced as previously described (20). U87MG-CD4⁺CCR5⁺ cells (14) were infected with chimeric, reporter viruses containing 50-100 ng/ml p24 in the presence of varying concentrations of the individual mAbs. After 2 h at 37° C., virus-containing media were replaced by fresh, mAb-containing media. Fresh media, without antibodies, were added again after 12 hours. After a total of 72 h, 100 μl of lysis buffer (Promega) were added to the cells and luciferase activity (r.l.u.) was measured as described (20). The % inhibition of HIV-1 infection is defined as [1−(r.l.u in the presence of antibody/r.l.u in the absence of antibody)]×100%.

6) Calcium Signaling Assays

The fluorochrome Indo-1AM (Molecular Probes, Eugene, Oreg.) was added to sodium butyrate treated L1.2-CCR5⁺ cells at a final concentration of 5 μM. After incubation at 37° C. for 30 min, the cells were washed once and resuspended in Hank's buffered saline. Cells ($10^6$) were stimulated sequentially with an anti-CCR5 mAb or PBS, followed 60 s later with RANTES. MAbs PA8-PA12 and PA14 were used at a concentration of 100 μg/ml, 2D7 at 20 μg/ml and RANTES at 250 ng/ml. Calcium flux inhibition by PA14 and 2D7 was also tested for a wide range of mAb concentrations, ranging from 0-100 μg/ml. Intracellular calcium levels were monitored using a Perkin-Elmer LS-50S fluorescence spectrophotometer by measuring the ratio of fluorescence emissions at 402 nm (bound dye) and 486 nm (free dye) following excitation at 358 nm.

B. Results and Discussion

1) Isolating anti-CCR5 Monoclonal Antibodies PA8, PA9, PA10, PA11, PA12 and PA14

It was found that peptides corresponding to the extracellular domains of CCR5 are inefficient at raising specific, high-titer antibody responses against the native, cell surface receptor (50). Balb/C mice were immunized, therefore, with L1.2-CCR5⁺ cells and hybridoma culture supernatants were tested for their ability to inhibit JR-FL envelope-mediated membrane fusion with CD4⁺CCR5⁻ PM1 cells in the RET assay (19, 38). Even though well over a hundred supernatants inhibited cell-cell fusion by >50%, only six—designated PA8, PA9, PA10, PA11, PA12 and PA14—specifically and intensely stained L1.2-CCR5⁺ but not the parental L1.2 cells, as demonstrated by flow cytometry (data not shown). Based on previous experience, it was assumed that the other mAbs capable of inhibiting cell-cell fusion were probably directed against cell surface adhesion molecules such as LFA-1 (37). Hybridomas PA8-PA12 and PA14 were determined by isotyping ELISA (Cappell, Durham, N.C.) to secrete IgG1 mAbs. Ascites fluids were prepared from Balb/C mice that were injected with the six hybridomas and the IgG1 fractions were purified. PA8, PA9, PA11, PA12 and PA14 exhibited distinct isoelectric focussing profiles, whereas PA10 had a very similar profile to that of PA9 and therefore may be a second isolate of the same mAb (data not shown).

2) MAb Binding to CCR5+ Cells

None of the purified anti-CCR5 mAbs stained the parental L1.2 cell line (data not shown). However, mAbs PA9-PA12 and PA14 stained >90%, and PA8 stained ~70%, of L1.2-CCR5⁺ cells as determined by flow cytometry, showing they recognized CCR5 (FIG. 1). The anti-CCR5 mAb 2D7, which was a positive control in our experiments, also stained >90% of L1.2-CCR5⁺ cells. PA8-PA12 and PA14 are all IgG1, and react equally well with a goat anti-mouse IgG, whereas 2D7 is an IgG2a and may react differently with the reporter antibody. Only mean fluorescence intensities (m.f.i.) measured with mAbs PA8-PA12 and PA14 therefore are directly comparable. The rank order of mean fluorescence intensities (m.f.i.) was PA12~PA11>(2D7=) PA14~PA10~PA9>PA8. The difference between PA12 m.f.i. and PA8 m.f.i. was three-fold. Differences in staining intensity between PA8 and the other mAbs remained constant over a wide range of concentrations (data not shown) and probably do not correspond to differences in mAb affinities for CCR5. This implies that PA8 interacts only with a subset of CCR5 molecules present on the surface of L1.2-CCR5⁺ cells.

Compared with L1.2-CCR5+ cells, mitogen-stimulated PBMC exhibited different patterns of staining by the anti-CCR5 mAbs. 2D7 and PA14 stained >20%, PA11 and PA12 stained ~10%, PA8, PA9 and PA10 stained <5% of PBMC (FIG. 1). The mean fluorescence intensities of the stained PBMC were about ten-fold lower than those obtained with L1.2-CCR5⁺ cells for each mAb; their rank order was (2D7>) PA14>PA12~PA11~PA10~PA9~PA8. Again, this differed somewhat from the order of reactivities observed on CCR5 transfectants. The difference between PA9 m.f.i. and PA14 m.f.i. was seven-fold. Other groups have observed similar differences in the ability of anti-CCR5 mAbs to stain stable, CCR5⁺ cell lines versus PBMC (28). This may be due to cell-specific differences in CCR5 conformation, post-translational modification or oligomerization. Alternatively, association with other cell surface molecules may differ between cells. Since an obvious choice for such a molecule would be the CD4 cell surface antigen, which is absent from L1.2-CCR5⁺ cells and present on PBMCs, we also tested the ability PA8-PA12, PA14 and 2D7 to stain HeLa cells transiently expressing CCR5 alone or with CD4. No differences were observed in the ability of any of the mAbs to stain cell surface CCR5 in the presence of CD4 (data not shown). If there is an association between these two proteins, it does not involve epitopes recognized by the anti-CCR5 mAbs available to us. Alternatively, an association between CCR5 and CD4 might only occur on primary lymphocytes.

3) Epitope Mapping of the mAbs Using CCR5 Alanine Mutants

None of the antibodies were able to detect reduced and denatured CCR5 protein by Western blotting indicating that they recognize conformationally sensitive epitopes (data not shown). MAb epitope mapping studies were performed using a panel of seventy alanine point mutants of residues in the Nt and ECLs of CCR5. HeLa cells were lipofected with mutant or wild type CCR5 coding sequences appended with C-terminal HA tags, and infected with vTF7 (23) to boost co-receptor expression. The cells were then incubated with the anti-CCR5 mAbs and their binding was revealed by a PE-labeled goat anti-mouse IgG. A second, intracellular stain was performed with a FITC-labeled anti-HA mAb (BabCo).

Figure 4:
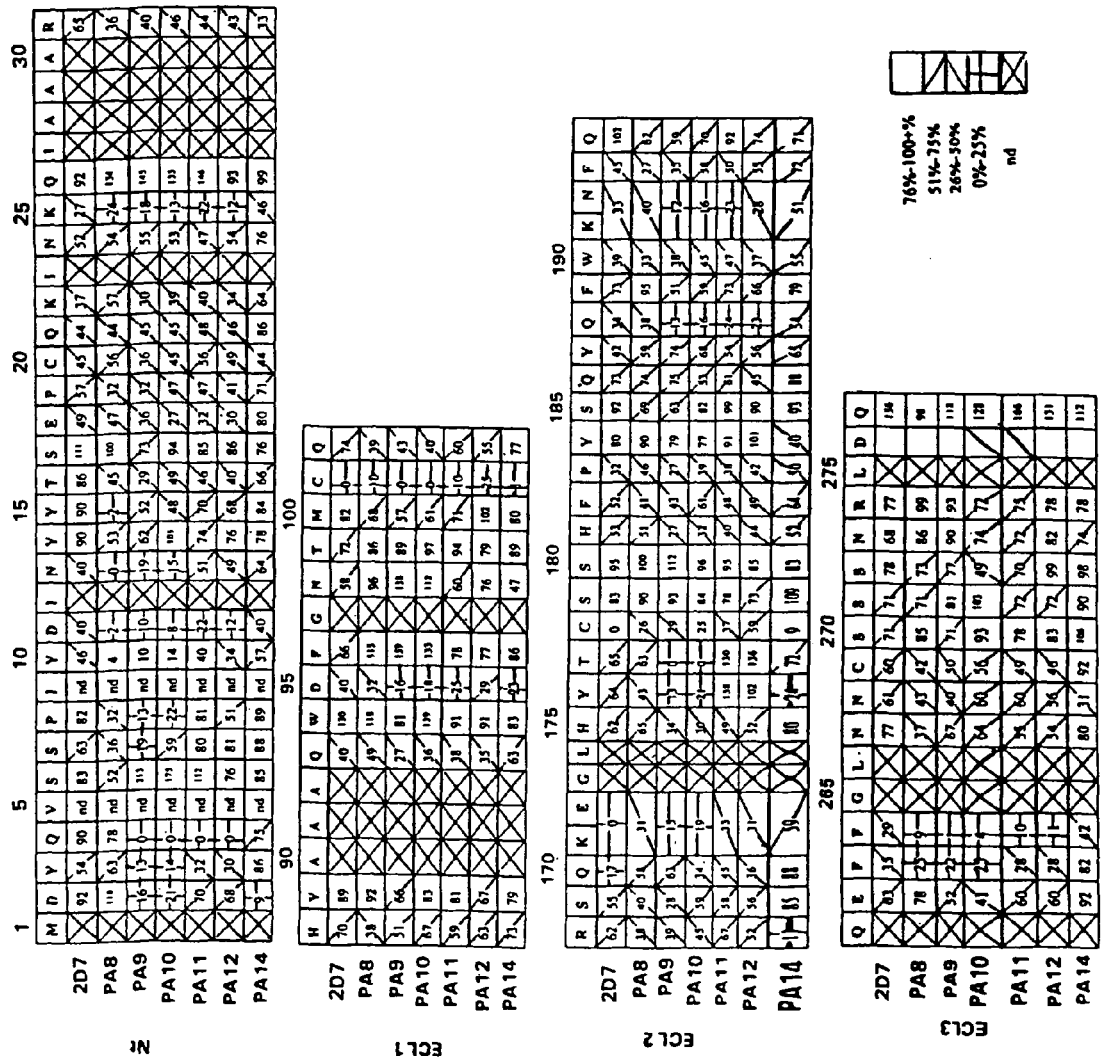

This internal control allowed us to directly normalize staining by the anti-CCR5 mAbs for mutant co-receptor expression levels on the cell surface. Hence, mAb binding to each mutant is expressed as a percentage of binding to wild-type CCR5 (FIG. 4).

Certain point mutations reduced the binding of all of the antibodies to CCR5 by >50. In general, PA8-PA12 were the most affected, PA14 and 2D7 the least affected by this class of mutants, which included the cysteine pair C101A and C178A, the Nt mutants Y10A, D11A, K25A, the ECL1 mutant D95A, the ECL2 mutants K171A/E172A, Q188A, K191A/N192A, and the ECL3 mutants F263A and F264A (FIG. 1). One interpretation is that these residues are not part of the mAb epitopes per se, but that changing them to alanines causes conformational perturbations that have a common effect on binding of all mAbs. We assumed that if a mutation lowered binding of an individual mAb by >75%, and did not also lower binding of most of the other antibodies, the residue was probably a direct contributor to the epitope recognized by the mAb. Using these stringent guidelines, it was concluded that the seven anti-CCR5 mAbs recognize overlapping but distinct epitopes (FIG. 4). MAb PA8 binding to CCR5 depended on N13 and Y15 in the Nt. MAb PA9 and PA10 required D2, Y3, Q4, P8 and N13 in the Nt, and Y176 and T177 in ECL2. MAb PA9 also required S7 in the Nt. MAb PA11 and PA12 binding depended on Q4 in the Nt. PA14 required D2 in the Nt, and R168 and Y176 in ECL2. Finally, mAb 2D7 required Q170 and K171/E172 in ECL2 in order to bind to CCR5.

4) Chemokine Signaling in the Presence of Anti-CCR5 mAbs

Figure 5A:
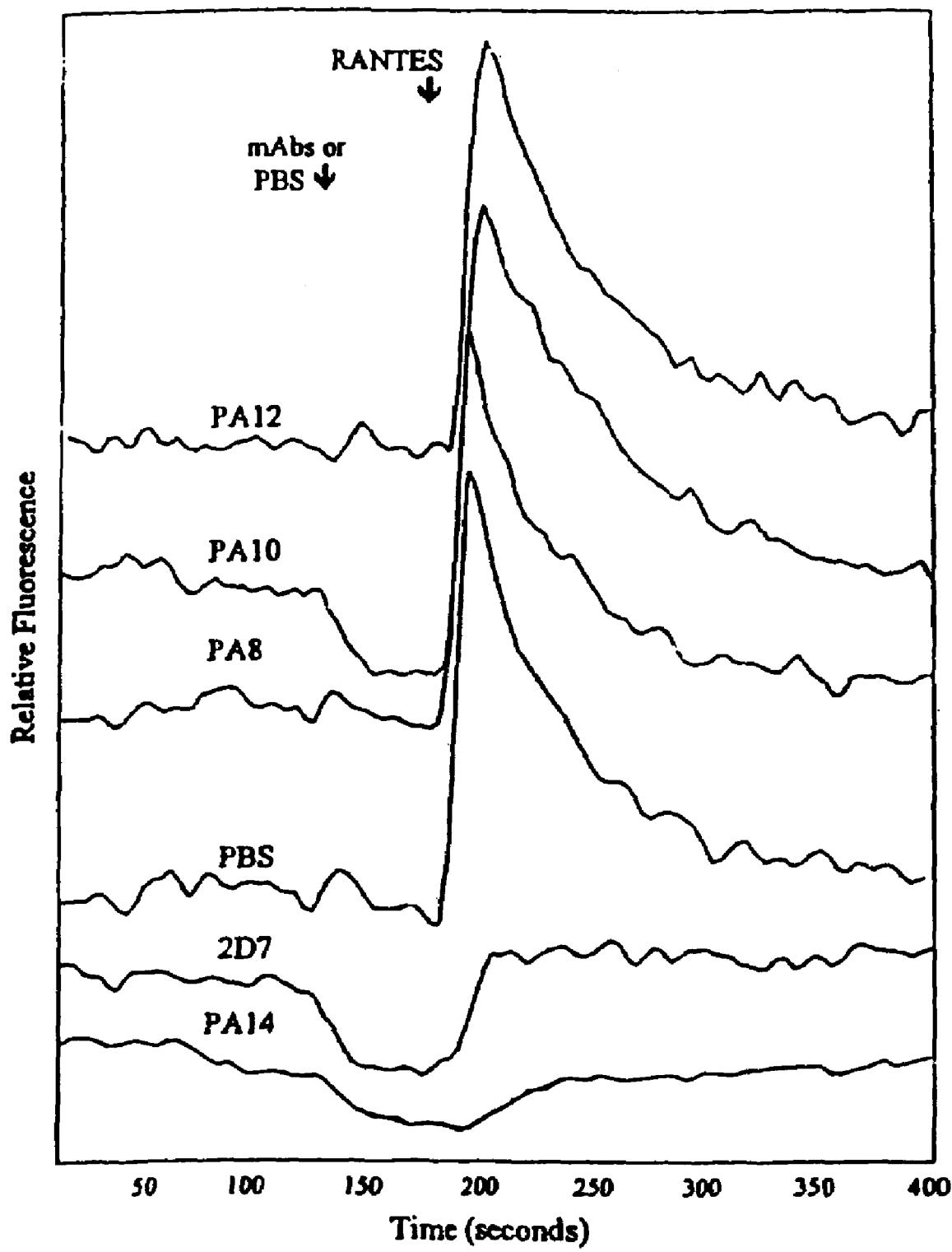
Figure 5B:
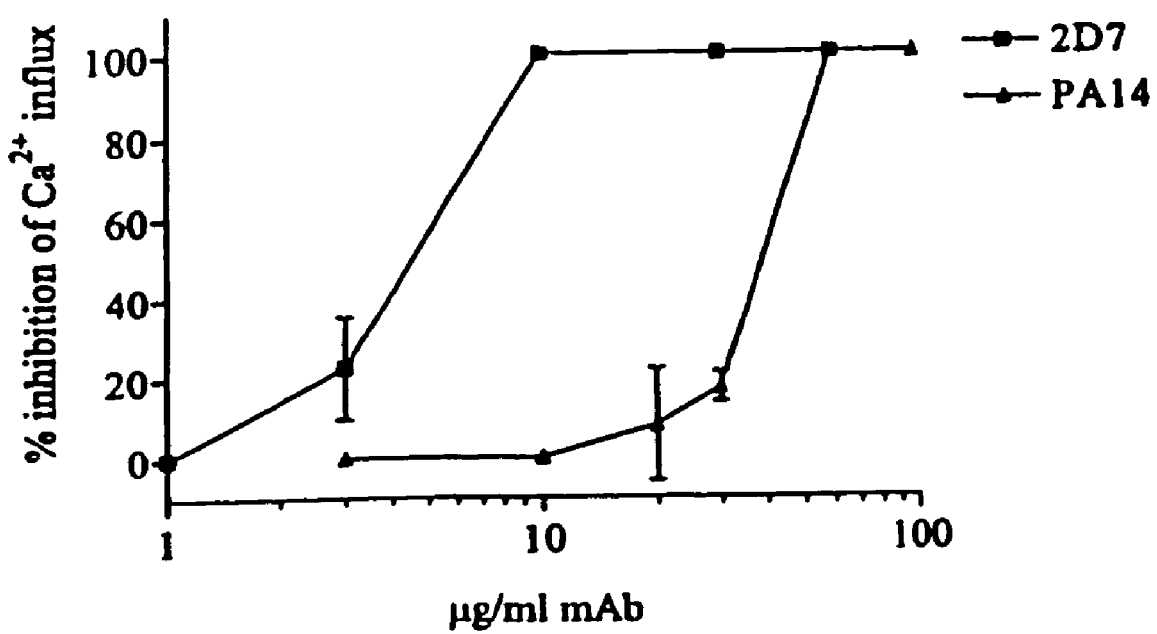
Figure 6A:
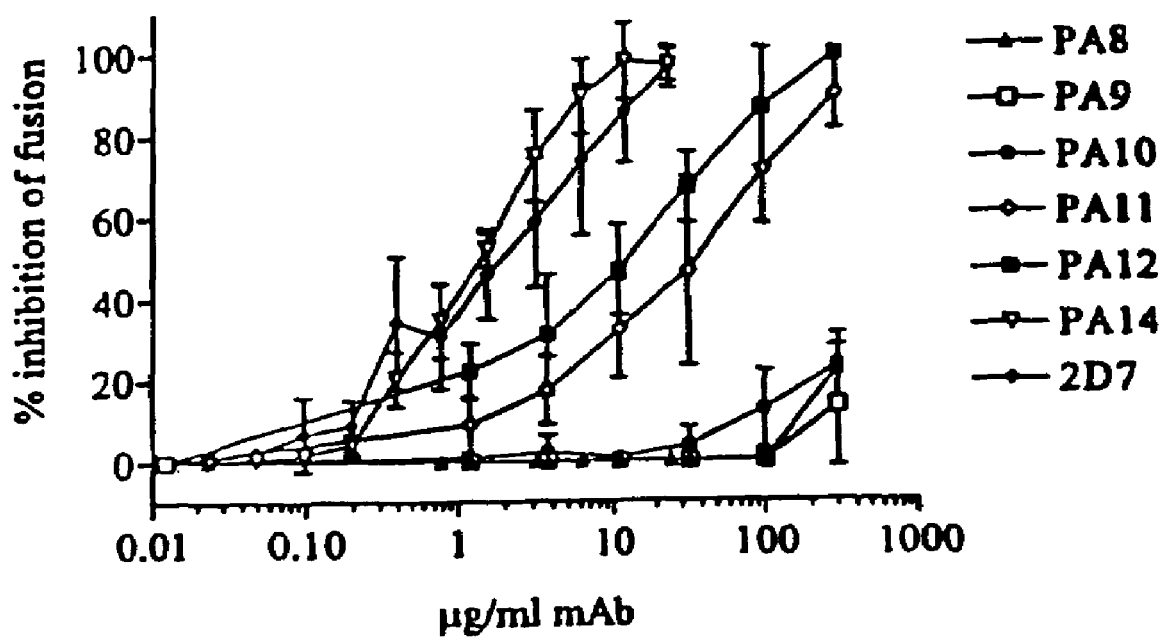
Figure 6B:
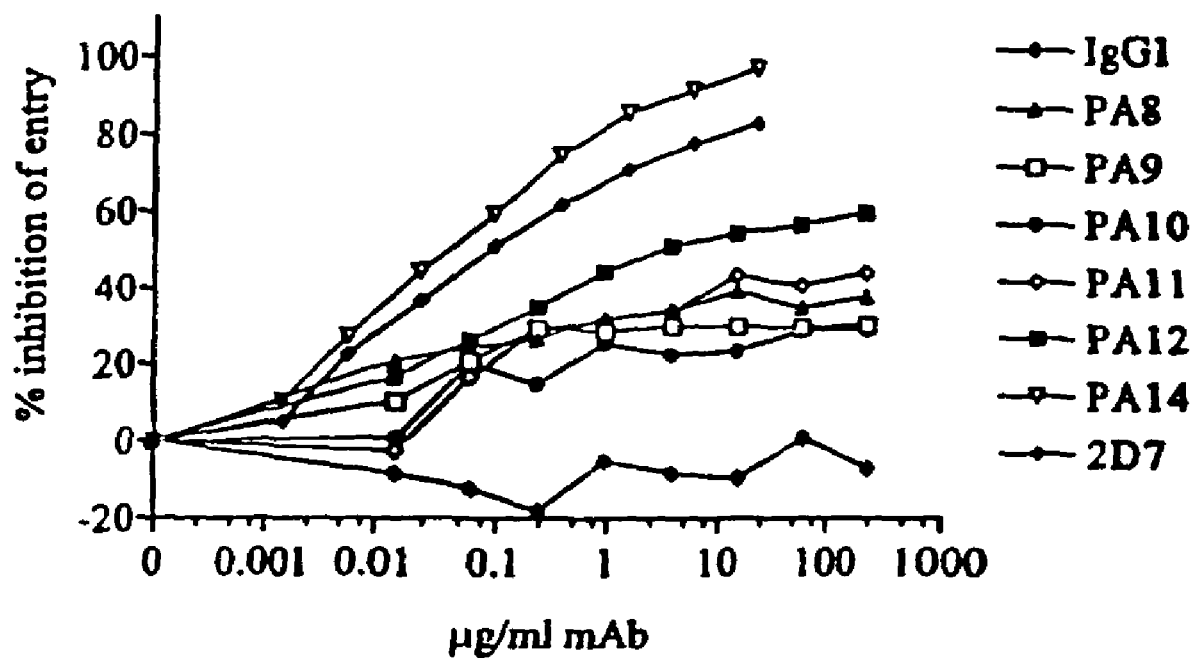
Figure 6C:
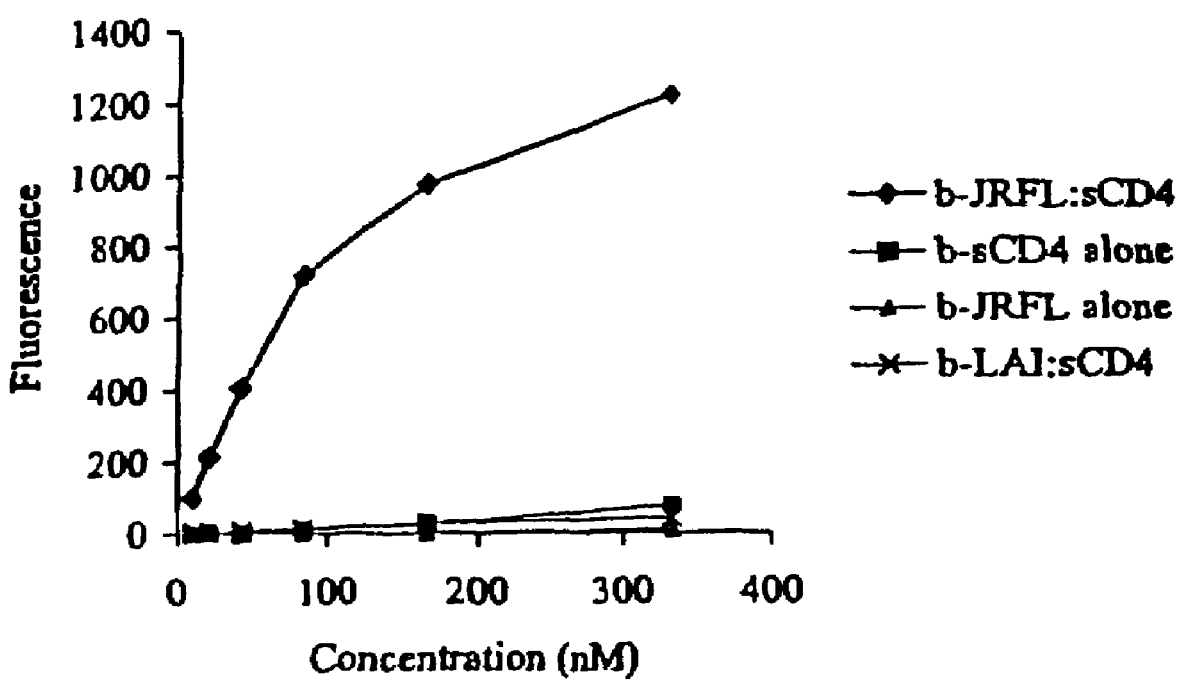
Figure 6D:
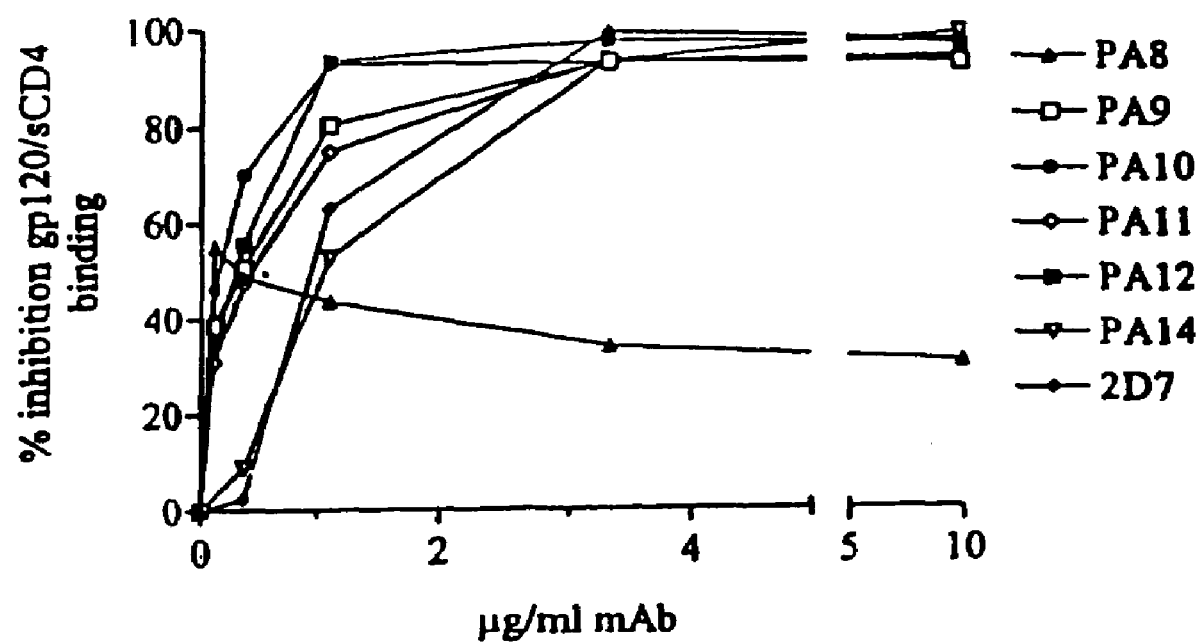

Chemokine receptor-binding agents can be antagonists or, more rarely, agonists of receptor-mediated intracellular signaling. Alternatively, they could have no effect on signaling. CCR5 is able to bind three CC-chemokines, RANTES, MIP-1α and MIP-1β, and transduce a signal that modulates cytosolic calcium levels. We therefore tested the agonist/antagonist activity of various concentrations of mAbs PA8-PA12, PA14 and 2D7. Changes in intracellular calcium concentrations, $(Ca^{2+})i$, were measured in Indo-1-loaded L1.2-CCR5$^+$ cells. None of the mAbs stimulated a change in $(Ca^{2+})i$, indicating that they are not agonists for CCR5. PA8-PA12 were also unable to inhibit $Ca^{2+}$ fluxes induced by RANTES (FIG. 5A and data not shown), even at concentrations as high as 100 μg/ml, showing they are not antagonists either. These concentrations provide saturating binding of the mAbs to L1.2-CCR5$^+$ cells, as shown by flow cytometry and the gp120/CCR5 binding assay (FIG. 6D and data not shown). MAbs PA14 and 2D7, however, blocked calcium mobilization induced by RANTES, although with different potencies (FIG. 5A, 5B). The IC$_{50}$ for PA14 calcium influx inhibition was 50 μg/ml, which was approximately 8-fold higher than the IC$_{50}$ for 2D7 (FIG. 5B). RANTES-, MIP-1α- and MIP-1β-induced calcium fluxes were each inhibited by similar concentrations of PA14 (data not shown). None of the mAbs affected SDF-1-induced calcium mobilization in L1.2-CCR5$^+$ cells, which endogenously express CXCR4 (data not shown). Finally, neither mAbs nor CC-chemokines affected cytosolic calcium levels in parental L1.2 cells (data not shown).

5) Inhibition of CCR5 Co-Receptor Function by the mAbs

MAbs PA8-PA12 and PA14 were initially selected on the basis of their ability to inhibit HIV-1 envelope-mediated cell-cell fusion. This activity was confirmed and quantified for the purified mAbs. As expected, all six mAbs, as well as mAb 2D7, blocked fusion between CD4$^+$CCR5$^+$ PM1 cells and HeLa-Env$_{JR-FL}$$^+$ cells in the RET assay. The rank order of potency was 2D7~PA14>PA12>PA11>PA10~PA9~PA8 (FIG. 6A). IC$_{50}$ values for PA14 and 2D7 were 1.7 μg/ml and 1.6 μg/ml respectively, for PA11 and PA12 these were 25.5 μg/ml and 10.0 μg/ml respectively (FIG. 3). PA8, PA9 and PA10 inhibited fusion by only 10-15% at 300 μg/ml. None of the mAbs affected fusion between PM1 cells and HeLa-Env$_{LAI}$$^+$ cells, which express the full length envelope protein from an X4 virus (data not shown).

The ability of the different anti-CCR5 mAbs to inhibit entry of a prototypic R5 virus, JR-FL, and a R5X4 virus, Gun-1, in a single-round of replication, luciferase-based entry assay was also tested. The rank order of potency in the entry assay was similar to the one determined in the cell-cell fusion assay (FIG. 6B). A >50% inhibition of JR-FL or Gun-1 entry with PA8-PA11 was unable to be obtained. The IC$_{50}$ value for PA12 was 2.5 μg/ml. However, inhibition of entry by >60% with this mAb was unable to be obtained. The IC$_{50}$ values for PA14 and 2D7 inhibition of JR-FL entry were determined to be 0.024 and 0.026 μg/ml respectively (FIG. 3), and were 60-fold lower then those obtained in the fusion assay. Entry of dual-tropic Gun-1 was 2-3-fold more sensitive to inhibition by anti-CCR5 mAbs than JR-FL entry (data not shown).

Anti-co-receptor mAbs might inhibit envelope-mediated fusion either by directly affecting the gp120/CCR5 interaction or by impeding post-binding steps involved in the formation of an active fusion complex. To determine the mechanism of inhibition of viral fusion and entry by PA8-PA12 and PA14, the ability of the different mAbs to block the gp120/CCR5 interaction was tested. For this an assay that detects binding to L1.2-CCR5$^+$ cells of biotinylated HIV-1$_{JR-FL}$ gp120 complexed with sCD4 was used. No binding of biotinylated gp120 was observed in the absence of sCD4 or CCR5, or when HIV-1$_{LAI}$ gp120 was used (FIG. 6C).

With the exception of PA8, all mAbs abrogated gp120/sCD4 binding to L1.2-CCR5$^+$ (FIG. 6D). Inhibition by PA8 saturated at ~40%, which concurs with flow cytometry data (FIG. 1) in suggesting that this mAb binds only to a subset of CCR5 molecules on L1.2-CCR5$^+$ cells. MAbs PA9, PA10, PA11 and PA12 inhibited binding with IC$_{50}$ values of 0.24, 0.13, 0.33, 0.24 μg/ml respectively (FIG. 3). Surprisingly, mAbs PA14 and 2D7 were the two least efficient inhibitors of gp120/sCD4 binding, with IC$_{50}$ values of 1.58 and 1.38 μg/ml respectively (FIG. 3). Therefore, there was no correlation between the ability of a mAb to inhibit gp120/CD4/CCR5-mediated membrane fusion and entry and its ability to block gp120/sCD4 binding to the co-receptor.

6) Synergistic Inhibition of HIV-1 Fusion by Combinations of Anti-CCR5 mAbs and Other Viral Entry Inhibitors Co-receptor-specific agents may act at multiple stages of the entry process and exhibit non-additive effects when used in combination. From a clinical perspective, it is important to determine the interactions of co-receptor-specific drug candidates with endogenous chemokines, which may afford some level of protection against disease progression. CCR5 mAbs were therefore tested in combination with each other or with RANTES, or with CD4-IgG2, which binds to HIV-1 gp120 to inhibit attachment to target cells. Dose-response curves were obtained for the agents used individually and in combination in viral fusion and entry assays. Data were analyzed using the median effect principle (9). The concentrations of single-agents or their mixtures required to produce a given effect were quantitatively compared in a term known as the Combination Index (CI). A CI value greater than 1 indicates antagonism, CI~1 indicates an additive effect, and CI<1 indicates a synergistic effect wherein the presence of one agent enhances the effect of another.

Combinations of PA12 and 2D7 were the most potently synergistic, with CI values ranging between 0.02 and 0.29, depending on the ratio of the antibodies (FIG. 7 and FIG. 2). The degree of synergy is known to vary with the stoichiometry of the agents. The viral entry and fusion assays were generally consistent in identifying mAb combinations that are highly synergistic, PA12 and 2D7; moderately synergistic, PA12 and PA14; additive, PA11 and PA12; and weakly antagonistic, PA14 and 2D7. The lack of synergy between PA14 and 2D7 is not surprising given that these mAbs cross-compete for binding to CCR5$^+$ cells as determined by flow cytometry (data not shown). The observation of an additive effect of PA11 and PA12 may be an indication that these mAbs bind to slightly different epitopes in CCR5, while sharing a dependency on residue Q4 in the Nt.

The ability of mAbs PA12, PA14 and 2D7 to synergize with RANTES in blocking cell-cell fusion was also tested. PA12 and RANTES combinations exhibited moderate synergy (FIG. 2). PA14 and 2D7 exhibited no synergy with RANTES, which is consistent with these mAbs being inhibitory of RANTES binding and signaling (FIG. 5A, 5B). Finally, we tested synergy between mAbs PA12, PA14, 2D7 and CD4-IgG2, which interacts with gp120. We observed moderate synergy between PA12 and CD4-IgG2 but no synergy between PA14 or 2D7 and CD4-IgG2 (FIG. 2).

EXPERIMENTAL DISCUSSION

Six murine anti-CCR5 IgG1 mAbs were isolated and characterized. Whereas PA8, PA9, PA11, PA12 and PA14 are distinct molecular species, PA9 and PA10 are indistinguishable by the analyses and therefore are probably the same mAb. All of the mAbs that were isolated recognize complex conformational epitopes, as is often the case with mAbs raised against native, cell surface proteins. Epitope mapping was performed for all mAbs using a panel of CCR5 alanine point mutants. Residues that affected binding of all mAbs similarly were assumed to cause conformational perturbations in the co-receptor and not to constitute part of the mAb epitopes. Only two such residues, Y10 and D11, have been shown to affect HIV-1 entry (20, 52). The PA8, PA11 and PA12 epitopes are located exclusively in the Nt domain. Consistent with this result, PA8 was able to bind a biotinylated Nt peptide, containing residues D2 through R31, in an ELISA (data not shown). However, PA11 and PA12, whose binding strongly depended only on Q4, did not bind the Nt peptide in solution (data not shown). One possibility is that the Nt peptide does not assume the proper conformation for recognition by PA11 and PA12, whereas PA8 binding may be less conformation-dependent. Alternatively, PA11 and PA12 might interact with residues that we have not mutated, or form weak bonds with amino acids located in other domains of CCR5, or bind peptide backbone atoms whose presentation may be unchanged by mutagenesis. Antibodies PA9, PA10 and PA14 recognized epitopes that included residues in both the Nt and ECL2 domains of CCR5, whereas the 2D7 epitope was located exclusively in ECL2.

The PA14 epitope comprises both D2 in the Nt and R168 in ECL2 indicating that these two residues are proximal to one another within the context of a mAb footprint. They may even directly interact with one another through their opposite charges.

MAbs PA8-PA12 and PA14 stained CCR5$^+$ cells with different intensities and in a cell type-dependent manner. All mAbs except PA8 stained >90% L1.2-CCR5$^+$ cells, the highest mean fluorescence intensity being observed with PA11 and PA12. However, PA14 and 2D7 stained the highest percentage of PBMC and also yielded the highest mean fluorescence intensities on these cells. Hill et al. (28) have recently characterized a panel of anti-CCR5 mAbs that similarly stained transfected cells, but only two of eight stained PBMC, and none stained primary monocytes. A low affinity for CCR5 probably accounted for the non-reactivity of two of the mAbs with primary cells, but this was unlikely to be the explanation for the failure of the other four to react. In our mAb panel, we observe the most intense staining of PBMC by mAbs 2D7 and PA14 that have epitopes located entirely or partially in the first ten residues of ECL2. Hill et al. report, however, that mAbs specific for the Nt and ECL1 stain PBMCs, while mAbs to ECL2 and ECL3 do not stain PBMC, so a consistent pattern of reactivity has not been identified. One explanation for cell type-specific staining by mAbs would be that activated PBMCs (and monocytes) secrete CC-chemokines that bind to cell surface CCR5, masking some mAb epitopes. However, one would expect this to be especially true for PA14 and 2D7, which are antagonists of chemokine-induced calcium mobilization and presumably compete with CC-chemokines for binding to CCR5. Yet these mAbs stain PBMC the most intensely. Alternatively, differential CCR5 epitope exposure may reflect cell type-specific receptor oligomerization, association with other cell-surface molecules, or different post-translational modifications such as glycosylation. We have shown that differences in mAb binding probably do not reflect cell type-specific differences in CD4/CCR5 interactions.

MAbs PA8-PA12 did not inhibit CC-chemokine induced calcium mobilization in CCR5$^+$ cells, nor did they mediate signaling through CCR5. MAbs 2D7 and PA14 were inhibitors of CC-chemokine induced calcium mobilization, but 2D7 was almost an order of magnitude more potent than PA14. This may be because the PA14 epitope overlaps less with the CC-chemokine binding domain on CCR5 than the 2D7 epitope. All of the mAbs also blocked HIV-1 entry and envelope-mediated membrane fusion, but inhibition of cell-cell fusion required in some cases almost two orders of magnitude more antibody than what was needed to block viral entry. Presumably, more gp120/CD4/CCR5 interactions as well as interactions between adhesion molecules are established and act cooperatively during cell-cell fusion, compared to virus-cell fusion, making it more difficult to inhibit. This is commonly observed with antibodies to LFA-1 or to the HIV-1 envelope glycoprotein (45, 51). PA8, PA9 and PA10 were unable to block cell-cell fusion by >15% and viral entry by >40%, even at the highest antibody concentrations. However, >90% inhibition of fusion could be attained with PA11, PA12 and PA14, and >90% inhibition of entry could be attained with PA14. The most potent of the six mAbs in blocking fusion and entry was PA14, which was as effective as 2D7. Surprisingly, PA14 and 2D7 were among the least potent inhibitors of gp120/sCD4 binding to L1.2-CCR5$^+$ cells, whereas PA9-PA12 blocked with similar potencies, and PA8 was unable to block >40% of gp120/sCD4 binding. These observations raise questions about the nature of the CCR5 molecules presented on different cells and about the mechanisms of inhibition of viral fusion and entry. It may be that CCR5 on L1.2 cells, used in the mAb and gp120-binding assays, is not in an identical conformation to CCR5 on PBMC, used in the mAb-binding assay, or to CCR5 on PM1 and U87MG cells used in the fusion and entry assays.

The low staining of PBMC and the partial inhibition of fusion and entry by some of our mAbs indicate that they are only able to bind to a subset of CCR5 molecules expressed on primary lymphocytes, PM1 and U87MG-CD4$^+$CCR5$^+$ cell lines. Yet, other than PA8, all mAbs are able to stain >90%

L1.2-CCR5+ cells and to completely block binding of the gp120/sCD4 complex to these cells. At least one difference between L1.2-CCR5+ and the other cells that we have used is the density of co-receptor protein on the cell surface. Indeed, we estimate that the L1.2-CCR5+ cells express 10- to 100-fold more cell surface co-receptor than PM1 and U87MG-CD4+CCR5+ cells. But when HeLa cells are engineered to transiently express as much co-receptor as the L1.2-CCR5+ cell line, we are still unable to detect gp120/sCD4 binding to them (data not shown). Over-expression of CCR5 on L1.2, along with other cell-specific factors therefore, might favor a co-receptor conformation that prominently exposes the Nt, making it more accessible to both mAbs and gp120. Such a conformation might be induced by receptor oligomerization, by diminished or altered associations with cell surface proteins or by receptor interactions with G proteins (25, 62). Do multiple conformations of CCR5 co-exist on the cell surface, and are they all permissive for viral entry? The patterns of mAb reactivity would suggest so, since HIV-1 entry and fusion can occur, albeit at reduced levels, in the presence of mAb concentrations that saturate epitopes required for gp120 binding to L1.2-CCR5+ cells. We favor the hypothesis that the co-receptor molecules present on L1.2-CCR5+ cells possess one HIV-1 entry-competent conformation whereas CCR5 molecules on PBMC, PM1 and CCR5+ U87MG exist in multiple, entry-competent states that display different mAb reactivities. Whereas PA14 and 2D7 may recognize all conformations, other mAbs may not. Why L1.2 cells are conducive to a particular fusion-competent conformation remains to be determined.

It has recently been demonstrated that the gp120-binding domain lies in the first twenty residues of the CCR5 Nt domain. MAbs to the gp120-binding domain on CCR5 potently block this interaction but are not nearly as efficient at inhibiting HIV-1 fusion and entry into target cells as PA14 and 2D7, whose epitopes lie outside this region. PA14 recognizes the tip of the Nt and residues in ECL2, whereas the 2D7 epitope is located exclusively in ECL2. At the mechanism of action of these mAbs can only be speculated. It may be that their binding to the first few residues of ECL2 induces conformational changes in the co-receptor that prevent membrane fusion. Alternatively, obstruction of ECL2 epitopes might impede co-receptor oligomerization and the formation of a fusion-competent protein complex. Yet another possibility is that residues in ECL2 face the inside of the fusion pore and binding of the mAbs impedes gp41 from inserting the fusion peptide into the plasma membrane. In contrast, mAbs PA8-PA12 probably inhibit fusion and entry only by directly competing for binding with gp120/CD4 complexes. We do not know if parameters other than epitope exposure and affinity for CCR5 determine the efficacy of viral entry inhibition by these mAbs. It is unclear why inhibiting steps subsequent to the gp120/co-receptor interaction would be more efficient than directly blocking that interaction. One way to explain this would be to assume that the off rate of gp120 binding to CCR5 is much lower than the on rate of mAb binding to CCR5. Thus, every time a mAb detaches itself from a co-receptor molecule, a virion-associated gp120 molecule replaces it in a quasi-irreversible fashion since this interaction leads to membrane fusion.

Synergy between combinations of anti-CCR5 mAbs is probably a result of their interactions with distinct epitopes that are involved in inter-dependent, consecutive steps of HIV-1 entry. The degree of synergy observed between PA12 and 2D7 (CI<0.1 under many circumstances) is extraordinary since CI values <0.2 are rarely observed for combinations of anti-HIV-1 antibodies (33, 35, 61), reverse transcriptase inhibitors (29), or protease inhibitors (44). Because of its potency, the PA12:2D7 combination was examined in multiple assay formats and concentration ratios, for which consistently high levels of synergy were observed. Moderate synergy was observed for PA12 combined with PA14. We also observed moderate synergy between PA12 and CD4-IgG2. The CD4/gp120 complex is metastable and if it is unable to interact with a co-receptor, decays into a non-fusogenic state (45-48). Since PA12 directly blocks the gp120-binding site on CCR5, its presence may shift the equilibrium towards inactivation of the gp120/CD4 complex. This would explain why we observe synergy between CD4-IgG2 and mAb PA12 with respect to inhibition of fusion and entry. The lack of synergy between mAb PA14 and CD4-IgG2 suggests that they act on two non-consecutive and independent steps of viral entry. A combination of further studies will be needed to determine the precise mechanisms of synergy of the different compounds with respect to inhibition of viral fusion and entry.

The above results are consistent with a model wherein HIV-1 entry occurs in three distinct steps involving receptor binding, co-receptor binding, and co-receptor mediated membrane fusion. Separate co-receptor binding and fusion events are suggested by the lack of correlation between the monoclonal antibodies' abilities to block gp120 binding and HIV-1 fusion/entry. The chronology of events during fusion is further suggested by the patterns of synergies observed. Agents, such as PA12, that potently inhibit the middle step of the process, namely gp120 binding, act synergistically with inhibitors of prior and subsequent steps.

Example 2

Background: The increasing incidence of multidrug-resistant HIV-1 mandates the search for novel classes of antiretroviral agents. CCR5 is a requisite fusion coreceptor for primary HIV-1 isolates and provides a promising target for antiviral therapy. PRO140 is an anti-CCR5 monoclonal antibody that potently inhibits HIV-1 entry and replication at concentrations that do not affect CCR5's chemokine receptor activity in vitro. In the present study, we evaluated the therapeutic potential of PRO 140 in vivo using a therapeutic animal model of HIV-1 infection.

Methods: CD-17 SCID mice were reconstituted with normal human PBMC and infected with the R5 isolate HIV-1 JR-CSF. When viral steady state was reached, the animal were treated intraperitoneally with PRO 140 or control antibody and monitored for viral burden using the Roche Amplicor assay. Initial studies examined a single 1 mg dose of PRO140. In multi-dose studies, PRO 140 was administered once every three days for three weeks at doses ranging from 0.1-1.0 mg. In a separate experiment, flow cytometry was used to examine the potential for lymphocyte depletion following PRO 140 injection.

Results: Both single-dose and multi-dose PRO 140 reduced viral loads to undetectable levels in all treated animals, and the viral load reductions ranged to 1.8 log 10. A transitory control of viral replication was observed following single injection of PRO 140 while multiple injections led to a prolonged control with no evidence of viral rebound during therapy. Dose-dependent differences were observed in the kinetics of the PRO 140-mediated reductions in viral load. Flow cytometry analysis showed that treatment with PRO 140 did not lead to lymphocyte depletion, confirming that impact on viral replication in vivo was solely due to CCR5-blockage.

Conclusions: PRO 140 is highly effective in controlling established HIV-1 infection in the hu-PBL-SCID mouse model of HIV-1 infection. These findings provide in vivo proof-of-concept for PRO 140 therapy in particular and for CCR5-inhibitors therapy in general.

Example 3

Methods:

A humanized CCR5 antibody (huPRO 140) was tested for the ability to block RANTES-induced calcium mobilization in L1.2-CCR5 cells and the ability to block replication of HIV-1 CASE C 1/85 in human PBMC's using methods described herein.

Figure 19:
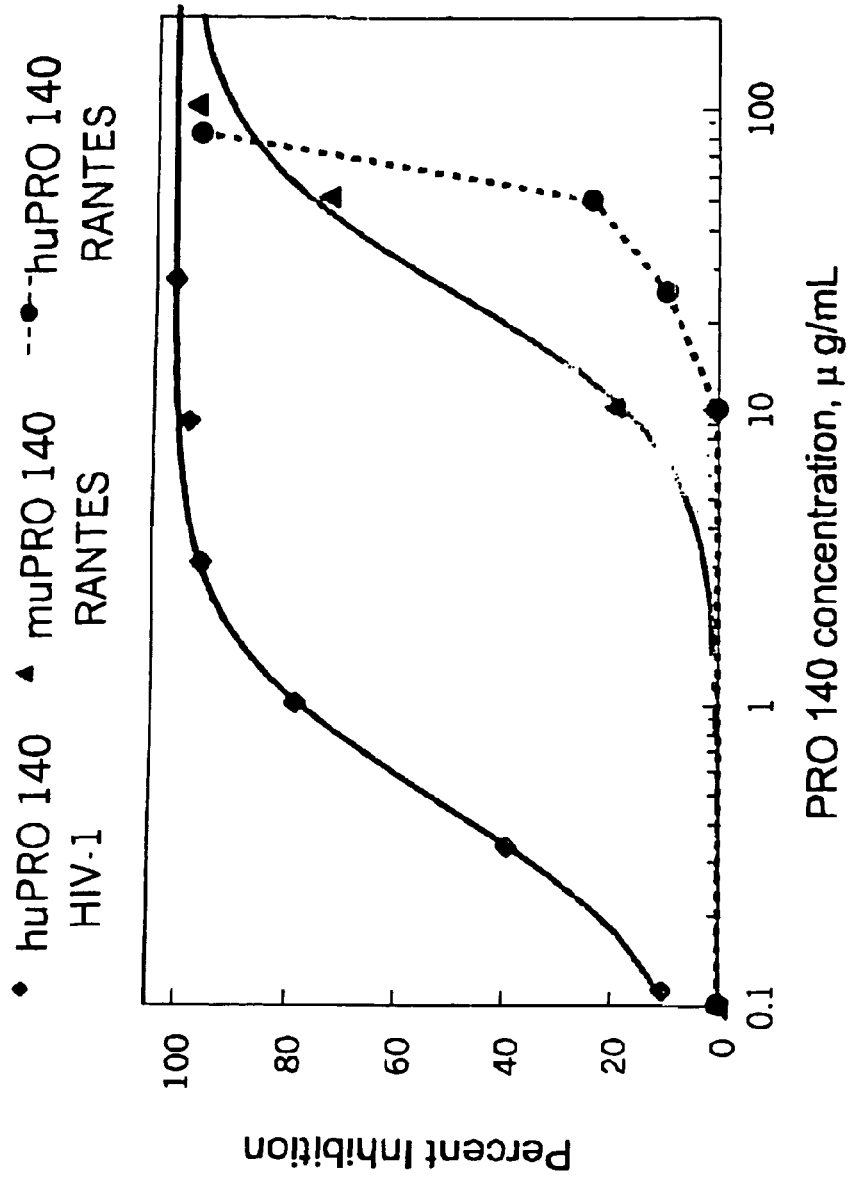

Results:

The results as shown in FIG. 19 shows that the humanized CCR5 antibody potently blocks HIV-1 but not RANTES.

REFERENCES

1. Allaway, G. P., K. L. Davis-Bruno, B. A. Beaudry, E. B. Garcia, E. L. Wong, A. M. Ryder, K. W. Hasel, M. C. Gauduin, R. A. Koup, J. S. McDougal and P. J. Maddon. 1995. Expression and characterization of CD4-IgG2, a novel heterotetramer that neutralizes primary HIV type 1 isolates. AIDS Res Hum Retroviruses 11: 533-539.
2. Allaway, G. P., A. M. Ryder, G. A. Beaudry and P. J. Maddon. 1993. Synergistic inhibition of HIV-1 envelope-mediated cell fusion by CD4-based molecules in combination with antibodies to gp120 or gp41. AIDS Res Hum Retroviruses 9: 581-587.
3. Amara, A., S. L. Gall, O, Schwartz, J. Salamero, M. Montes, P. Loetscher, M. Baggiolini, J. L. Virelizier and F. Arenzana-Seisdedos. 1997. HIV coreceptor downregulation as antiviral principle: SDF-1a-dependent internalization of the chemokine receptor CXCR4 contributes to inhibition of HIV replication. J. Exp. Med. 186: 139-146.
4. Berger, E. A. 1997. HIV entry and tropism: the chemokine receptor connection. AIDS 11 (suppl A): S3-S16.
5. Bieniasz, P. D. and B. R. Cullen. 1998. Chemokine receptors and human immunodeficiency virus infection. Frontiers in Bioscience 3: d44-58.
6. Bieniasz, P. D., R. A. Fridell, I. Aramori, S. S. G. Ferguson, M. C. Caron and B. R. Cullen. 1997. HIV-1-induced cell fusion is mediated by multiple regions within both the viral envelope and the CCR5 co-receptor. EMBO 16: 2599-2609.
7. Brelot, A., N. Heveker, O. Pleskoff, N. Sol and M. Alizon. 1997. Role of the first and third extracellular domains of CXCR4 in human immunodeficiency virus coreceptor activity. J. Virol. 71: 4744-4751.
8. Chan, D. C. and P. S. Kim. 1998. HIV entry and its inhibition. Cell 93: 681-684.
9. Chou, T. C. and D. C. Rideout. Synergism and antagonism in chemotherapy. New York: Academic Press, 1991
10. Cocchi, F., A. L. DeVico, A. Garzino-Derno, S. K. Arya, R. C. Gallo and P. Lusso. 1995. Identification of RANTES, MIP-1α and MIP-1β as the major HIV-suppressive factors produced by CD8 T-cells. Science 270: 1811-1815.
11. Connor, R. I., K. E. Sheridan, D. Ceradini, S. Choe and N. R. Landau. 1997. Change in co-receptor use correlates with disease progression in HIV-1 infected individuals. J. Exp. Med. 185: 621-628.
12. Crump, M. P., J. H. Gong, P. Loetscher, K. Rajarathnam, A. Amara, F. Arenzana-Seisdedos, J. L. Virelizier, M. Baggiolini, B. D. Sykes and I. Clark-Lewis. 1997. Solution structure and basis for functional activity of stromal-cell derived factor-1; disassociation of CXCR4 activation from binding and inhibition of HIV-1. EMBO 16: 6996-7007.
13. Dalgleish, A. G., P. C. L. Beverly, P. R. Clapham, D. H. Crawford, M. F. Greaves and R. A. Weiss. 1984. The CD4 (T4) antigen is an essential component of the receptor for the AIDS retrovirus. Nature 312: 763-766.
14. Deng, H. K., R. Liu, W. Ellmeier, S. Choe, D. Unutmaz, M. Burkhart, P. DiMarizio, S. Marmon, R. E. Sutton, C. M. Hill, S. C. Peiper, T. J. Schall, D. R. Littman and N. R. Landau. 1996. Identification of a major co-receptor for primary isolates of HIV-1. Nature 381: 661-666.
15. Dimitrov, D. S. 1997. How do viruses enter cells? The HIV Co-receptors teach us a lesson of complexity. Cell 91: 721-730.
16. Donzella, G. A., D. Schols, S. W. Lin, K. A. Nagashima, P. J. Maddon, G. P. Allaway, T. P. Sakmar, E. D. Clercq and J. P. Moore. 1998. JM3100, a small molecule that interacts with the CXCR4 co-receptor to prevent HIV-1 entry. Nat. Med. 4: 72-77.
17. Doranz, B. J., K. Grovit-Ferbas, M. P. Sharron, S. H. Mao, M. B. Goetz, E. S. Daar, R. W. Doms and W. A. O'Brien. 1997. A small molecule inhibitor directed against the chemokine receptor CXCR4 prevents its use as an HIV-1 co-receptor. J. Ex. Med. 186: 1395-1400.
18. Doranz, B. J., Z.-H. Lu, J. Rucker, T.-Y. Zhang, M. Sharron, Y.-H. Cen, Z.-X. Wang, H.-H. Guo, J.-G. Du, M. A. Accavitti, R. W. Doms and S. C. Peiper. 1997. Two distinct CCR5 domains can mediate co-receptor usage by human immunodeficiency virus type 1. J. Virol. 71: 6305-6314.
19. Dragic, T., V. Litwin, G. P. Allaway, S. R. Martin, Y. Huanh, K. A. Nagashima, C. Cayanan, P. J. Maddon, R. A. Koup, J. P. Moore and W. A. Paxton. 1996. HIV-1 entry into CD4+ cells is mediated by the chemokine receptor CC-CKR-5. Nature 381: 667-673.
20. Dragic, T., A. Trkola, X. W. Lin, K. A. Nagashima, F. Kajumo, L. Zhao, W. C. Olson, L. Wu, C. R. Mackay, G. P. Allaway, T. P. Sakmar, J. P. Moore and P. J. Maddon. 1998. Amino terminal substitutions in the CCR5 co-receptor impair gp120 binding and human immunodeficiency virus type 1 entry. J. Virol. 72: 279-285.
21. Dragic, T., A. Trkola and J. P. Moore. 1997. HIV co-receptors: Gateways to the cell. Advances in Research and Therapy 7: 2-13.
22. Farzan, M., H. Choe, L. Vaca, K. Martin, Y. Sun, E. Desjardins, N. Ruffing, L. Wu, R. Wyatt, N. Gerard, C. Gerard and J. Sodroski. 1998. A tyrosine-rich region in the N-terminus of CCR5 is important for human immunodeficiency virus type 1 entry and mediates an association between gp12.0 and CCR5. J. Virol. 72: 1160-1164.
23. Fuerst, T. R., E. G. Niles, F. W. Studier and B. Moss. 1986. Eukaryotic transient-expression system based on recombinant vaccinia virus that synthesizes bacteriophage T7 RNA polymerase. Proc. Natl. Acad. Sci. USA. 83: 8122-8126.
24. Genoud, S., F. Kajumo, Y. Guo, D. A. D. Thompson and T. Dragic. CCR5-mediated human immunodeficiency virus entry depends on an amino-terminal domain gp120-binding site and on the conformational integrity of all four extracellular domains. J. Virol. submitted.
25. Gether, U. and B. K. Kobilka. 1998. G protein-coupled receptors. J. Biol. Chem. 273: 17979-17982.
26. Gordon, C., M. Muesing, A. E. I. Proudfoot, C. A. Power, J. P. Moore and A. Trkola. 1998. Enhancement of human immunodeficiency virus type 1 infection by the CC-chemokine RANTES is independent of the mechanism of virus-cell fusion. J. Virol. in press.
27. Heveker, N., M. Montes, L. Germeroth, A. Amara, A. Trautmann, M. Alizon and J. Schneider-Mergener. 1998.

27. (cont.) Dissociation of the signaling and antiviral properties of SDF-1-derived small peptides. Current Biology 8: 369-376.
28. Hill, C. M., D. Kwon, M. Jones, C. B. Davis, S. Marmon, B. L. Daugherty, J. A. DeMartino, M. S. Springer, D. Unutmaz and D. R. Littman. 1998. The amino terminus of human CCR5 is required for its function as a receptor for diverse human and simian immunodeficiency virus envelope glycoproteins. Virology 248: 357-371.
29. Johnson, V. A., D. P. Merrill, J. A. Videler, T. C. Chou, R. E. Byington, J. J. Eron, R. T. D'Aquila and M. S. Hirsch. 1991. Two-drug combinations of zidovudine, didanosine, and recombinant interferon-alpha A inhibit replication of zidovudine-resistant human immunodeficiency virus type 1 synergistically in vitro. J Infect Dis 164: 646-655.
30. Klatzmann, D., E. Champagne, S. Chamaret, J. M. Gruest, D. Guetard, T. Hercend, J. C. Gluckman and L. Montagnier. 1984. T-lymphocyte T4 molecule behaves as the receptor for human retrovirus LAV. Nature 312: 382-385.
31. Kuhmann, K. E., E. J. Platt, S. L. Kozak and D. Kabat. 1997. Polymorphism in the CCR5 genes of African green monkeys and mice implicate specific amino acids in infections by simian and human immunodeficiency viruses. J. Virol. 71: 8642-8656.
32. Kwong, P. D., R. Wyatt, J. Robinson, R. W. Sweet, J. Sodroski and W. A. Hendrickson. 1998. Structure of an HIV gp120 envelope glycoprotein in complex with the CD4 receptor and a neutralizing human antibody. Nature 393: 648-659.
33. Laal, S., S. Burda, M. K. Gorny, S. Karwowska, A. Buchbinder and S. Zolla-Pazner. 1994. Synergistic neutralization of human immunodeficiency virus type 1 by combinations of human monoclonal antibodies. J. Virol. 68: 4001-4008.
34. Labrosse, B., A. Brelot, N. Heveker, N. Sol, D. Schols, E. D. Clercq and M. Alizon. 1998. Determinants for sensitivity of human immunodeficiency virus co-receptor CXCR4 to the bicyclam AMD3100. J. Virol. 72: 6381-6388.
35. Li, A., H. Katinger, M. R. Posner, L. Cavacini, S. Zolla-Pazner, M. K. Gorny, J. Sodroski, T. C. Chou, T. W. Baba and R. M. Ruprecht. 1998. Synergistic neutralization of simian-human immunodeficiency virus SHIV-vpu+ by triple and quadruple combinations of human monoclonal antibodies and high-titer anti-human immunodeficiency virus type 1 immunoglobulins. J. Virol. 72: 3235-3240.
36. Littman, D. R. 1998. Chemokine receptors: keys to AIDS pathogenesis. Cell 93: 677-680.
37. Litwin, V. unpublished results.
38. Litwin, V., K. Nagashima, A. M. Ryder, C. H. Chang, J. M. Carver, W. C. Olson, M. Alizon, K. W. Hasel, P. J. Maddon and G. P. Allaway. 1996. Human immunodeficiency virus type 1 membrane fusion mediated by a laboratory-adapted strain and a primary isolate analyzed by resonance energy transfer. J. Virol. 70: 6437-6441.
39. Loetscher, P., J. H. Gong, B. Dewald, M. Baggioloni and I. Clark-Lewis. 1998. N-terminal peptides of stromal cell derived factor-1 with CXC chemokine receptor 4 agonist and antagonist activities. J. Biol. Chem. 273: 22279-22283.
40. Mack, M., B. Luckow, P. J. Nelson, J. Cihak, G. Simmons, P. R. Clapham, N. Signoret, M. Marsh, M. Stangassinger, F. Borlat, T. N. C. Wells, D. Schlondorff and A. E. I. Proudfoot. 1998. Aminooxypentane-RANTES induces CCR5 internalization but inhibits recycling: a novel inhibitory mechanisms of HIV infectivity. J. Ex. Med. 187: 1215-1224.
41. Maddon, P. J., A. G. Dalgleish, J. S. McDougal, P. R. Clapham, R. A. Weiss and R. Axel. 1986. The T4 gene encodes the AIDS virus receptor and is expressed in the immune system and the brain. Cell 47: 333-348.
42. McDougal, J. S., M. S. Kennedy, J. M. Sligh, S. P. Cort, A. Mawle and J. K. A. Nicholson. 1986. Binding of HTLVIII/LAV to $T4^+$ T cells by a complex of the 110K viral protein and the T4 molecule. Science 231: 382-385.
43. McKnight, A., D. Wilkinson, G. Simmons, S. Talbot, L. Picard, M. Ahuja, M. Marsh, J. A. Hoxie and P. R. Clapham. 1997. Inhibition of human immunodeficiency virus fusion by a monoclonal antibody to a co-receptor (CXCR4) is both cell type and virus strain dependent. J. Virol. 71: 1692-1696.
44. Merrill, D. P., D. J. Manion, T. C. Chou and M. S. Hirsch. 1997. Antagonism between human immunodeficiency virus type 1 protease inhibitors indinavir and saquinavir in vitro. J Infect Dis 176: 265-268.
45. Moore, J. P., Y. Cao, L. Qing, Q. J. Sattentau, J. Pyati, R. Koduri, J. Robinson, C. F. Barbas, D. R. Burton and D. D. Ho. 1995. Primary isolates of human immunodeficiency virus type 1 are relatively resistant to neutralization by monoclonal antibodies to gp120 and their neutralization is not predicted by studies with monomeric gp120. J. Virol. 69: 101-109.
46. Moore, J. P., B. A. Jameson, R. A. Weiss and Q. J. Sattentau. The HIV-cell fusion reaction. Boca Raton: CRC Press Inc., 1993 (J. Bentz, ed. Viral Fusion Mechanisms)
47. Moore, J. F., O. A. McKeating, Y. Huang, A. Ashkenazi and D. D. Ho. 1992. Virions of primary human immunodeficiency virus type 1 isolates resistant to soluble CD4 (sCD4) neutralization differ in sCD4 binding and glycoprotein gp120 retention from sCD4-sensitive isolates. J. Virol. 66: 235-249.
48. Moore, J. P. and R. W. Sweet. 1993. The HIV gp120-CD4 interaction: a target for pharmacological and immunological intervention. Prospect in Drug Discovery and Design 1: 235-250.
49. Murakami, T., T. Nakajima, Y. Koyanagi, K. Tachibana, N. Fujii, H. Tamamura, N. Yoshida, M. Waki, A. Matsumoto, O. Yoshie, T. Kishimoto, N. Yamamoto and T. Nagasawa. 1997. A small molecule CXCR4 inhibitor that blocks T cell line-tropic HIV-1 infection. J. Ex. Med. 186: 1389-1393.
50. Olson, W. C. unpublished results.
51. Pantaleo, G., G. Poli, L. Butini, C. Fox, A. I. Dayton and A. S. Fauci. 1991. Dissociation between syncytia formation and HIV spreading. Suppression of syncytia does not necessarily reflect inhibition of HIV infection. Eur. J. Immunol. 21: 1771-1774.
52. Rabut, G. E. E., J. A. Konner, F. Kajumo, J. P. Moore and T. Dragic. 1998. Alanine substitutions of polar and nonpolar residues in the amino-terminal domain of CCR5 differently impair entry of macrophage- and dual-tropic isolates of the human immunodeficiency virus type 1. J. Virol. 72: 3464-3468.
53. Rizzuto, C., R. Wyatt, N. Hernandez-Ramos, Y. Sun, P. Kwong, W. Hendrickson and J. Sodroski. 1998. Identification of a conserved human immunodeficiency virus gp120 glycoprotein structure important for chemokine receptor binding. Science 280: 1949-1953.
54. Rucker, J., M. Samson, B. J. Doranz, F. Libert, J. F. Berson, Y. Yi, R. J. Smyth, R. G. Collman, C. C. Broder, G. Vassart, R. W. Doms and M. Parmentier. 1996. Regions in the β-chemokine receptors CCR-5 and CCR-2b that determine HIV-1 cofactor specificity. Cell 87: 437-446.

55. Schols, D., S. Struyf, J. V. Damme, J. A. Este, G. Henson and E. D. Clercq. 1997. Inhibition of T-tropic HIV strains by selective antagonization of the chemokine receptor CXCR4. J. Ex. Med. 186: 1383-1388.
56. Simmons, G., P. R. Clapham, L. Picard, R. E. Offord, M. M. Rosenkilde, T. W. Schwartz, R. Buser, T. N. C. Wells and A. E. I. Proudfoot. 1997. Potent inhibition of HIV-1 infectivity in macrophages and lymphocytes by a novel CCR5 antagonist. Science 276: 276-279.
57. Simmons, G., D. Wilkinson, J. D. Reeves, M. T. Dittmar, S. Beddows, J. Weber, G. Carnegie, U. Desselberger, P. W. Gray, R. A. Weiss and P. R. Clapham. 1996. Primary, syncytium-inducing human immunodeficiency virus type-1 isolates are dual-tropic and most can use either LESTR or CCR5 as co-receptor for virus entry. J. Virol. 70: 8355-8360.
58. Strizki, J. M., J. Davis-Turner, R. G. Collman, J. Hoxie and F. Gonzalez-Scarano. 1997. A monoclonal antibody (12G5) directed against CXCR4 inhibits infection with the dual-tropic human immunodeficiency virus type 1 isolate HIV-1 89.6 but not the T-tropic isolate HIV-1 HxB. J. Virol. 71: 5678-5683.
59. Trkola, A., T. Dragic, J. Arthos, J. Binley, W. C. Olson, G. P. Allaway, C. Cheng-Mayer, J. Robinson, P. J. Maddon and J. P. Moore. 1996. CD4-dependent, antibody sensitive interactions between HIV-1 and its co-receptor CCR-5. Nature 384: 184-187.
60. Trkola, A., W. A. Paxton, S. P. Monard, J. A. Hoxie, M. A. Siani, D. A. Thompson, L. Wu, C. R. Mackay, R. Horuk and J. P. Moore. 1997. Genetic subtype-independent inhibition of human immunodeficiency virus type-1 replication by CC- and CXC chemokines. J. Virol. 72: 396-404.
61. Vijh-Warrier, S., A. Pinter, W. J. Honnen and S. A. Tilley. 1996. Synergistic neutralization of human immunodeficiency virus type 1 by a chimpanzee monoclonal antibody against the V2 domain of gp120 in combination with monoclonal antibodies against the V3 loop and the CD4-binding site. J. Virol. 70: 4466-4473.
62. Ward, S. G., K. bacon and J. Westwick. 1998. Chemokines and lymphocytes: more than an attraction. Immunity 9: 1-11.
63. Wu, L., N. P. Gerard, R. Wyatt, H. Choe, C. Parolin, N. Ruffing, A. Borsetti, A. A. Cardoso, E. Desjardin, W. Newman, C. Gerard and J. Sodroski. 1996. CD4-induced interaction of primary HIV-1 gp120 glycoproteins with the chemokine receptor CCR-5. Nature 384: 179-183.
64. Wu, L., G. LaRosa, N. Kassam, C. J. Gordon, H. Heath, N. Ruffing, H. Chen, J. Humblias, M. Samson, M. Parmentier, J. P. Moore and C. R. Mackay. 1997. Interaction of chemokine receptor CCR5 with its ligands: multiple domains for HIV-1 gp120 binding and a single domain for chemokine binding. J. Exp. Med. 186: 1373-1381.
65. Wyatt, R., P. D. Kwong, E. Desjardins, R. Sweet, J. Robinson, W. Hendrickson and J. Sodroski. 1998. The antigenic structure of the human immunodeficiency virus gp120 envelope glycoprotein. Nature 393: 705-711.
66. Wyatt, R. and J. Sodroski. 1998. The HIV-1 envelope glycoproteins: fusogens, antigens and immunogens. Science 280: 1884-1888.
67. Ylisastigui, L., J. J. Vizzavona, E. Drakopoulou, P. Paindavoine, C. F. Calvo, M. Parmentier, J. C. Gluckman, C. Vita and A. Benjouad. 1998. Synthetic full length and truncated RANTES inhibit HIV-1 infection of primary macrophages. AIDS 12: 977-984.
68. Zhang, J. L., H. Choe, B. J. Dezube, M. Farzan, P. L. Sharma, X. C. Zhou, L. B. Chen, M. Ono, S. Gillies, Y. Wu, J. G. Sodroski and C. S. Crumpacker. 1998. The bis-azo compound FP-21399 inhibits HIV-1 replication by preventing viral entry. Virology 244: 530-541.
69. Cairns, J. S., D'Souza. M. P., 1998. Chemokines and HIV-1 second receptors: the therapeutic connection. Nature Medicine. 1998. Vol 4, No. 5: 563.
70. Kilby, J. Michael, et al. 1998. Potent suppression of HIV-1 replication in humans by T-20, a peptide inhibitor of gp41-medicated virus entry. Nature Medicine. Vol. 3, No. 11: 1302.
71. U.S. Pat. No. 4,816,567, issued Mar. 28, 1989 to Cabilly et al.
72. U.S. Pat. No. 5,225,539, issued Jul. 6, 1993 to Gregory Winter.
73. U.S. Pat. No. 5,585,089, issued Dec. 17, 1996 to Queen et al.
74. U.S. Pat. No. 5,693,761, issued Dec. 2, 1997 to Queen et al.
75. PCT International Application No. PCT/US89/05857, filed Dec. 28, 1989, published Jul. 26, 1990, WO 90/07861.

---

What is claimed:

1. An anti-CCR5 antibody fragment comprising an antibody fragment selected from the group consisting of:
    (a) a light chain, which light chain comprises the expression product of a plasmid designated pVK:HuPRO140-VK (ATCC Deposit Designation PTA-4097);
    (b) a heavy chain, which heavy chain comprises the expression product of either a plasmid designated pVg4:HuPRO140 HG2-VH (ATCC Deposit Designation PTA-4098) or a plasmid designated pVg4:HuPRO140 (mut B+D+I)-VH (ATCC Deposit Designation PTA-4099);
    (c) a Fab fragment which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg4:HuPRO140 HG2-VH (ATCC Deposit Designation PTA-4098) or a plasmid designated pVg4:HuPRO140 (mut B+D+I)-VH (ATCC Deposit Designation PTA-4099); and
    (d) a F(ab')₂ fragment which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg4:HuPRO140 HG2-VH (ATCC Deposit Designation PTA-4098) or a plasmid designated pVg4:HuPRO140 (mut B+D+I)-VH (ATCC Deposit Designation PTA-4099);
and which antibody fragment binds to CCR5 on the surface of a human cell.

2. The anti-CCR5 antibody fragment of claim 1, wherein the antibody fragment is the light chain expressed by the plasmid designated pVK:HuPRO140-VK (ATCC Deposit Designation PTA-4097).

3. The anti-CCR5 antibody fragment of claim 1, wherein the antibody fragment is the heavy chain expressed by the plasmid designated pVg4:HuPRO140 HG2-VH (ATCC Deposit Designation PTA-4098).

4. The anti-CCR5 antibody of claim 1, wherein the antibody fragment is the heavy chain expressed by the plasmid designated pVg4:HuPRO140 (mut B+D+I)-VH (ATCC Deposit Designation PTA-4099).

5. The anti-CCR5 antibody fragment of claim 1, wherein the antibody fragment is the Fab fragment of the anti-CCR5 antibody which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg4:HuPRO140 HG2-VH (ATCC Deposit Designation PTA-4098) or a plasmid designated pVg4:HuPRO140 (mut B+D+I)-VH (ATCC Deposit Designation PTA-4099).

6. The anti-CCR5 antibody fragment of claim 1, wherein the antibody fragment is the F(ab')₂ fragment of the anti-CCR5 antibody which comprises (i) two light chains, each light chain comprising the expression product of a plasmid designated pVK:HuPRO140-VK (ATCC Deposit Designation PTA-4097), and (ii) two heavy chains, each heavy chain comprising the expression product of either a plasmid designated pVg4:HuPRO140 HG2-VH (ATCC Deposit Designation PTA-4098) or a plasmid designated pVg4:HuPRO140 (mut B+D+I)-VH (ATCC Deposit Designation PTA-4099).

7. The anti-CCR5 antibody fragment of claim 5, wherein the heavy chains comprise the expression product of the plasmid designated pVg4:HuPRO140 HG2-VH (ATCC Deposit Designation PTA-4098).

8. The anti-CCR5 antibody fragment of claim 5, wherein the heavy chains comprise the expression product of the plasmid designated pVg4:HuPRO140 (mut B+D+I)-VH (ATCC Deposit Designation PTA-4099).

9. The anti-CCR5 antibody fragment of claim 6, wherein the heavy chains comprise the expression product of the plasmid designated pVg4:HuPRO140 HG2-VH (ATCC Deposit Designation PTA-4098).

10. The anti-CCR5 antibody fragment of claim 6, wherein the heavy chains comprise the expression product of the plasmid designated pVg4:HuPRO140 (mut B+D+I)-VH (ATCC Deposit Designation PTA-4099).

11. An anti-CCR5 antibody fragment comprising (i) a light chain which comprises consecutive amino acids having the sequence set forth in SEQ ID NO:6; or (ii) a heavy chain which comprises consecutive amino acids having the sequence set forth in SEQ ID NO:9 or SEQ ID NO:12.

12. A composition comprising the anti-CCR5 antibody fragment of claim 1 or claim 11 and a carrier, a diluent or an excipient.

13. The composition of claim 12, wherein the anti-CCR5 antibody fragment has attached thereto a material selected from the group consisting of a radioisotope, a toxin, polyethylene glycol, a cytotoxic agent and a detectable label.

14. A method of inhibiting HIV-1 infection of a CD4+ cell which comprises contacting the CD4+ cell with the anti-CCR5 antibody fragment of claim 1 or claim 11, in an amount and under conditions such that fusion of HIV-1 or an HIV-1 infected cell to the CD4+ cell is inhibited, thereby inhibiting HIV-1 infection of the CD4+ cell.

15. The method of claim 14, which further comprises labeling the anti-CCR5 antibody fragment with a detectable marker.

16. The method of claim 15, wherein the detectable marker is a radioactive or a fluorescent marker.

17. The method of claim 14, wherein the CD4+ cell expresses CCR5.

18. A method of treating a subject afflicted with HIV-1 which comprises administering to the subject an effective HIV-1 treating dosage amount of the composition of claim 12, under conditions effective to treat said HIV-1-afflicted subject.

19. The method of claim 18, wherein the composition is administered to the subject by a method selected from the group consisting of intravenous, intramuscular and subcutaneous means.

20. The method of claim 18, wherein the composition is administered continuously to said subject or at predetermined periodic intervals.

21. The method of claim 18, wherein the dosage of said composition ranges from about 0.1 to about 100,000 µg/kg body weight of said subject.

22. The method of claim 18, wherein the dosage of said composition does not inhibit an endogenous chemokine activity on CCR5 in said subject.

23. A method of preventing a subject from contracting an HIV-1 infection which comprises administering to the subject an effective HIV-1 infection-preventing dosage amount of the composition of claim 12, under conditions effective to prevent said HIV-1 infection in said subject.

24. The method of claim 23, wherein the anti-CCR5 antibody fragment is administered to the subject by a method selected from the group consisting of intravenous, intramuscular and subcutaneous means.

25. The method of claim 23, wherein the anti-CCR5 antibody fragment is administered continuously to said subject or at predetermined periodic intervals.

26. The method of claim 23, wherein the dosage of said anti-CCR5 antibody fragment ranges from about 0.1 to about 100,000 µg/kg body weight of said subject.

27. The method of claim 23, wherein the dosage of said anti-CCR5 antibody fragment does not inhibit an endogenous chemokine activity on CCR5 in said subject.

* * * * *

SEQUENCE LISTING

```
<160> NUMBER OF SEQ ID NOS: 13

<210> SEQ ID NO 1
<211> LENGTH: 31
<212> TYPE: PRT
<213> ORGANISM: HUMAN

<400> SEQUENCE: 1

Met Asp Tyr Gln Val Ser Ser Pro Ile Tyr Asp Ile Asn Tyr Tyr Thr
1               5                   10                  15

Ser Glu Pro Cys Gln Lys Ile Asn Lys Gln Ile Ala Ala Ala Arg
            20                  25                  30

<210> SEQ ID NO 2
<211> LENGTH: 15
<212> TYPE: PRT
<213> ORGANISM: HUMAN
```

<400> SEQUENCE: 2

His Tyr Ala Ala Ala Gln Trp Asp Phe Gly Asn Thr Met Cys Gln
1               5                   10                  15

<210> SEQ ID NO 3
<211> LENGTH: 27
<212> TYPE: PRT
<213> ORGANISM: HUMAN

<400> SEQUENCE: 3

Arg Ser Gln Lys Glu Gly Leu His Tyr Thr Cys Ser Ser His Phe Pro
1               5                   10                  15

Tyr Ser Gln Tyr Gln Phe Trp Lys Asn Phe Gln
            20                  25

<210> SEQ ID NO 4
<211> LENGTH: 17
<212> TYPE: PRT
<213> ORGANISM: HUMAN

<400> SEQUENCE: 4

Gln Glu Phe Phe Gly Leu Asn Asn Cys Ser Ser Ser Asn Arg Leu Asp
1               5                   10                  15

Gln

<210> SEQ ID NO 5
<211> LENGTH: 429
<212> TYPE: DNA
<213> ORGANISM: Homo sapiens

<400> SEQUENCE: 5
tctagaccac catgaagttg cctgttaggc tgttggtgct gatgttctgg attcctgctt      60
ccagcagtga tattgtgatg acccaatctc cactctccct gcctgtcact cctggagagc    120
cagcctccat ctcttgcaga tctagtcagc gccttctgag cagttatgga catacctatt    180
tacattggta cctacagaag ccaggccagt ctccacagct cctgatctac gaagtttcca    240 accgatttc tggggtccca gacaggttca gtggcagtgg gtcagggaca gatttcacac    300
ttaagatcag tagagtggag gctgaggatg tgggagttta ttactgctct caaagtacac    360
atgttcctct cacgttcgga caggggacca aggtggaaat aaaacgtaag tagtcttctc    420
aactctaga                                                            429

<210> SEQ ID NO 6
<211> LENGTH: 131
<212> TYPE: PRT
<213> ORGANISM: Homo sapiens

<400> SEQUENCE: 6

Met Lys Leu Pro Val Arg Leu Leu Val Leu Met Phe Trp Ile Pro Ala
1               5                   10                  15

Ser Ser Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Arg Leu
        35                  40                  45

Leu Ser Ser Tyr Gly His Thr Tyr Leu His Trp Tyr Leu Gln Lys Pro
    50                  55                  60

Gly Gln Ser Pro Gln Leu Leu Ile Tyr Glu Val Ser Asn Arg Phe Ser
65                  70                  75                  80

```
Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ser Gln Ser Thr His Val Pro Leu Thr Phe Gly Gln Gly Thr Lys Val
        115                 120                 125

Glu Ile Lys
    130

<210> SEQ ID NO 7
<211> LENGTH: 393
<212> TYPE: DNA
<213> ORGANISM: Homo sapiens

<400> SEQUENCE: 7
atgaagttgc ctgttaggct gttggtgctg atgttctgga ttcctgcttc cagcagtgat      60
attgtgatga cccaatctcc actctccctg cctgtcactc tggagagcc agcctccatc     120 tcttgcagat ctagtcagcg ccttctgagc agttatggac atacctattt acattggtac     180
ctacagaagc caggccagtc tccacagctc ctgatctacg aagtttccaa ccgattttct     240
ggggtcccag acaggttcag tggcagtggg tcagggacag atttcacact aagatcagt      300 agagtggagg ctgaggatgt gggagtttat tactgctctc aaagtacaca tgttcctctc     360
acgttcggac aggggaccaa ggtggaaata aaa                                  393

<210> SEQ ID NO 8
<211> LENGTH: 457
<212> TYPE: DNA
<213> ORGANISM: Homo sapiens

<400> SEQUENCE: 8
acgcgtccac catggaatgg agcggagtct ttatctttct cctgtcagta actgcaggtg      60
tccactccga ggtgcagctg gtggagtctg gtggaggctt ggtaaagcct ggaggttccc     120
ttagactctc ctgtgcagcc tctggttaca ctttcagtaa ctattggatc ggatgggtcc     180
gccaggctcc aggcaaaggg ctggagtgga ttggcgatat taccctgga gggaactaca      240 tcaggaacaa tgagaagttc aaggacaaga ccaccctgtc agcagatact tccaagaaca     300
cagcctatct gcaaatgaac agcctgaaaa ccgaggacac agccgtgtat tactgtggaa     360
gcagcttcgg tagtaactac gtgttcgcct ggtttactta ctggggccaa gggactctgg     420
tcacagtctc ctcaggtgag tccttaaaac tctaga                               457

<210> SEQ ID NO 9
<211> LENGTH: 141
<212> TYPE: PRT
<213> ORGANISM: Homo sapiens

<400> SEQUENCE: 9

Met Glu Trp Ser Gly Val Phe Ile Phe Leu Leu Ser Val Thr Ala Gly
1               5                   10                  15

Val His Ser Glu Val Gln Leu Val Glu Ser Gly Gly Leu Val Lys
            20                  25                  30

Pro Gly Gly Ser Leu Arg Leu Ser Cys Ala Ala Ser Gly Tyr Thr Phe
        35                  40                  45

Ser Asn Tyr Trp Ile Gly Trp Val Arg Gln Ala Pro Gly Lys Gly Leu
    50                  55                  60

Glu Trp Ile Gly Asp Ile Tyr Pro Gly Gly Asn Tyr Ile Arg Asn Asn
```

```
                65                  70                  75                  80
Glu Lys Phe Lys Asp Lys Thr Thr Leu Ser Ala Asp Thr Ser Lys Asn
                        85                  90                  95

Thr Ala Tyr Leu Gln Met Asn Ser Leu Lys Thr Glu Asp Thr Ala Val
            100                 105                 110

Tyr Tyr Cys Gly Ser Ser Phe Gly Ser Asn Tyr Val Phe Ala Trp Phe
        115                 120                 125

Thr Tyr Trp Gly Gln Gly Thr Leu Val Thr Val Ser Ser
    130                 135                 140
```

<210> SEQ ID NO 10
<211> LENGTH: 423
<212> TYPE: DNA
<213> ORGANISM: Homo sapiens

<400> SEQUENCE: 10

```
atggaatgga gcggagtctt tatctttctc ctgtcagtaa ctgcaggtgt ccactccgag     60
gtgcagctgg tggagtctgg tggaggcttg gtaaagcctg aggttccct tagactctcc    120
tgtgcagcct ctggttacac tttcagtaac tattggatcg gatgggtccg ccaggctcca   180
ggcaaaggc tggagtggat tggcgatatc taccctggag ggaactacat caggaacaat    240
gagaagttca aggacaagac caccctgtca gcagatactt ccaagaacac agcctatctg   300
caaatgaaca gcctgaaaac cgaggacaca gccgtgtatt actgtggaag cagcttcggt   360
agtaactacg tgttcgcctg gtttacttac tggggccaag ggactctggt cacagtctcc   420
tca                                                                  423
```

<210> SEQ ID NO 11
<211> LENGTH: 457
<212> TYPE: DNA
<213> ORGANISM: Homo sapiens

<400> SEQUENCE: 11

```
tctagaccac catggaatgg agcggggtct ttatctttct cctgtcagta actgcaggtg     60
tccactccca ggtccaactg gtgcagtctg gacctgatgt gaaaaagcct gggacttcaa    120
tgaagatgtc ctgcaagacg tctggataca ccttcagtaa ctattggatc ggatgggtta    180
ggcaggcgcc tggacaaggc cttgagtgga ttggagatat ttaccctgga gggaactata    240
tcaggaacaa tgagaagttc aaggacaaga ccacactgac ggcagacaca tcgaccagca    300
cggcctacat gcaacttggc agcctgagat ctgaagacac tgccgtctat tactgtggaa    360
gcagcttcgg tagtaactac gtgttcgcct ggtttactta ctggggccaa gggactctgg    420
tcacagtctc ctcaggtgag tccttaaaac tctaga                              457
```

<210> SEQ ID NO 12
<211> LENGTH: 141
<212> TYPE: PRT
<213> ORGANISM: Homo sapiens

<400> SEQUENCE: 12

```
Met Glu Trp Ser Gly Val Phe Ile Phe Leu Leu Ser Val Thr Ala Gly
1               5                   10                  15

Val His Ser Gln Val Gln Leu Val Gln Ser Gly Pro Asp Val Lys Lys
            20                  25                  30

Pro Gly Thr Ser Met Lys Met Ser Cys Lys Thr Ser Gly Tyr Thr Phe
        35                  40                  45
```

-continued

```
Ser Asn Tyr Trp Ile Gly Trp Val Arg Gln Ala Pro Gly Gln Gly Leu
    50                  55                  60

Glu Trp Ile Gly Asp Ile Tyr Pro Gly Gly Asn Tyr Ile Arg Asn Asn
65                  70                  75                  80

Glu Lys Phe Lys Asp Lys Thr Thr Leu Thr Ala Asp Thr Ser Thr Ser
                85                  90                  95

Thr Ala Tyr Met Gln Leu Gly Ser Leu Arg Ser Glu Asp Thr Ala Val
            100                 105                 110

Tyr Tyr Cys Gly Ser Ser Phe Gly Ser Asn Tyr Val Phe Ala Trp Phe
        115                 120                 125

Thr Tyr Trp Gly Gln Gly Thr Leu Val Thr Val Ser Ser
    130                 135                 140
```

<210> SEQ ID NO 13
<211> LENGTH: 423
<212> TYPE: DNA
<213> ORGANISM: Homo sapiens

<400> SEQUENCE: 13

```
atggaatgga gcggggtctt tatctttctc ctgtcagtaa ctgcaggtgt ccactcccag      60
gtccaactgg tgcagtctgg acctgatgtg aaaaagcctg ggacttcaat gaagatgtcc     120
tgcaagacgt ctggatacac cttcagtaac tattggatcg gatgggttag gcaggcgcct     180
ggacaaggcc ttgagtggat tggagatatt taccctggag ggaactatat caggaacaat     240
gagaagttca aggacaagac cacactgacg gcagacacat cgaccagcac ggcctacatg     300
caacttggca gcctgagatc tgaagacact gccgtctatt actgtggaag cagcttcggt     360
agtaactacg tgttcgcctg gtttacttac tggggccaag ggactctggt cacagtctcc     420
tca                                                                   423
```